(12) United States Patent
Zappacosta et al.

(10) Patent No.: US 11,844,697 B2
(45) Date of Patent: Dec. 19, 2023

(54) SYSTEMS AND METHODS FOR KNEE ARTHROPLASTY

(71) Applicant: GLOBUS MEDICAL, INC., Audubon, PA (US)

(72) Inventors: Jason Zappacosta, Philadelphia, PA (US); Timothy J. Blackwell, Phoenixville, PA (US); David Stumpo, Trappe, PA (US)

(73) Assignee: Globus Medical, Inc., Audubon, PA (US)

( * ) Notice: Subject to any disclaimer, the term of this patent is extended or adjusted under 35 U.S.C. 154(b) by 337 days.

(21) Appl. No.: 17/197,369

(22) Filed: Mar. 10, 2021

(65) Prior Publication Data
US 2022/0061999 A1  Mar. 3, 2022

Related U.S. Application Data

(63) Continuation-in-part of application No. 17/011,049, filed on Sep. 3, 2020.

(51) Int. Cl.
*A61F 2/38* (2006.01)
*A61F 2/30* (2006.01)
*A61F 2/46* (2006.01)

(52) U.S. Cl.
CPC .......... *A61F 2/3877* (2013.01); *A61F 2/3094* (2013.01); *A61F 2/30771* (2013.01); *A61F 2/461* (2013.01); *A61F 2002/30322* (2013.01); *A61F 2002/30387* (2013.01); *A61F 2002/30784* (2013.01); *A61F 2002/30985* (2013.01)

(58) Field of Classification Search
CPC .................................................... A61F 2/3877
See application file for complete search history.

(56) References Cited

U.S. PATENT DOCUMENTS

| | | | |
|---|---|---|---|
| 4,479,271 A | 10/1984 | Bolesky et al. | |
| 4,550,448 A | 11/1985 | Kenna | |
| 4,938,769 A | 7/1990 | Shaw | |
| 4,944,756 A | 7/1990 | Kenna | |
| 4,997,445 A | 3/1991 | Hodorek | |
| 5,019,104 A | 5/1991 | Whiteside et al. | |
| 5,024,670 A | 6/1991 | Smith et al. | |
| 5,236,462 A | 8/1993 | Mikhail | |
| 5,358,529 A | 10/1994 | Davidson | |
| 5,609,640 A | 3/1997 | Johnson | |
| 5,702,461 A | 12/1997 | Pappas et al. | |
| 5,807,252 A | 9/1998 | Hassfeld et al. | |
| 5,989,472 A | 11/1999 | Ashby et al. | |

(Continued)

FOREIGN PATENT DOCUMENTS

| EP | 2319460 A | 5/2011 |
|---|---|---|
| JP | 4-329949 A | 11/1992 |

(Continued)

*Primary Examiner* — Javier G Blanco

(57) ABSTRACT

A patella implant for knee arthroplasty includes a cap and a base. The cap has an articulating surface and a plurality of first connection members. The base is to be attached to the backside of a patella of a patient. The base includes a cap support mounted to the cap. The cap support includes a plurality of first connection recesses. Each first connection member of the cap is disposed in a corresponding one of the first connection recesses of the cap support to mount the cap to the base.

10 Claims, 34 Drawing Sheets

(56) References Cited

U.S. PATENT DOCUMENTS

| | | | |
|---|---|---|---|
| 6,073,044 A | 6/2000 | Fitzpatrick et al. |
| 6,499,488 B1 | 12/2002 | Hunter et al. |
| 6,676,704 B1 | 1/2004 | Pope et al. |
| 6,711,431 B2 | 3/2004 | Sarin et al. |
| 6,942,667 B1 | 9/2005 | Song |
| 7,007,699 B2 | 3/2006 | Martinelli et al. |
| 7,077,867 B1 | 7/2006 | Pope et al. |
| 7,274,958 B2 | 9/2007 | Jutras et al. |
| 7,474,223 B2 | 1/2009 | Nycz et al. |
| 7,477,926 B2 | 1/2009 | McCombs |
| 7,643,867 B2 | 1/2010 | Solar et al. |
| 7,720,522 B2 | 5/2010 | Solar et al. |
| 7,780,681 B2 | 8/2010 | Sarin et al. |
| 7,840,256 B2 | 11/2010 | Lakin et al. |
| 7,842,092 B2 | 11/2010 | Otto et al. |
| 8,010,180 B2 | 8/2011 | Quaid et al. |
| 8,148,978 B2 | 4/2012 | Sherman et al. |
| 8,170,645 B2 | 5/2012 | Solar et al. |
| 8,185,184 B2 | 5/2012 | Solar et al. |
| 8,257,360 B2 | 9/2012 | Richard et al. |
| 8,470,047 B2 | 6/2013 | Hazebrouck et al. |
| 8,556,981 B2 | 10/2013 | Jones et al. |
| 8,728,387 B2 | 5/2014 | Jones et al. |
| 8,735,773 B2 | 5/2014 | Lang |
| 8,828,311 B2 | 9/2014 | Medina et al. |
| 8,843,229 B2 | 9/2014 | Vanasse et al. |
| 9,135,374 B2 | 9/2015 | Jones et al. |
| 9,155,819 B2 | 10/2015 | Fonte et al. |
| 9,161,799 B2 | 10/2015 | Benson et al. |
| 9,180,010 B2 | 11/2015 | Dong et al. |
| 9,237,950 B2 | 1/2016 | Hensley et al. |
| 9,415,137 B2 | 8/2016 | Meridew et al. |
| 9,445,909 B2 | 9/2016 | Cohen et al. |
| 9,636,229 B2 | 5/2017 | Lang et al. |
| 9,662,214 B2 | 5/2017 | Li et al. |
| 9,744,044 B2 | 8/2017 | Cohen et al. |
| 9,750,850 B2 | 9/2017 | Fonte et al. |
| 9,801,974 B2 | 10/2017 | Landon |
| 9,820,858 B2 | 11/2017 | Harris et al. |
| D806,247 S | 12/2017 | Kheradpir et al. |
| 9,877,786 B2 | 1/2018 | Zastrozna |
| 9,949,837 B2 | 4/2018 | Wang et al. |
| D816,838 S | 5/2018 | Kheradpir et al. |
| 9,956,020 B2 | 5/2018 | Benson et al. |
| D820,984 S | 6/2018 | Kheradpir et al. |
| 10,016,811 B2 | 7/2018 | Neal |
| D828,561 S | 9/2018 | Kheradpir et al. |
| 10,098,746 B1 | 10/2018 | Moore et al. |
| 10,318,024 B2 | 6/2019 | Gogarty et al. |
| 10,327,904 B2 | 6/2019 | Otto et al. |
| 10,350,074 B2 | 7/2019 | Li et al. |
| 10,398,559 B2 | 9/2019 | Jones et al. |
| 10,405,929 B1 | 9/2019 | Seltmann et al. |
| 10,429,957 B2 | 10/2019 | Gogarty et al. |
| 10,456,143 B2 | 10/2019 | Justin et al. |
| 10,485,676 B2 | 11/2019 | Lang et al. |
| 10,492,913 B2 | 12/2019 | Meridew et al. |
| 10,507,063 B2 | 12/2019 | Zuhars et al. |
| 10,575,906 B2 | 3/2020 | Wu |
| 10,596,660 B2 | 3/2020 | McCarthy et al. |
| 10,614,176 B2 | 4/2020 | Dong et al. |
| 10,869,676 B2 | 12/2020 | Wolfson et al. |
| 2005/0085915 A1* | 4/2005 | Steinberg ........... A61B 17/1684 623/23.72 |
| 2007/0219638 A1 | 9/2007 | Jones et al. |
| 2007/0255412 A1 | 11/2007 | Hajaj et al. |
| 2009/0265013 A1 | 10/2009 | Mandell |
| 2011/0029090 A1 | 2/2011 | Zannis et al. |
| 2013/0166035 A1* | 6/2013 | Landon ................ A61F 2/3877 623/20.2 |
| 2015/0093283 A1 | 4/2015 | Miller et al. |
| 2016/0106552 A1 | 4/2016 | Cardamone et al. |
| 2017/0027707 A1 | 2/2017 | Cremascoli |
| 2017/0189194 A1* | 7/2017 | Klinger ................ A61F 2/3877 |
| 2018/0014938 A1 | 1/2018 | Hagen et al. |
| 2018/0200001 A1 | 7/2018 | Erbe |
| 2018/0200007 A1 | 7/2018 | Zastrozna |
| 2018/0200066 A1 | 7/2018 | Wang et al. |
| 2018/0256336 A1 | 9/2018 | Mueller et al. |
| 2018/0338799 A1 | 11/2018 | Hladio et al. |
| 2019/0029830 A1 | 1/2019 | Nguyen et al. |
| 2019/0029847 A1 | 1/2019 | Nguyen et al. |
| 2019/0083270 A1 | 3/2019 | Milz et al. |
| 2019/0151114 A1 | 5/2019 | Sack |
| 2019/0290441 A1 | 9/2019 | Tong et al. |
| 2019/0298525 A1 | 10/2019 | Wright et al. |
| 2019/0298533 A1 | 10/2019 | Kane |
| 2019/0328534 A1 | 10/2019 | Otto et al. |
| 2019/0336037 A1 | 11/2019 | Huang et al. |
| 2019/0343639 A1 | 11/2019 | Nguyen et al. |
| 2019/0350717 A1 | 11/2019 | Tuttle |
| 2019/0351505 A1 | 11/2019 | O'Neill et al. |
| 2019/0377432 A1 | 12/2019 | Gogarty et al. |
| 2020/0054346 A1 | 2/2020 | Justin et al. |
| 2020/0060769 A1 | 2/2020 | Dees, Jr. et al. |
| 2020/0306048 A1 | 10/2020 | Jones et al. |
| 2021/0177614 A1* | 6/2021 | Webb .................... A61F 2/3877 |

FOREIGN PATENT DOCUMENTS

| | | |
|---|---|---|
| JP | 2011-92739 A | 5/2011 |
| JP | 2014523297 A | 9/2014 |

* cited by examiner

SYSTEMS AND METHODS FOR KNEE ARTHROPLASTY

CROSS-REFERENCE TO RELATED APPLICATION(S)

This application is a continuation-in-part of U.S. patent application Ser. No. 17/011,049, filed Sep. 3, 2020, the entire contents of which is hereby incorporated by reference in its entirety for all purposes.

FIELD

The present disclosure generally relates to knee arthroplasty and, in particular, to knee arthroplasty implants and methods of installing knee arthroplasty implants.

BACKGROUND

Knee arthroplasty, often called a knee replacement, is a surgical procedure used to reconstruct and resurface a knee that has been damaged, such as by arthritis. Total knee arthroplasty devices replace both the tibiofemoral joint and the patellafemoral joint. The tibiofemoral joint is where the tibia and the femur articulate. The patellafemoral joint is where the patella and the femur articulate. To replace the tibiofemoral joint, knee arthroplasty includes a femoral trial (or implant) secured to the distal end of the femur, a tibial tray (or implant) secured to the proximal end of the tibia, and an insert disposed therebetween. The femoral implant and tibial implant cap the ends of the femur and tibia, respectively, which form the knee joint, thereby reconstructing the knee. To replace the patellafemoral joint, knee arthroplasty includes a patella prosthesis (or implant) to replace the backside of the patella and form a replacement articulating surface which interfaces with the femoral trial.

SUMMARY

In one aspect, a tibial implant for knee arthroplasty includes a tibial plate sized and shaped for placement on a proximal end of a tibia of a patient. The tibial plate includes opposite proximal and distal surfaces. The distal surface is configured to engage the end of the tibia. A tibial keel extends distally from the distal surface of the tibial plate and is configured to be inserted into the proximal end of the tibia. At least one anchoring projection extends distally from the distal surface of the tibial plate and is configured to be inserted into the proximal end of the tibia.

In another aspect, a method of verifying the implantation of a tibial implant relative to a proximal end of a tibia of a patient includes: positioning the tibial implant relative to the proximal end of the tibia; positioning a position indicator of a position verification system relative to the tibial implant; determining the position of the tibial implant by tracking the position of the position indicator with a tracker of the position verification system; determining the position of the tibia; and verifying that the tibial implant is correctly positioned relative to the proximal end of the tibia by comparing the position of the tibial implant relative to the position of the tibia.

In another aspect, a patella implant for knee arthroplasty comprises a cap including an articulating surface. The cap has a plurality of first connection members. A base is configured to be attached to the backside of a patella of a patient. The base includes a cap support mounted to the cap. The cap support includes a plurality of first connection recesses. Each first connection member of the cap is disposed in a corresponding one of the first connection recesses of the cap support to mount the cap to the base.

In another aspect, a base of a patella implant for knee arthroplasty comprises a cap support configured to be attached to a cap of the patella implant. The cap support includes a plurality of first connection recesses. Each first connection recess is configured to receive a corresponding first connection member of the cap to attach the cap to the cap support. At least one anchoring projection extends from the cap support and is configured to be inserted into the backside of the patella.

In another aspect, a method of forming a patella implant comprises forming a base with a plurality of first connecting recesses and molding a material onto the base to form a cap with an articulating surface. The molding includes substantially filling the plurality of first connecting recesses with the material.

Other objects and features of the present disclosure will be in part apparent and in part pointed out hereinafter.

BRIEF DESCRIPTION OF THE DRAWINGS

Corresponding reference characters indicate corresponding parts throughout the drawings.

DETAILED DESCRIPTION OF THE DISCLOSURE

Various different systems and methods for carrying out and performing knee arthroplasty are disclosed here. The different systems for knee arthroplasty disclosed herein include implants (e.g., tibial implants, femoral implant, patella implants), installation or arthroplasty tools for installing the implants; and position verification systems for determining and verifying the position of the implants relative to the bone. The different methods for knee arthroplasty disclosed herein include methods for installing implants and methods for verifying the position of an installed implant relative to the bone.

Figure 1:
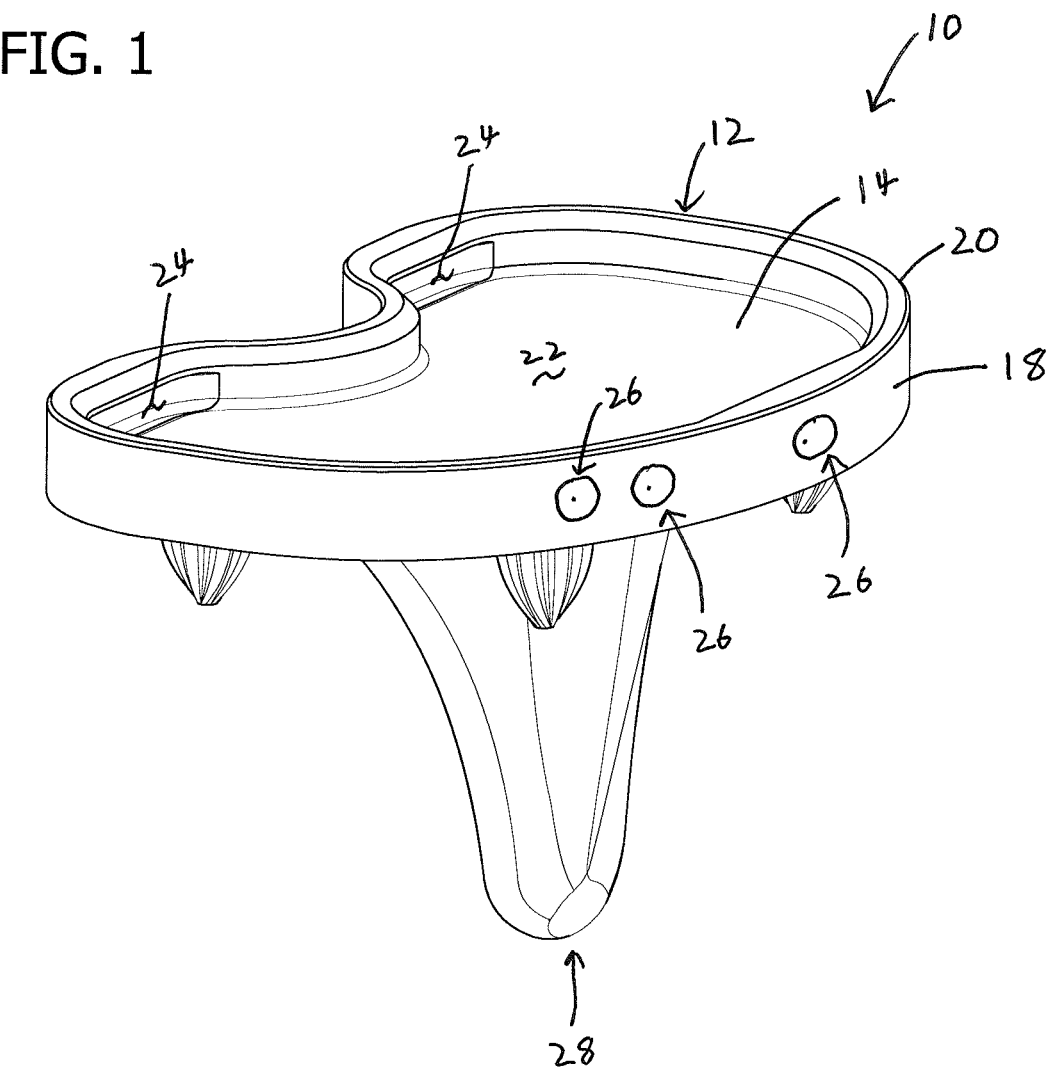
FIG. 1 is a front perspective of a tibial implant according to one embodiment of the present disclosure.
Figure 2:
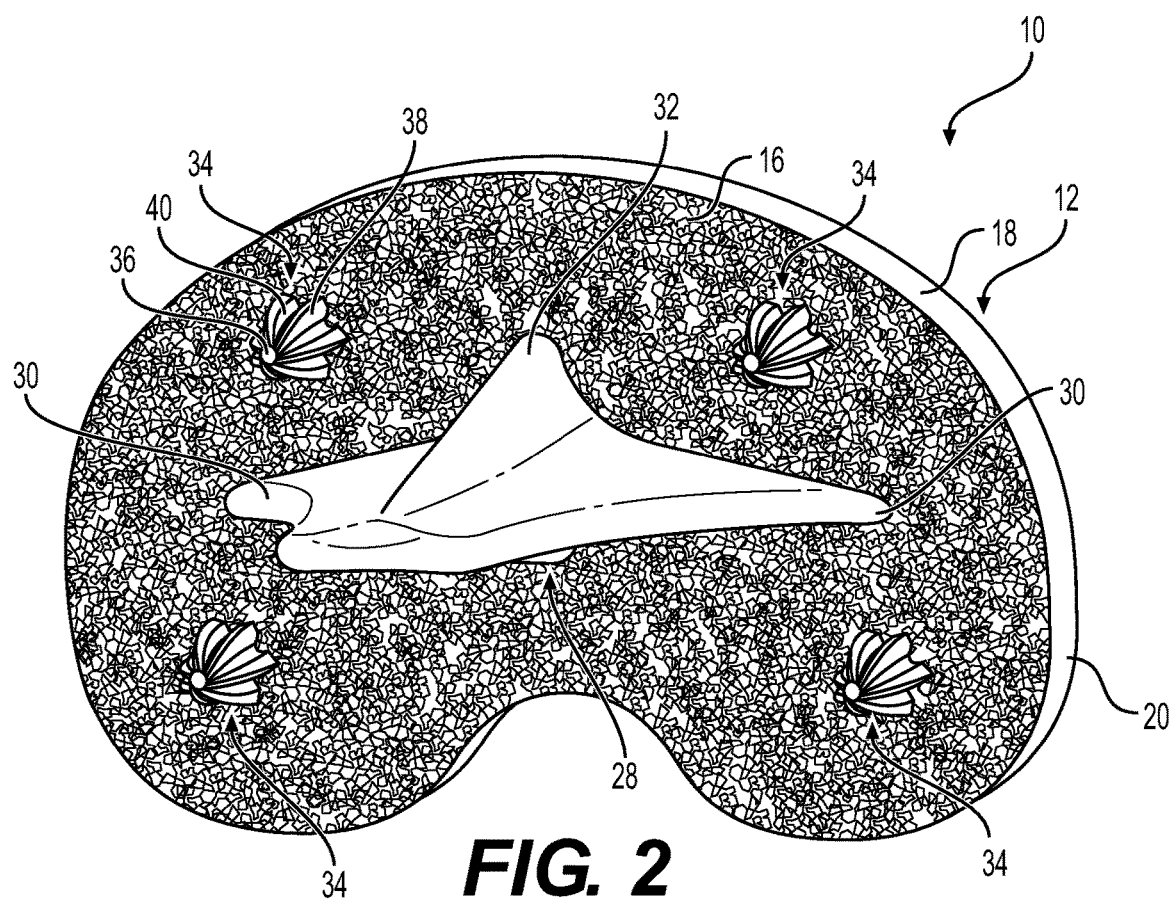
FIG. 2 is a bottom perspective of the tibial implant of FIG. 1.
Figure 3:
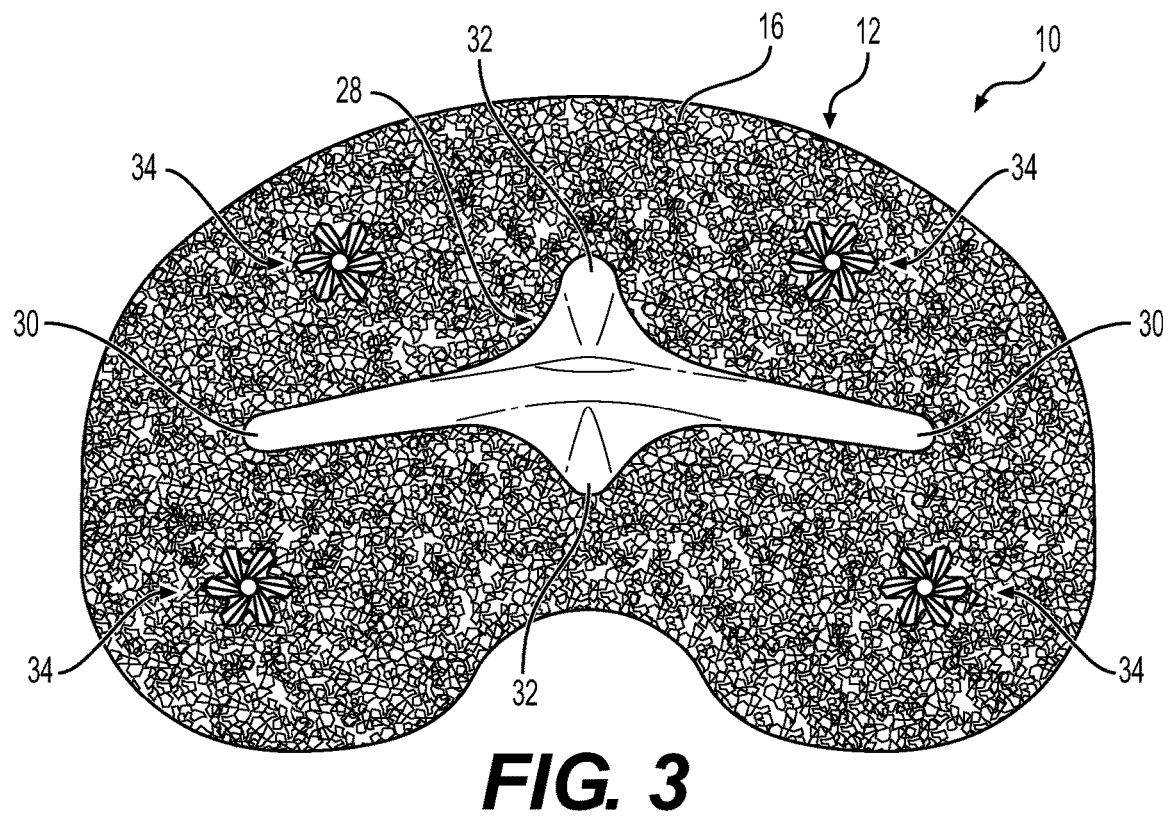
FIG. 3 is a bottom plan view of the tibial implant of FIG. 1.
Figure 18:
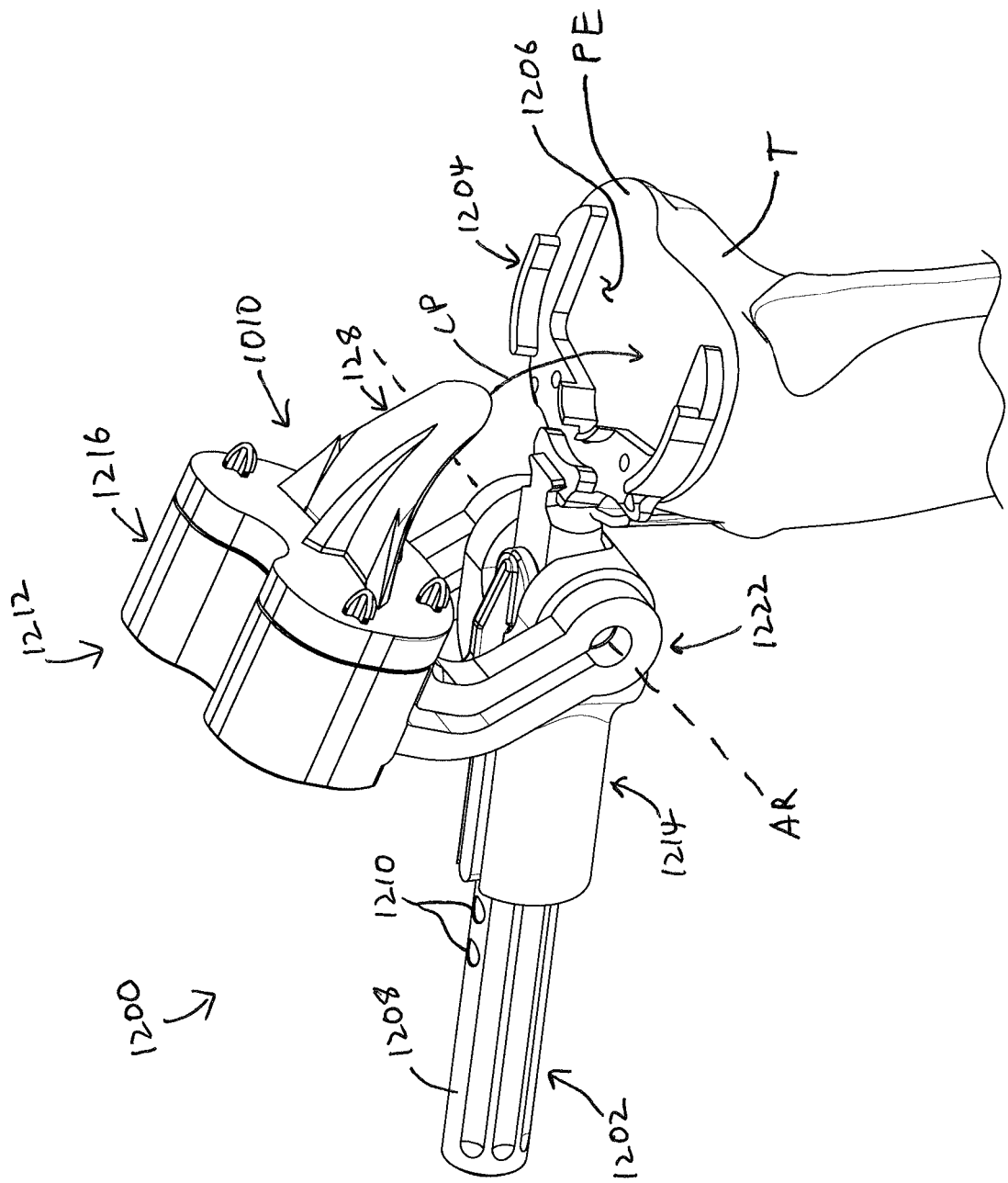
FIG. 18 is a perspective of an installation tool assembly installing the tibial implant of FIG. 16 on the proximal end of a tibia of a patient.

Referring to FIGS. 1-3, one embodiment of a tibial tray or implant for knee arthroplasty according to one embodiment of the present disclosure is generally indicated at reference numeral 10. The tibial implant 10 includes a tibial plate 12 sized and shaped for placement on a proximal end PE of a tibia T of a patient (FIG. 18). The tibial plate 12 can have generally any size and shape to match the particular size and shape of the proximal end PE of the tibia T the tibial implant is attached to. The tibial plate 12 includes opposite proximal and distal surfaces 14, 16. The distal surface 16 of the tibial plate 12 is configured to engage the proximal end PE of the tibia T. The tibial plate 12 has a perimeter edge margin 18. In the illustrated embodiment, the tibial plate 12 includes a perimeter wall 20 extending proximally from the proximal surface 14. The perimeter wall 20 includes the perimeter edge margin 18. The perimeter wall 20 defines an insert receiving space 22 sized and shaped to receive an insert (not shown). The perimeter wall 20 may include one or more recesses or notches 24 used to receive a portion of the insert to hold the insert in the insert receiving space 22. The proximal surface 14 defines the distal or bottom end of the insert receiving space 22.

The tibial implant 10 may include at least one (e.g., a plurality of) positioning guides 26 configured to be engaged by a position verification system 1400 (FIG. 26), as discussed in more detail below, to verify the position of the tibial implant relative to the proximal end PE of the tibia T after the tibial implant is implanted (e.g., placed) on the proximal end of the tibia. The positioning guides 26 are used to locate or register the position verification system 1400 relative to the tibial implant 10, as discussed in more detail below. The positioning guides 26 are sized and shaped to mate with an element or component (e.g., position indicator 1402) of the position verification system 1400. Thus, the positioning guides 26 are touch points for the position verification system 1400. The one or more positioning guides 26 are disposed on the tibial implant 10 in positions that will be accessible after the implant is attached to the tibia T. In the illustrated embodiment, the positioning guides 26 are disposed on the tibial plate 12. Specifically, the positioning guides 26 are disposed on the perimeter edge margin 18 of the tibial plate 12 and, desirably on a forward portion of the perimeter edge margin so that the positioning guides are easily accessible after the tibial implant 10 is implanted. Other positions of the positioning guides 26 are within the scope of the present disclosure. For example, the positioning guides 26 may be disposed on the proximal surface 14. The positioning guides 26 may be positive elements, such as projections, or negative elements, such as depressions. In the illustrated embodiment, the positioning guides 26 are depressions or recesses. Thus, the positioning guides 26 of the illustrated embodiment are configured to receive or be engaged by the position verification system 1400. The recesses 26 may have generally any shape such as, but not limited to, a conical shape (e.g., an inverted cone) as shown in FIG. 1, a conical shape with a flat bottom, a partially spherical shaper, a semi-spherical shape, a cylindrical shape, a rectangular shape, a square shape, a pyramidal shape, etc. The positioning guides 26 are spaced apart from one another. In one embodiment, the positioning guides 26 are configured to indicate identification data of the tibial implant 10 such as, but not limited to, the size of the tibial implant, the part number of the implant, etc. The position of the positioning guides 26 on the tibial implant 10 and/or distance between the positioning guides can be used to indicate or encode the identification data. When the position verification system 1400 registers with the positioning guides 26, the system can match the position of the positioning guides and/or the distance between the positioning guides to an implant database containing a list of possible implants to determine the specific type of tibial implant 10 and/or confirm that the correct tibial implant has been implanted on the tibia T. For example, the distance between the positioning guides 26 can represent (e.g., encode) the size of the tibial implant 10 (e.g., the spacing between positioning guides 26 varies by the size of the implant) and the position verification system 1400 can determine the size of the implant tibial implant by referencing the implant database to confirm the correct size of tibial implant was implanted.

The tibial implant 10 includes a tibial stem or keel 28. The tibial keel 28 is configured to be inserted into the proximal end PE of the tibia T. The tibial keel 28 is attached to the tibial plate 12. The tibial keel 28 extends generally distally from the distal surface 16 of the tibial plate 12. In the illustrated embodiment, the tibial keel 28 is generally straight. The tibial keel 28 may be solid or hollow (e.g., have a solid or hollow core). The tibial keel 28 may include coronal fins 30 (e.g., two coronal fins). The coronal fins 30 extend outward from the center of the tibial keel 28 in a direction that is generally parallel to a coronal plane of the patient (e.g., a vertical side-to-side extending plane). In the illustrated embodiment, the coronal fins 30 are at a slight angle relative to the coronal plane, such as about 15 degrees or less to form a slight V-shape. The tibial keel 28 may also include sagittal fins 32 (e.g., two sagittal fins). The sagittal fins 32 extend outward from the center of the tibial keel 28 in a direction that is generally parallel to a sagittal plane of the patient (e.g., a vertical front-to-rear extending plane). The coronal fins 30 and the sagittal fins 32 taper inwardly as the fins extend distally. The width of the sagittal fins 32 may also taper inwardly (e.g., in a direction generally parallel to the coronal plane) as the fins extend distally. The fins 30, 32 have rounded edges. The nose or tip of the tibial keel 28 is tapered (e.g., curved) in the coronal plane. In other embodiments, the nose of the tibial keel 28 may also be tapered in the sagittal plane. Other configurations of the tibial keel are within the scope of the present disclosure, some of which are disclosed herein.

Referring to FIGS. 2 and 3, the tibial implant 10 may include at least one anchoring projection 34. In the illustrated embodiment, the tibial implant 10 includes four anchoring projections 34, although more or fewer anchoring projections are within the scope of the present disclosure. The anchoring projections 34 are spaced apart from one another over the distal surface 16 of the tibial plate 12. In the illustrated embodiment, the four anchoring projections 34 are arranged in generally an X-arrangement about the tibial keel 28, with the tibial keel at the center of the X. Other arrangements of the anchoring projections 34 are within the scope of the present disclosure.

Each anchoring projection 34 is configured to be inserted into the proximal end PE of the tibia T. Each anchoring projection 34 is generally identical and thus, one anchoring projections will be described in further detail with the understanding the other anchoring projections have essentially the same construction (e.g., are disposed at different locations on the tibial plate 12). The anchoring projection 34 is attached to the tibial plate 12. The anchoring projection 34 extends generally distally from the distal surface 16 of the tibial plate 12. The anchoring projection 34 has a distal end or tip 36. In this embodiment, the distal tip 36 includes a recess. The recess may have generally any shape such as, but not limited to, a conical shape (e.g., an inverted cone), although other shapes are within the scope of the present disclosure, such as a conical shape with a flat bottom, a partially spherical shaper, a semi-spherical shape, a cylindrical shape, a rectangular shape, a square shape, a pyramidal shape, etc. The recess maximizes the press fit of the anchoring projection 34 with the bone when the tibial implant 10 is implanted into the tibia T to increase the compression between the anchoring projection and the bone to stimulate healing of the bone. In addition, the recess facilitates the formation of a sharp, leading distal edge at the distal tip 36 to facilitate the insertion of the anchoring projection 34 into the proximal end PE of the tibia T. In the illustrated embodiment, the anchoring projection 34 has a generally rounded, conical shape (e.g., a bullet shape), although other shapes such as rounded, blade or hollow shaped are within the scope of the present disclosure. The anchoring projection 34 includes a plurality of ribs 38 that extend proximally from the distal tip 36. The ribs 38 extend proximally to the distal surface 16 of the tibial plate 12. In the illustrated embodiment, the anchoring projection 34 includes six ribs 38, although more (e.g., 20) or fewer (e.g., 4) ribs are within the scope of the present disclosure. The ribs 38 are circumferentially disposed about the anchoring projection 34. The ribs 38 have beveled edges, but in other embodiments can have rounded, chamfered, sharp, fillet, etc. edges. In this embodiment, the ribs 38 curve (e.g., slightly curve) about a longitudinal axis of the anchoring projection 34. The longitudinal axis extends proximally and distally through the distal tip 36 of the anchoring projection 34. In other words, the ribs 38 curve helically or partially helically about the longitudinal axis. In the illustrated embodiment, each rib 38 includes a proximal portion extending generally distally straight from the distal surface 16 and a distal portion extending distally in a curved manner, about the longitudinal axis, from the proximal portion to the distal tip 36. The ribs 38 taper inward (e.g., toward the longitudinal axis) toward the distal tip 36 as the ribs extend distally. The taper may be straight or curved. Other configurations of the ribs 38 are within the scope of the present disclosure. Adjacent ribs 38 define a groove 40 therebetween. The groove 40 extends from the distal surface 16 to the distal tip 36 and the shape of the groove generally corresponds to the shape of the ribs 38. Accordingly, the groove 40 also curves about the longitudinal axis. The design of the ribs 38 (broadly, anchoring projection 34) minimizes bone displacement, minimizes risk of fracture and increases the surface area of the anchoring projection for bone ingrowth. Other configurations of the anchoring projection are within the scope of the present disclosure, some of which are disclosed herein. The anchoring projection 34 may be solid or hollow (e.g., have a solid or hollow core).

Figure 25:
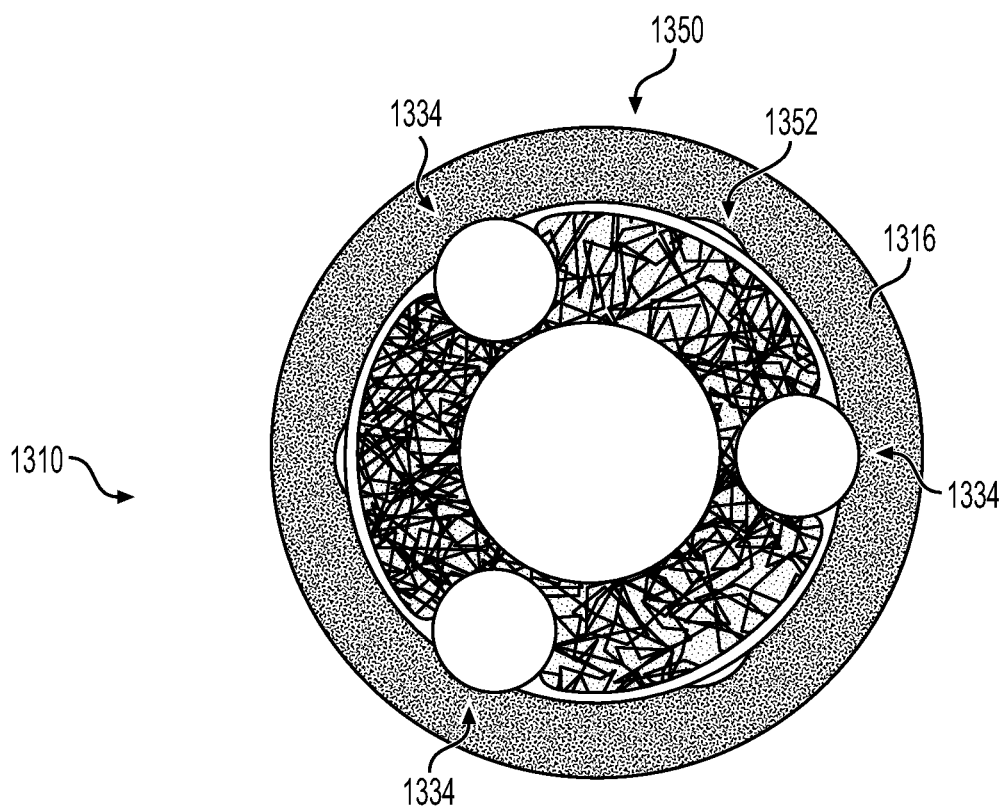
FIG. 25 is a bottom plan view of the patella implant.

The tibial implant 10 may include one or more porous regions. The porous regions are disposed at positions on the tibial implant that engage the tibia T (broadly, bone). The porous regions enable ingrowth of the bone into the tibial implant 10 after the tibial implant is placed on the bone to form a strong connection between the implant and the bone. This allows the tibial implant 10 to be inserted into the tibia T without the cement conventionally used in knee arthroplasties, reducing procedural times, cement related complications and surgeon stress. The porous regions may have a porosity within the inclusive range of about 40%-90%, or more preferably within the inclusive range of about 50%-80%. The porous regions may have a thickness of about 1 mm to 1.5 mm. In the illustrated embodiment, the distal surface 16 of the tibial plate 12 is porous (e.g., is a porous region). Other parts of the tibial implant 10 may include porous regions. For example, in one embodiment, at least a portion of tibial keel 28 and/or anchoring projection(s) 34 is porous to enable ingrowth of bone into the tibial keel and/or anchoring projection(s) 34, respectively, after the tibial implant 10 is inserted into or implanted on the proximal end PE of the tibia T. Any surface of the tibial keel 28 and anchoring projection(s) 34 may be porous. Preferably, the porous regions extend distally along the tibial keel 28 and anchoring projection(s) 34 from the distal surface 16 of the tibial plate 12. Preferably, the porous regions of the tibial keel 28 and/or anchoring projection(s) 34 extend distally from the distal surface 16 over a distance up to and including about 10 mm. This allows the bone to grow into the tibial keel 28 and/or anchoring projection(s) 34 while still allowing the tibial implant 10 to be easily removed in the future should adjustment or replacement of the implant be required. The porous regions of the tibial keel 28 and/or anchoring projection(s) 34 can extend over (e.g., cover) more of the tibial keel and/or anchoring projection(s) 34, including the entirety thereof, to enable a stronger connection to be formed between the tibial keel and/or anchoring projection(s) 34 but it will be more difficult to remove and replace such a tibial implant from the bone, if removal is ever needed. In one embodiment, the porous regions comprise hexagonal struts coupled together to form a lattice (FIGS. 2 and 25), although any suitable porous structure is within the scope of the present disclosure.

The tibial implant 10 can be made using conventional manufacturing processes and methods and/or additive manufacturing processes and methods (e.g., three-dimensional (3D) printing). In one method of manufacture, the entire tibial implant 10 is constructed using additive manufacturing. In this method, the tibial implant 10 is built by an additive manufacturing machine (e.g., a 3D printer) which generally constructs the implant on a base plate and post processes the implant before the implant is removed from the base plate. In another method of manufacture, the tibial implant 10 is constructed using hybrid manufacturing, which combines conventional manufacturing methods with additive manufacturing. In this hybrid method, the tibial plate 12 of the implant 10 can first be created by conventional manufacturing methods, such as cold forming (e.g., stamping, cutting, deforming) a metal blank or by forging the tibial plate. The tibial plate 12 is then placed in an additive manufacturing machine which builds the additional elements (e.g., keel 28, anchoring projection(s) 34, porous regions, etc.) on the tibial plate. Preferably, the porous regions of the tibial implant 10 are constructed using additive manufacturing. The additive manufacturing machine builds (e.g., is configured to build) the porous regions (e.g., the lattice of hexagonal struts) on the components (e.g., tibial plate 12) of the tibial implant. Additive manufacturing enables more complex porous structures to be built than possible with conventional methods. For example, conventional manufacturing methods cannot construct the porous regions comprised of a lattice of hexagonal struts. Various different additive manufacturing processes may be used to create the porous regions such as 3D printing, direct metal laser sintering (DMLS), titanium deposition spray, etc. Other methods of constructing the porous regions are within the scope of the present disclosure. For example, porous regions can be constructed using a subtractive manufacturing process such as laser etching or acid etching.

Other configurations of the tibial implant are within the scope of the present disclosure. For example, the tibial implant can have one or more of the tibial keels and/or anchoring projections described below.

Figure 4:
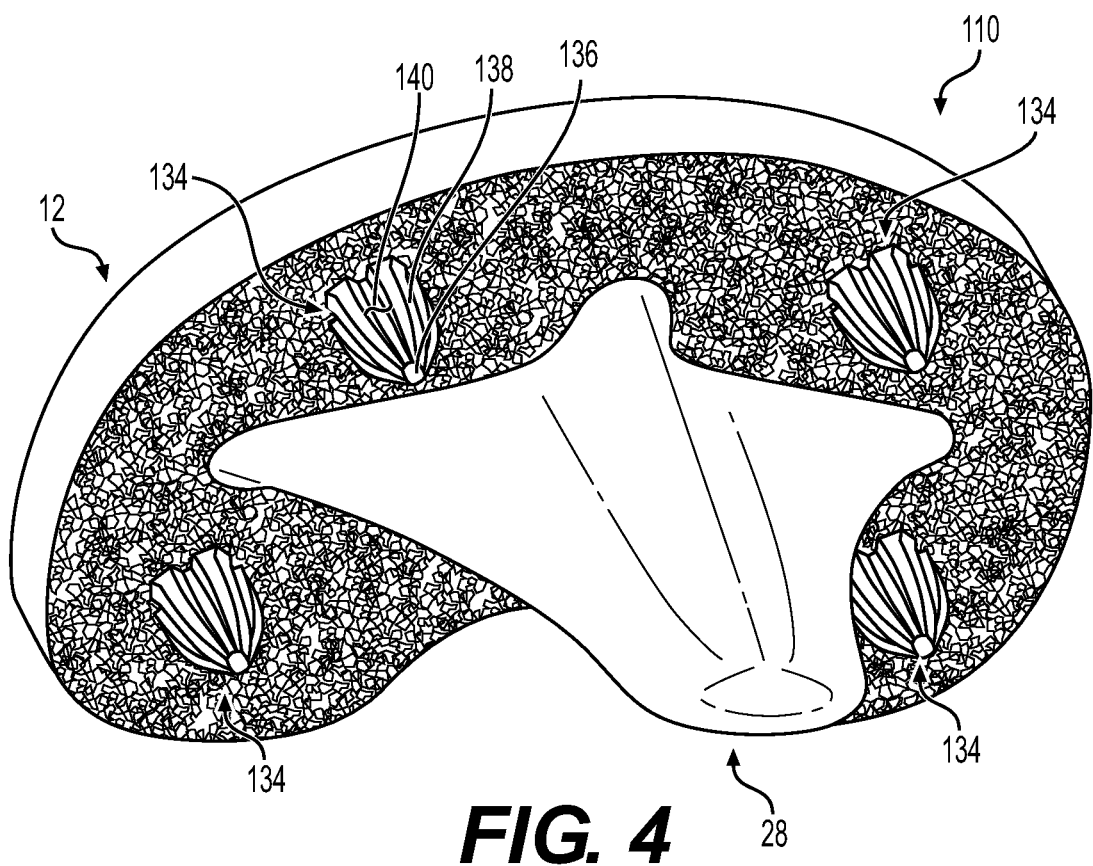
FIG. 4 is a bottom perspective of a tibial implant according to another embodiment of the present disclosure.

Referring to FIG. 4, an anchoring projection for a tibial implant 110 according to another embodiment of the present disclosure is generally indicated at reference numeral 134. In this embodiment, the ribs 138 of the anchoring projection 134 are generally straight and extend parallel to and toward the longitudinal axis (e.g., do not curve about the longitudinal axis). In this embodiment, the distal tip 136 of the anchoring projection 134 includes a point (e.g., a conical shaped point).

Figure 5:
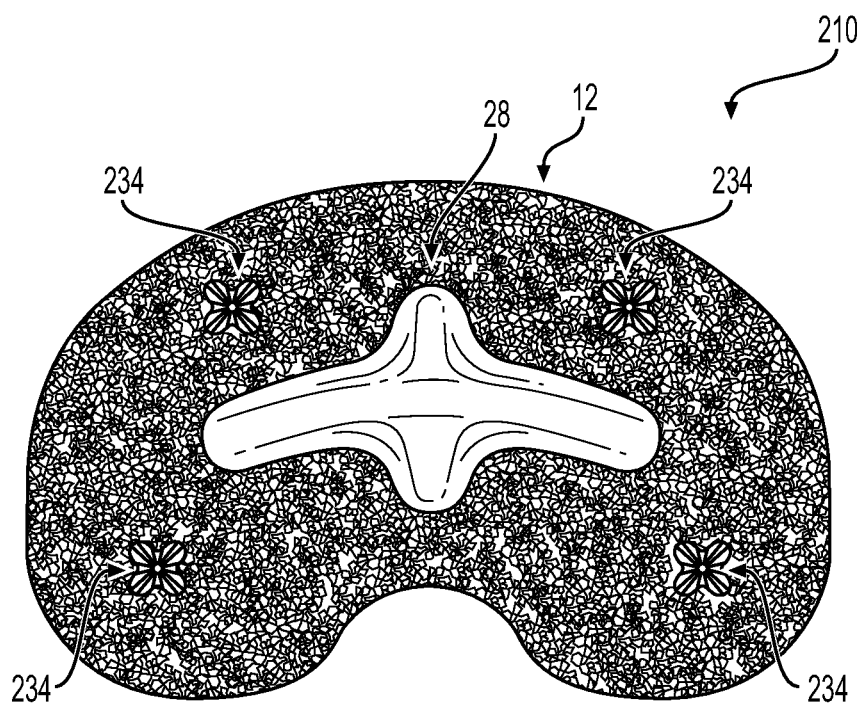
FIG. 5 is a bottom plan view of a tibial implant according to another embodiment of the present disclosure.
Figure 6:
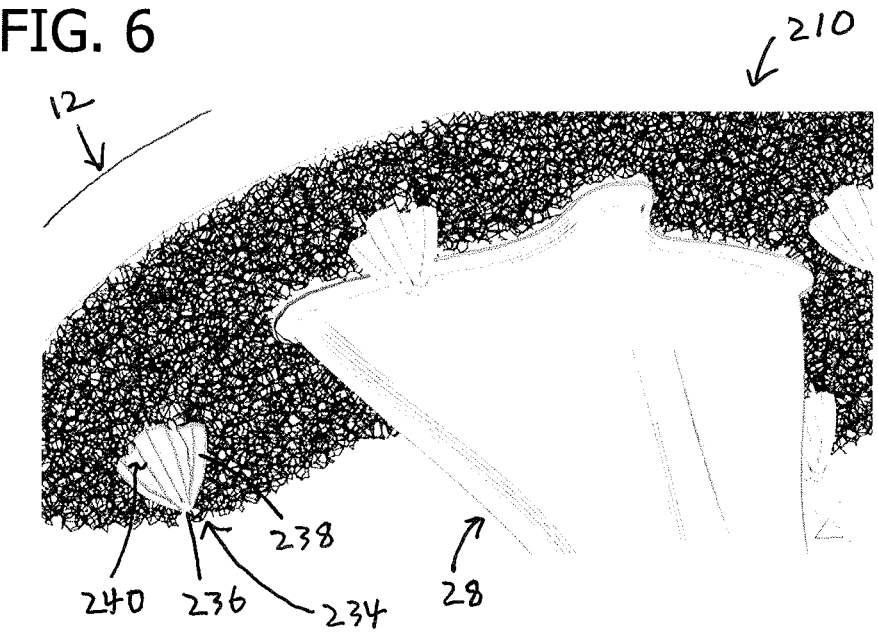
FIG. 6 is an enlarged, fragmentary bottom perspective a tibial implant of FIG. 5.

Referring to FIGS. 5 and 6, an anchoring projection for a tibial implant 210 according to another embodiment of the present disclosure is generally indicated at reference numeral 234. In this embodiment, the anchoring projection 234 includes four ribs 238, which are arranged in generally an X-shape (FIG. 5). The ribs 238 are also generally straight and extend parallel to and toward the longitudinal axis. The distal tip 236 also includes a point, similar to anchoring projection 134. In this embodiment, the ribs 238 are spaced apart from the distal surface 16 of the tibial plate 12. The ribs 238 extend proximally from the distal tip 236 to a location intermediate of the distal tip and the distal surface 16. Each rib 238 includes a proximal surface that faces and is spaced apart from the distal surface 16. Together, the proximal surface of the ribs 238, the distal surface 16 of the tibial plate 12 and a base (not shown) of the rib define a space for the bone (e.g., tibia T) to grow into and surround the ribs. In other embodiments, the ribs 238 may extend all the way to the distal surface 16, such as ribs of the anchoring projections 234A in FIGS. 16, 17, 21 and 22.

Figure 7:
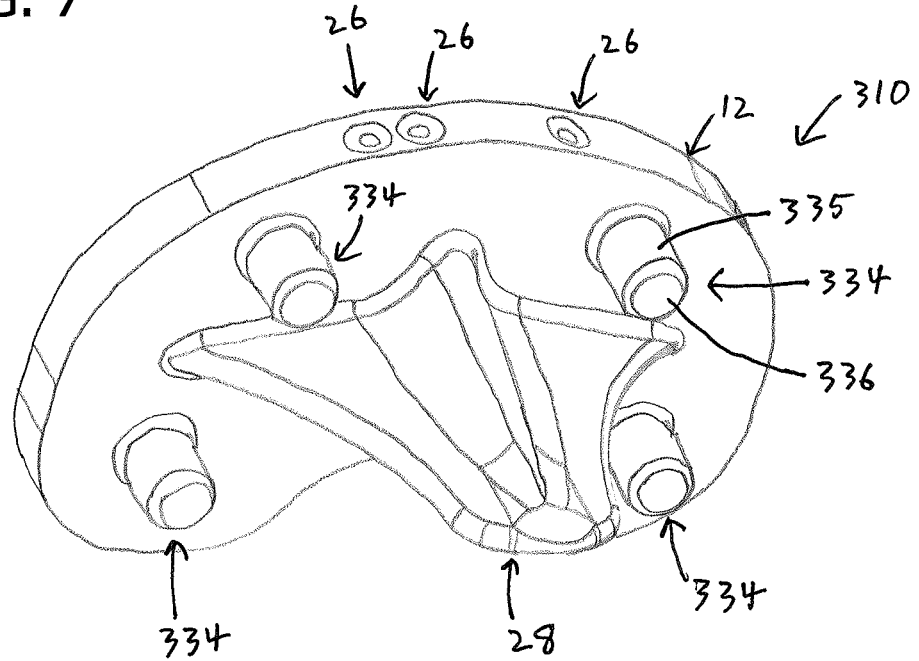
FIG. 7 is a bottom perspective of a tibial implant according to another embodiment of the present disclosure.

Referring to FIG. 7, an anchoring projection for a tibial implant 310 according to another embodiment of the present disclosure is generally indicated at reference numeral 334. In this embodiment, the anchoring projection 334 is cylindrical (e.g., has a cylinder shape). The anchoring projection 334 includes a cylindrical outer surface 335 and a leading or distal surface 336. The distal surface is generally planar (e.g., the distal end 336 is generally blunt) and has a circular shape. The edge or corner between the outer surface 335 and the distal surface 336 is rounded, but in other embodiments can have beveled, chamfered, sharp, fillet, etc.

Figure 8:
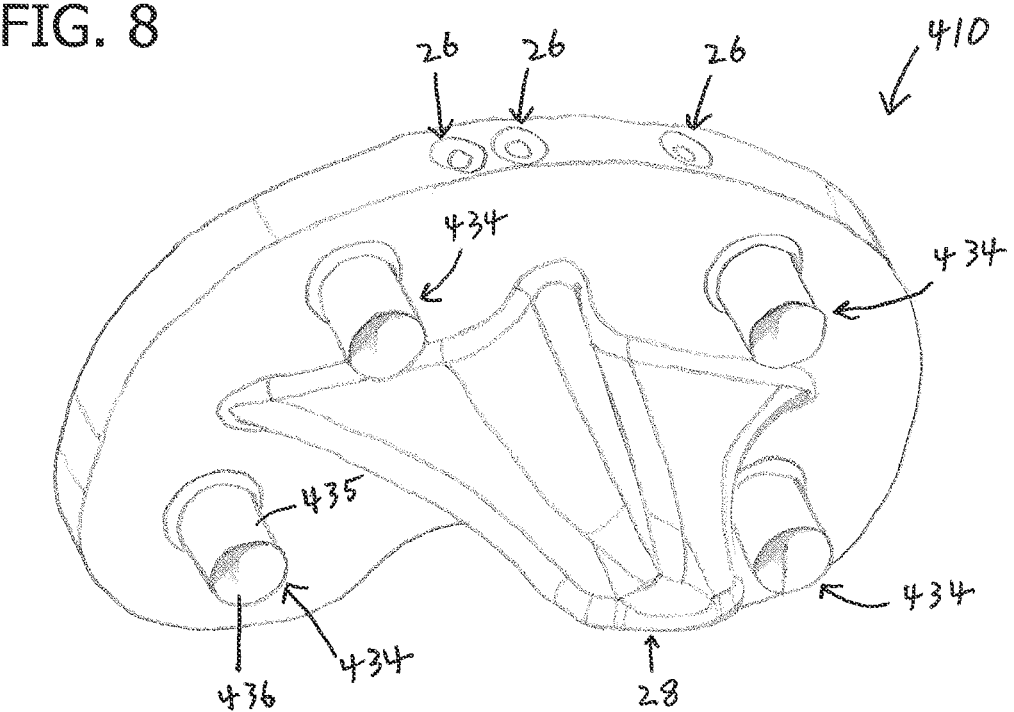
FIG. 8 is a bottom perspective of a tibial implant according to another embodiment of the present disclosure.

Referring to FIG. 8, an anchoring projection for a tibial implant 410 according to another embodiment of the present disclosure is generally indicated at reference numeral 434. In this embodiment, the anchoring projection 434 is generally cylindrical with a cylindrical outer surface 435. The distal end 436 includes a recess which, in the illustrated embodiment, is an inverted cone, although other configurations as described herein are within the scope of the present disclosure. In this embodiment, the width or diameter of the base of the inverted cone recess at the distal end 436 is generally equal to the width or diameter of the cylindrical outer surface 435, although the base of the recess having a smaller width is within the scope of the present disclosure. The anchoring projection 434 includes a sharp leading or distal edge at the distal end 436 between the recess at the distal end 436 and the cylindrical outer surface 436.

Figure 9:
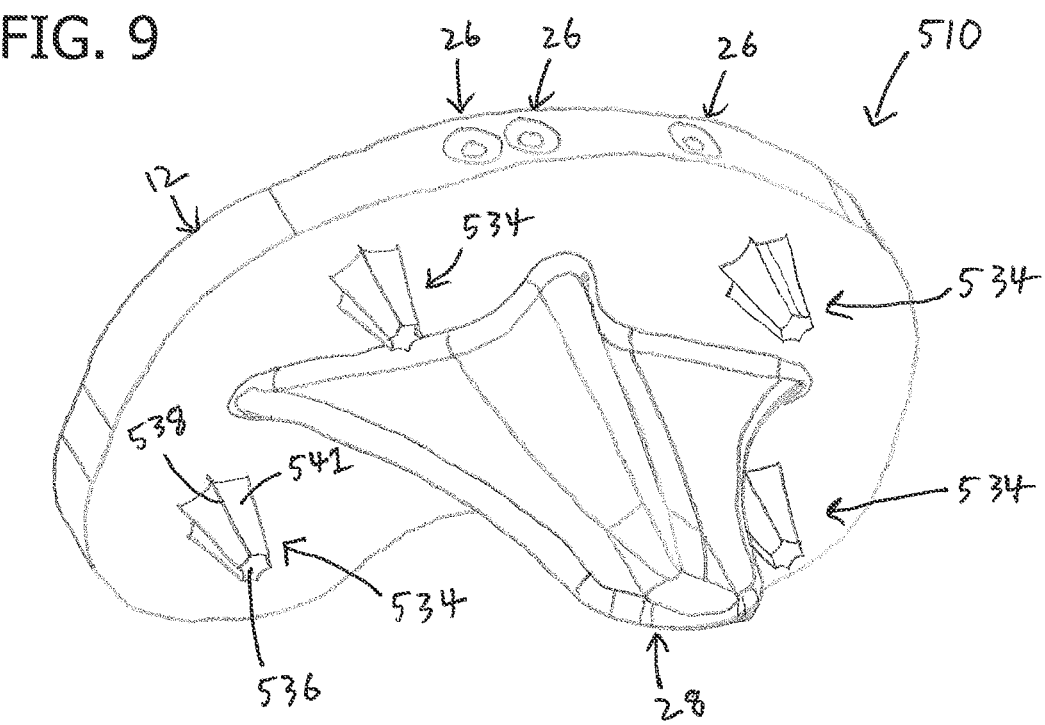
FIG. 9 is a bottom perspective of a tibial implant according to another embodiment of the present disclosure.

Referring to FIG. 9, an anchoring projection for a tibial implant 510 according to another embodiment of the present disclosure is generally indicated at reference numeral 534. In this embodiment, the anchoring projection 534 has a generally polygonal (e.g., hexagonal) shape that tapers inward as the anchoring projection extends distally. The surfaces 541 of the polygonal shape are concave. As a result, the edges between the surfaces generally define spines 538 of the anchoring projection 534 with a sharp edge. In this embodiment, the distal end 536 has a generally planar distal surface.

Figure 10:
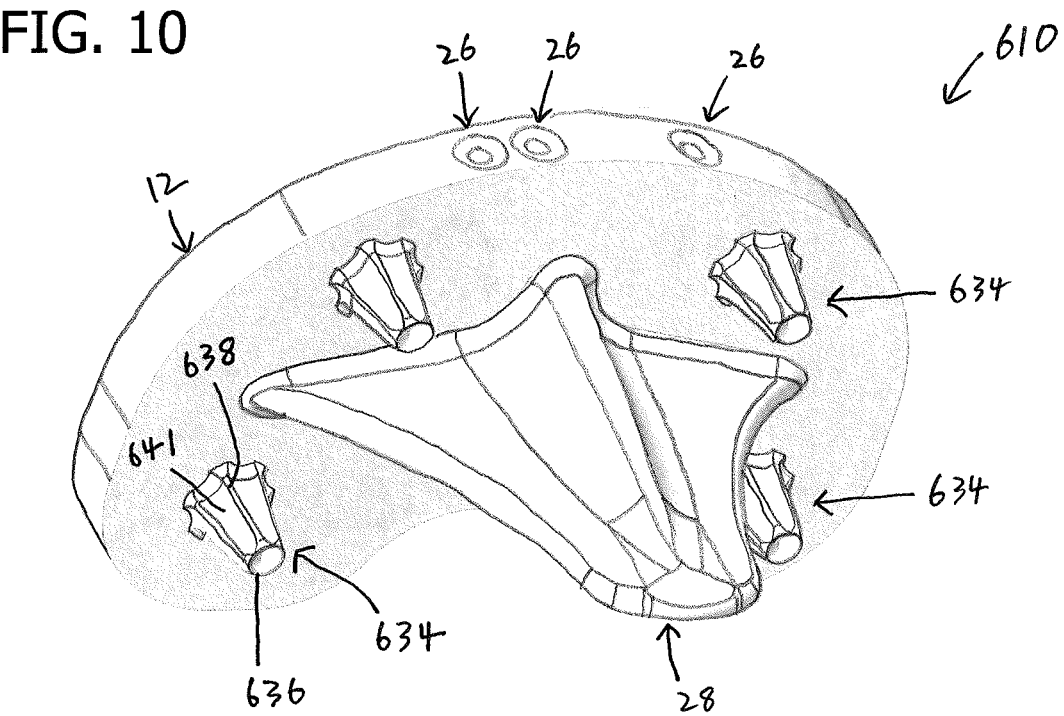
FIG. 10 is a bottom perspective of a tibial implant according to another embodiment of the present disclosure.

Referring to FIG. 10, an anchoring projection for a tibial implant 610 according to another embodiment of the present disclosure is generally indicated at reference numeral 634. In this embodiment, the anchoring projection 634 has a generally polygonal (e.g., hexagonal) shape that tapers inward as the anchoring projection extends distally. The surfaces 641 of the polygonal shape are concave. As a result, the edges between the surfaces generally define spines 638 of the anchoring projection 634. In this embodiment, the spines 638 are rounded. The distal end 636 has a recess, such as an inverted cone.

Figure 11:
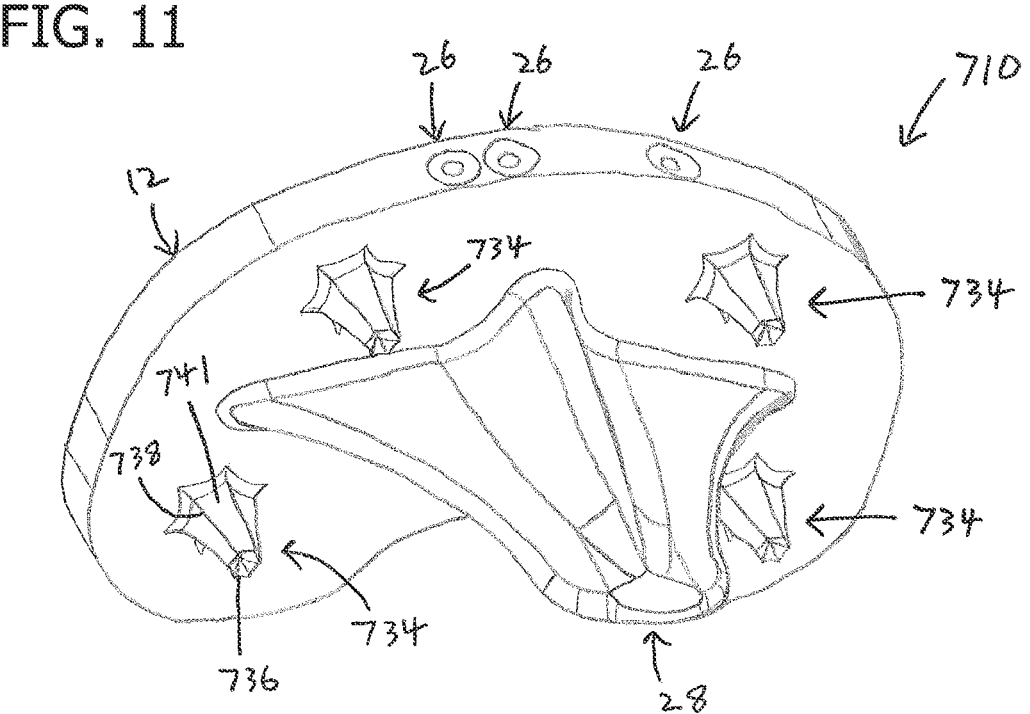
FIG. 11 is a bottom perspective of a tibial implant according to another embodiment of the present disclosure.
Figure 12:
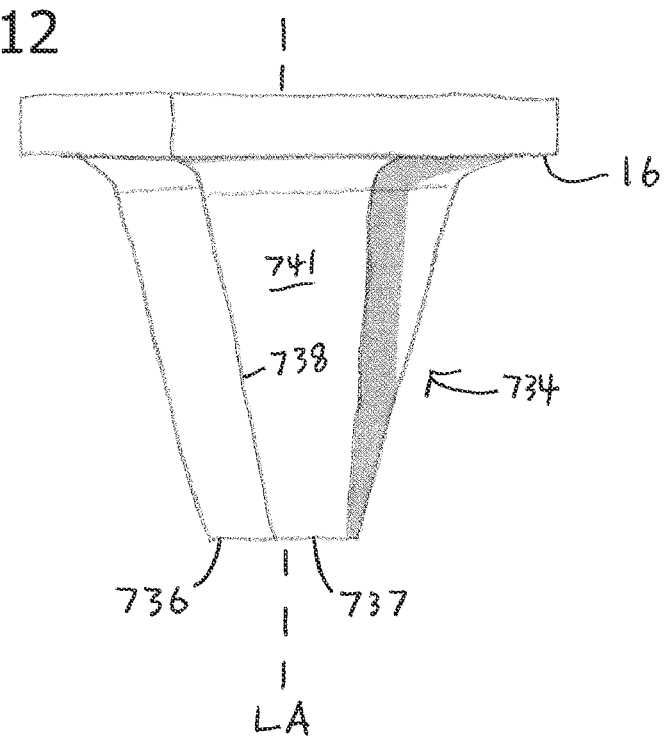
FIG. 12 is an enlarged, fragmentary side elevation of an anchoring projection of the tibial implant of FIG. 11.

Referring to FIGS. 11 and 12, an anchoring projection for a tibial implant 710 according to another embodiment of the present disclosure is generally indicated at reference numeral 734. In this embodiment, the anchoring projection 734 has a generally polygonal (e.g., hexagonal) shape that tapers inward as the anchoring projection extends distally. The surfaces 741 of the polygonal shape are concave. As a result, the edges between the surfaces 741 generally define spines 738 of the anchoring projection 734 with a sharp edge. The spines 738 generally curve about the longitudinal axis LA of the anchoring projection as the spines extend distally. Accordingly, the polygonal cross-sectional shape generally rotates about the longitudinal axis LA as the anchoring projection extends distally. The distal end 736 has a recess, such as an inverted hexagonal pyramid, although other shapes, such as those described herein, are within the scope of the present disclosure. The anchoring projection 734 includes a sharp leading or distal edge 737 at the distal end 736 between the recess at the distal end and the surfaces 741. The distal edge 737 has a polygonal (e.g., hexagonal) shape made out of a plurality of linear segments. The linear segments of the distal edge 737 are generally coplanar.

Figure 13:
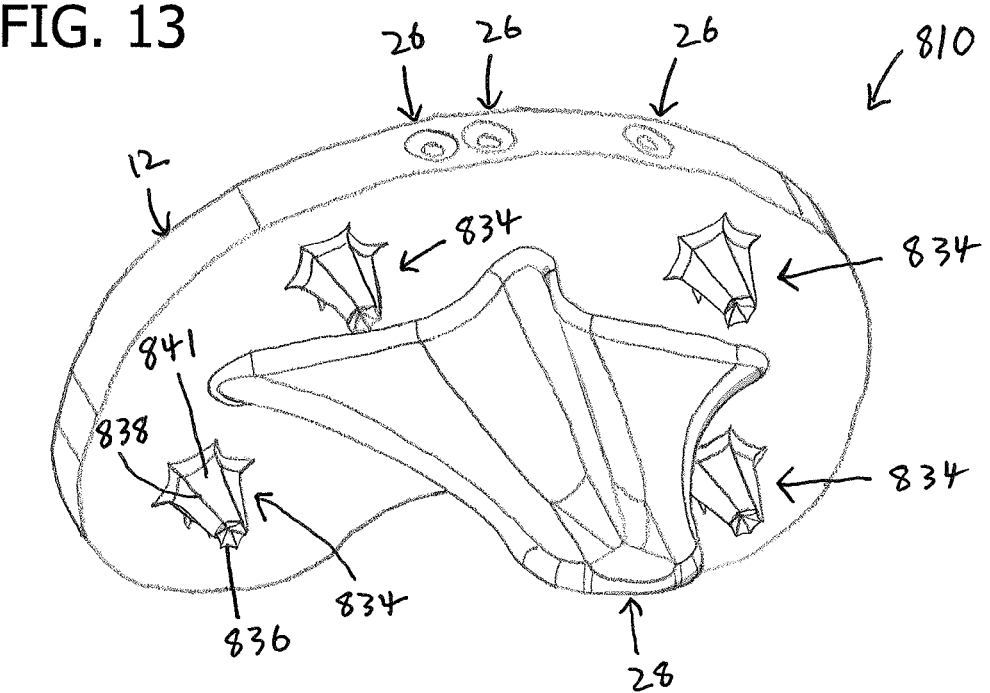
FIG. 13 is a bottom perspective of a tibial implant according to another embodiment of the present disclosure.
Figure 14:
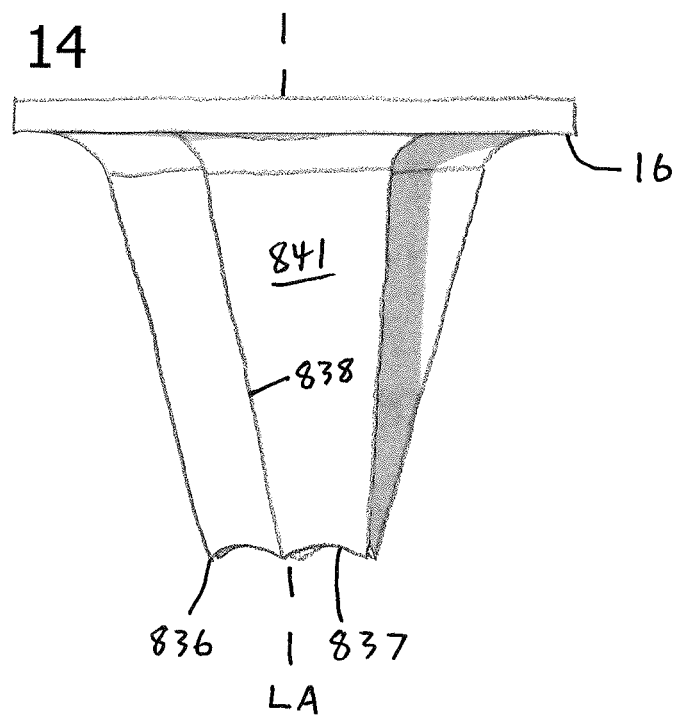
FIG. 14 is an enlarged, fragmentary side elevation of an anchoring projection of the tibial implant of FIG. 13.

Referring to FIGS. 13 and 14, an anchoring projection for a tibial implant 810 according to another embodiment of the present disclosure is generally indicated at reference numeral 834. In this embodiment, the anchoring projection 834 has a generally polygonal (e.g., hexagonal) shape that tapers inward as the anchoring projection extends distally. The surfaces 841 of the polygonal shape are concave. As a result, the edges between the surfaces 841 generally define spines 838 of the anchoring projection 834 with a sharp edge. The spines 838 generally curve about the longitudinal axis LA of the anchoring projection as the spines extend distally. Accordingly, the polygonal cross-sectional shape generally rotates about the longitudinal axis LA as the anchoring projection extends distally. The distal end 836 has a recess, such as an inverted hexagonal pyramid, although other shapes, such as those described herein, are within the scope of the present disclosure. The anchoring projection 834 includes a sharp leading or distal edge 837 at the distal end 836 between the recess at the distal end and the surfaces 841. The distal edge 837 has a generally polygonal (e.g., hexagonal) shape made out of a plurality of segments. In this embodiment, the line segments of the distal edge 837 are arcuate or curved (e.g., generally curved about an axis (e.g., horizontal axis) extending generally perpendicular to the longitudinal axis LA). As a result, the distal edge 837 has a generally saw-tooth configuration with a tooth or point being disposed at (e.g., defined by) the intersection of the two curved segments and a spine 838.

Figure 15:
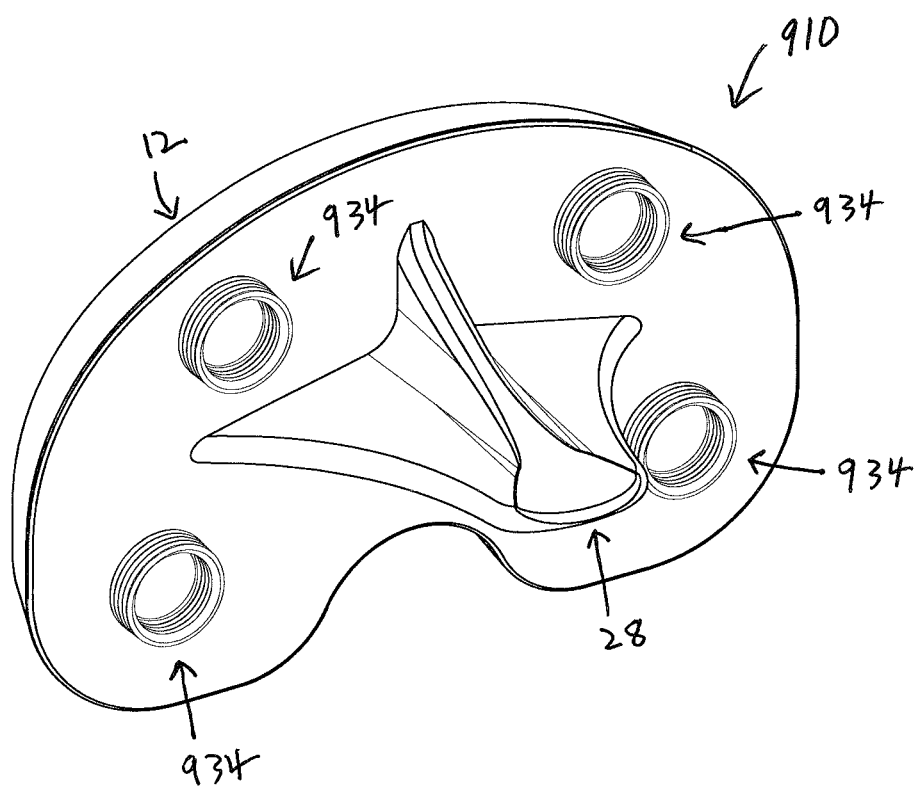
FIG. 15 is a bottom perspective of a tibial implant according to another embodiment of the present disclosure.
Figure 15A:
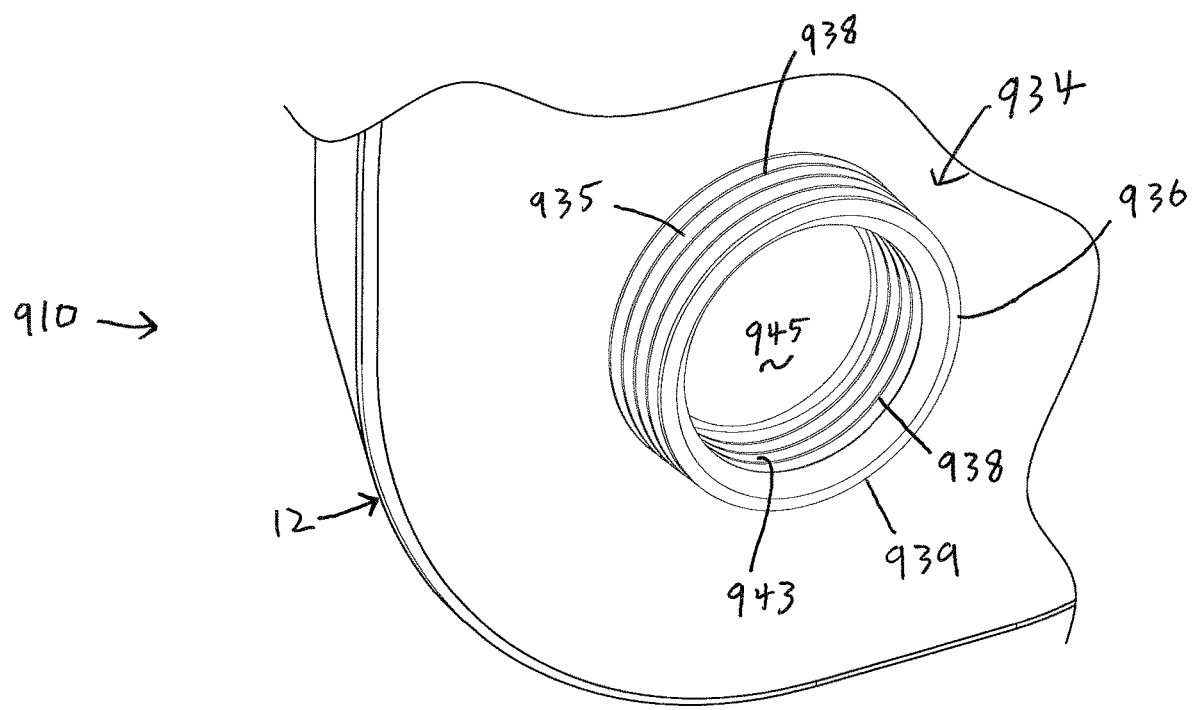
FIG. 15A is an enlarged, fragmentary bottom perspective of the tibial implant of FIG. 15.

Referring to FIGS. 15 and 15A, an anchoring projection for a tibial implant 910 according to another embodiment of the present disclosure is generally indicated at reference numeral 934. In this embodiment, the anchoring projection 934 includes a cylindrical wall 939 extending distally from the distal surface 16 to a distal end 936. The cylindrical wall 939 includes a generally cylindrical outer surface 935 and a generally cylindrical inner surface 943. The cylindrical inner surface 943 defines a cavity or recess 945 of the anchoring projection, similar in function to the other recesses of the anchoring projections described herein. The cavity 945 extends from the distal surface 16 to the distal end 936. The distal end 936 includes a generally planar distal surface. The inner and/or outer circumferential edge of the distal surface may be beveled, rounded, chamfered, sharp, fillet, etc. In the illustrated embodiment, the inner edge of the distal surface of the distal end 936 is beveled. The outer and inner surfaces 943, 934 each include one or more (e.g., a plurality of) circumferential spines 938 defined by circumferential, generally concave grooves extending into the cylindrical wall 939. The spines 938 are space apart longitudinally along cylindrical wall 939.

Figure 16:
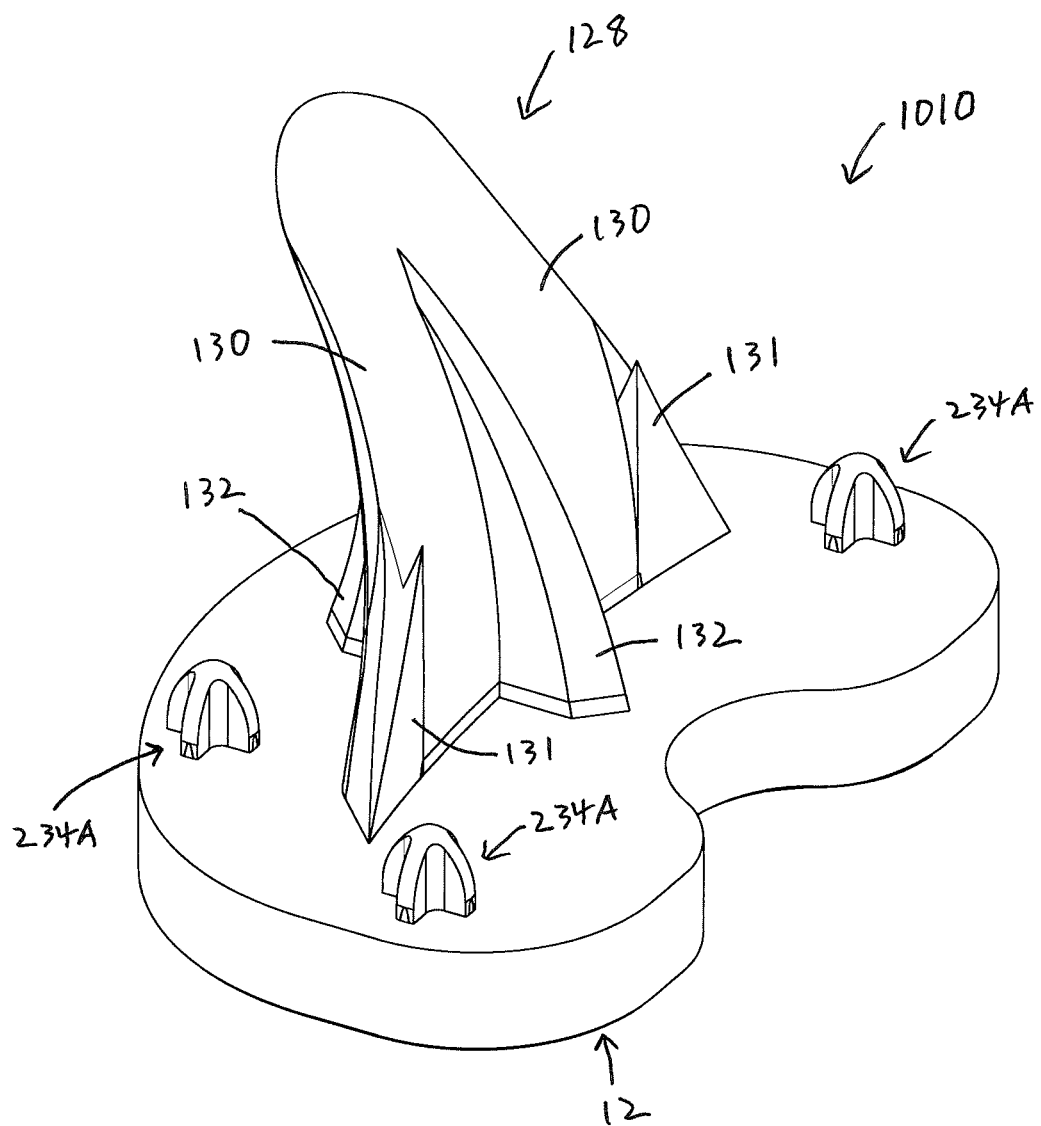
FIG. 16 is a front, bottom perspective of a tibial implant according to another embodiment of the present disclosure.
Figure 17:
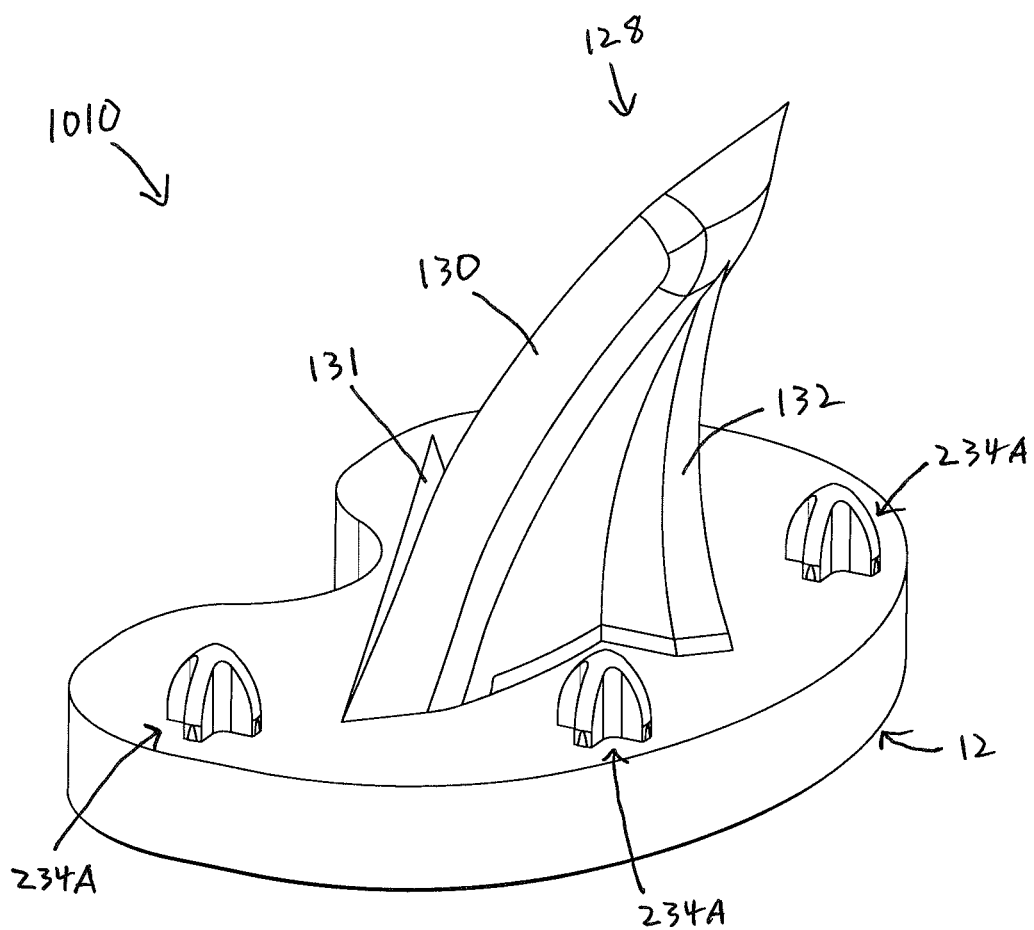
FIG. 17 is a rear, bottom perspective of a tibial implant of FIG. 16.

Referring to FIGS. 16 and 17, a tibial keel for a tibial implant 1010 according to another embodiment of the present disclosure is generally indicated at reference numeral 128. In this embodiment, the tibial keel 128 is arcuate or curved. The tibial keel 128 curves about a transverse axis of the patient (e.g., a lateral or side-to-side axis that is generally parallel to the distal surface 16 of the tibial plate 12) as the tibial keel extends distally from the distal surface of the tibial plate. In other words, the tibial keel 128 curves towards the front (e.g., in a forward direction) of the tibial implant 1010. As a result, the tibial keel 128 curves toward the tibial tubercle of the patient when the tibial implant 1010 is implanted on the tibia T. The tibial tubercle is a cortical prominence commonly used as a landmark in orthopedic surgery. Aiming the nose of the tibial keel 128 at the tibial tubercle ensures additional cortical purchase and reduces the chance of lift off by being disposed closer to the cortical bone, as opposed to other keel designs. In addition, the curved tibial keel 128 has a larger surface area than straight keel designs. The larger front or anterior surface and rear or posterior surface of the tibial keel 128 provides greater resistance to lift off of the tibial implant 10 from the tibia T. In addition, due to the curved design, a portion of the posterior surface of the tibial keel 128 faces distally, increasing the overall amount of distal facing surface area, which increases the ability of the tibial implant 1010 to resist subsidence. In addition to the tibial keel 128 being curved, the coronal and sagittal fins 130, 132 of the tibial keel include piercing edges. The edges of the fins 130, 132 may be tapered, sharp and/or serrated. Conventional insertion techniques require keel features to be drilled and/or broached into the tibia T before insertion the implant. The piercing edges of the tibial keel 128 facilitate insertion of the tibial implant 1010 without any or minimal prior bone preparation. In addition, in this embodiment, the tibial keel 128 also includes anchoring projections or spikes 131. The anchoring projections 131 are configured to be inserted into the proximal end PE of the tibia T to further secure the tibial implant 1010 to the tibia. In the illustrated embodiment, the anchoring projections 131 are disposed on the posterior side of the tibial keel 128, adjacent the edges of the coronal fins 130.

Figure 19:
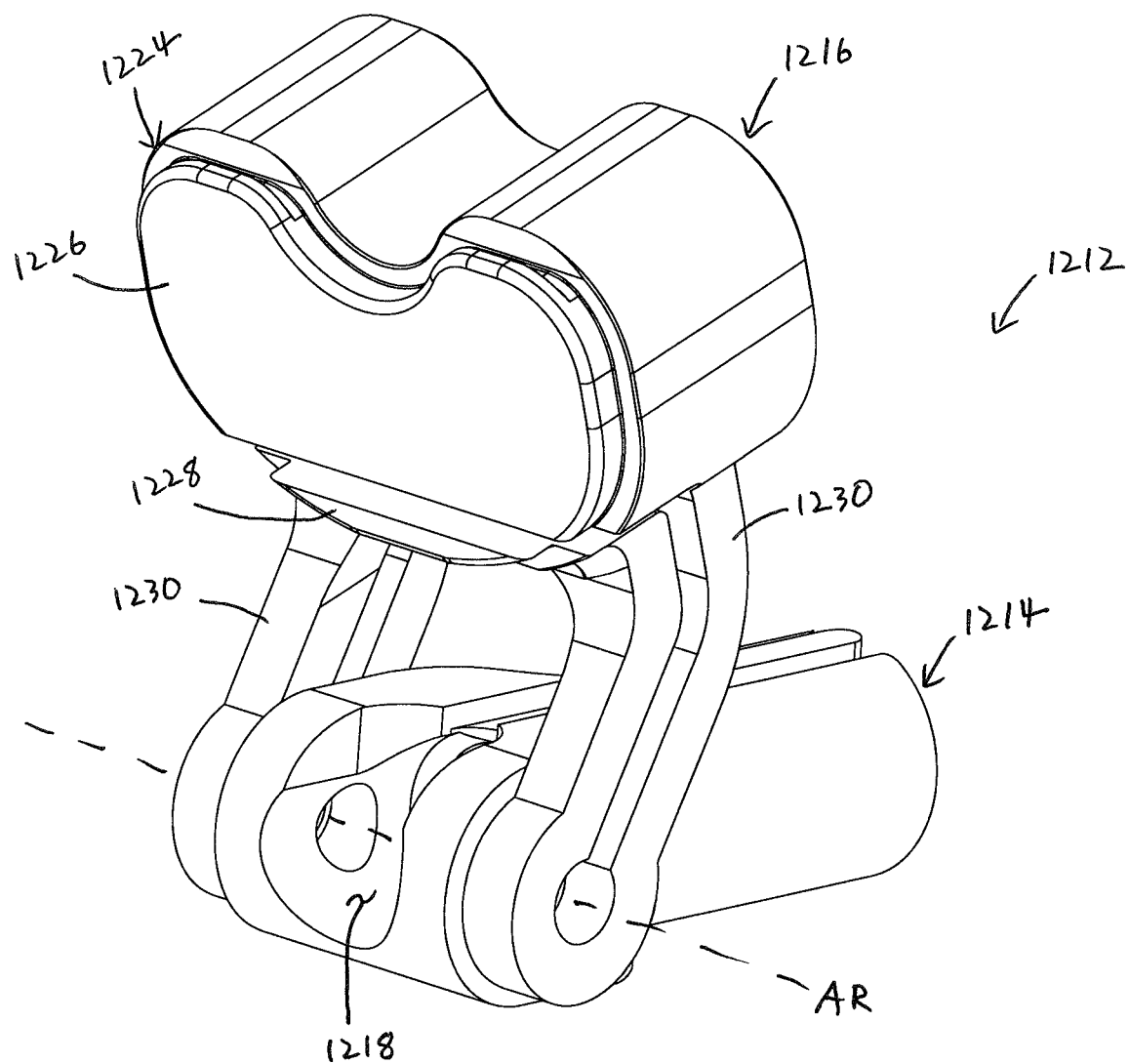
FIG. 19 is a front perspective of an impaction guide of the installation tool assembly.
Figure 20:
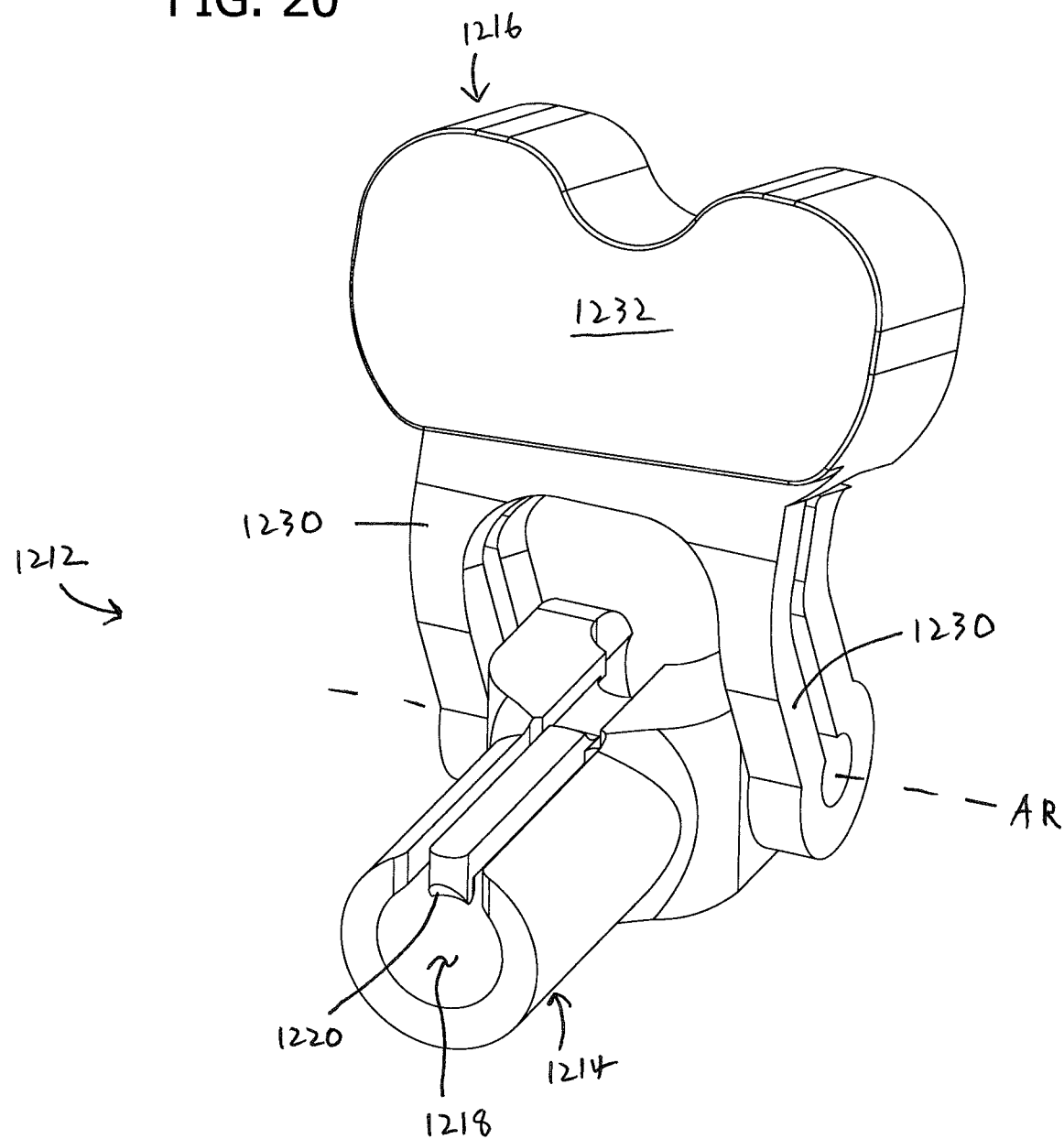
FIG. 20 is a rear perspective of the impaction guide.

Referring to FIGS. 18-20, an installation tool assembly for installing a curved keel tibial implant, such as the implant 1010, on the proximal end PE of the tibia T of the patient is generally indicated at reference numeral 1200. The installation tool assembly 1200 includes a tibial trial handle 1202 and an impaction guide 1212. The handle 1202 includes a footprint template 1204 used to determine the size of the tibia implant 1010 to be implanted on the tibia T. The footprint template 1204 may include one or more holes or spaces 1206 to allow the tibial keel and/or anchoring projections to be inserted into the proximal end PE of the tibia T while the footprint template overlies the tibia. The footprint template 1204 is releasably coupled to one end of a shaft 1208. The shaft 1208 has a generally circular cross-sectional shape. As explained in more detail below, the shaft 1208 includes positioning recesses or depressions 1210 used to position the impaction guide 1212 on the handle 1202.

The impaction guide 1212 is configured to insert the tibial implant 1010 in a curved manner (e.g., in a curved or arcuate path CP) into the proximal end PE of the tibia T. The impaction guide 1212 includes a mounting portion 1214 and a driving portion 1216. The mounting portion 1214 is configured to be coupled (e.g., releasably coupled) to the handle 1202. The mounting portion 1214 defines a handle opening 1218 sized and shaped to receive the shaft 1208 of the handle. The handle opening 1218 has opposite open ends to allow the mounting portion 1214 to slide over the end of the shaft 1208 and along the shaft of the handle 1202. The handle opening 1218 has a cross-sectional shape that matches or corresponds to the cross-sectional shape of the shaft 1208 of the handle 1202. Thus, in the illustrated embodiment, the handle opening 1218 has a circular cross-sectional shape. The mounting portion 1214 includes a detent or catch 1220 configured to position and secure the mounting portion on handle 1202. The detent 1220 is sized and shaped to be inserted into one of the recesses 1210 along the handle to position and lock the impaction guide 1212 in place on the handle 1202. In a locked position (FIG. 20), the detent 1220 generally extends into the handle opening 1220. When the impaction guide 1212 is mounted on the handle 1202, the detent 1220 extends into a recess 1210 when the detent is in the locked position. The detent 1220 may be reliantly biased toward the locked position, such as by a spring or a living hinge. Moving the detent to a release position (not shown), such that the detent 1220 is spaced from the recess 1210 (e.g., the handle opening 1218) permits the impaction guide 1212 to move or slide along the handle 1202.

The driving portion 1216 of the impaction guide 1212 is configured to hold the tibial implant 1010 and drive the tibial implant into the proximal end PE of the tibia T. The driving portion 1216 is pivotably coupled to the mounting portion 1214. In the illustrated embodiment, the driving portion 1216 is coupled to the mounting portion 1214 by a hinge 1222 (e.g., shafts extending through aligned openings in the mounting and driving portions). Thus, the driving portion 1216 generally rotates about an axis of rotation AR to drive the tibial implant 1010 into the tibia T. The driving portion 1216 includes a coupling head 1224 configured to releasably couple to the tibial implant 1010. In particular, the coupling head 1224 extends into the insert receiving space 22 and recesses 24 and engages the interior surface of the perimeter wall 20 to couple to the tibial implant 1010. The coupling head 1224 is configured to form a snap-fit or compression fit with the tibial implant 1010 to releasably coupled to the tibial implant. The coupling head 1224 includes mounting inserts 1226, 1228 (e.g., an anterior mounting insert and a posterior mounting insert). The mounting inserts 1226, 1228 are configured to be inserted into the insert receiving space 22 and/or recesses 24. The mounting inserts 1226, 1228 generally conform to a portion of the perimeter wall 20 of the tibial implant 1010. The mounting inserts 1226, 1228 are resiliently biased away from one another. The mounting inserts 1226, 1228 move away from one another and engage the perimeter wall 20 of the tibial implant 1010 to secure the tibial implant to the impaction guide 1212. To attach or release the tibial implant 1010 from the coupling head 1224, the mounting inserts 1226, 1228 are pushed toward one another to allow the inserts to move into or out of the insert receiving space 22. In the illustrated embodiment, resiliently deflectable arms 1230 couple the mounting inserts 1226, 1228 together. The arms 1230 also define a portion of the hinge 1222. The illustrated arms 1230 generally have a U-shape. The coupling head 1224 also includes a contact surface 1232 configured to be engaged or hit by a hammer (not shown) to rotate the driving portion 1216 about the axis of rotation AR and drive the tibial implant 1010 into the proximal end PE of the tibia T. The driving portion 1216 is configured such that when the tibial implant 1010 is attached to the coupling head 1224, the axis of curvature about which the curved tibial keel 128 curves about is generally collinear with the axis of rotation AR. The allows the driving portion 1216 to move the tibial implant 1010 along a curved path that generally corresponds to and matches the curve of the tibial keel 128.

In one method of operation using the installation tool assembly 1200, a surgeon uses the handle 1202 to select the appropriate size of tibial implant 1010. The surgeon uses the footprint template 1204, a procedure that is generally known in the art, to determine the size of the tibial implant 1010 to be implanted on the proximal end PE of the tibia T. The handle 1202 is also secured in place relative to the tibia T using conventional means known in the art. Once the size of the tibial implant 1010 is determined, the surgeon selects the correct size of tibial implant and attaches it to the coupling head 1224 of the impaction guide 1216. The tibial implant 1010 is attached to the coupling head 1124 by moving the mounting inserts 1226, 1228 toward one another so that they can be inserted into the insert receiving space 22. Once in the insert receiving space 22, the mounting inserts 1226, 1228 move away from one another and engage the perimeter wall 20 to secure the implant to the impaction guide 1216. The surgeon then inserts the shaft 1208 of the handle 1202 through the handle opening 1218 of the mounting portion 1214 and slides the impaction guide 1216 along the handle. The surgeon aligns the detent 1220 with the desired recess 1210 to set and secure the impaction guide 1212 at the desired position along the handle 1202. After, the surgeon uses a hammer to impact the contact surface 1232 and drive the tibial implant 1010 into the tibia T. The hammer rotates the driving portion 1216 and tibial implant 1010 about the axis of rotation AR, moving the tibial implant 1010 along the curved path. In one embodiment, surgeon may hammer the tibial implant 1010 entirely into the proximal end PE of the tibia T before removing the installation tool assembly 1200. In another embodiment, the surgeon may partially hammer the tibial implant 1010 into the proximal end PE of the tibia T and then remove the installation tool assembly 1200. After the installation tool assembly 1200 is removed, the surgeon drives the tibial implant 1010 the rest of the way into the tibia T. For example, the surgeon may drive the tibial implant to an intermediate position such as about half way into the tibia T. In this embodiment, the curved tibial keel 128 continues to guide the tibial implant 1010 along the curved path as the implant is further driven into the tibia T. To detach the tibial implant 1010 from the tibial implant 1010, the surgeon moves the mounting inserts 1226, 1228 toward one another and then out of the insert receiving space 22. As mentioned above, the tibial keel 128 of tibial implant 1010 has sharp edges which allows the tibial implant 1010 to be implanted without some prior bone preparation required to implant conventional tibial implant. Specifically, the step of preparing the tibia T for the tibia keel (e.g., predrilling a hole) is eliminated. In addition, the implanting of the curved keel tibial implant 1010 as described herein reduces the dislocation, distraction and clearance needed to install the tibial implant over conventional straight keel implantation techniques.

Figure 21:
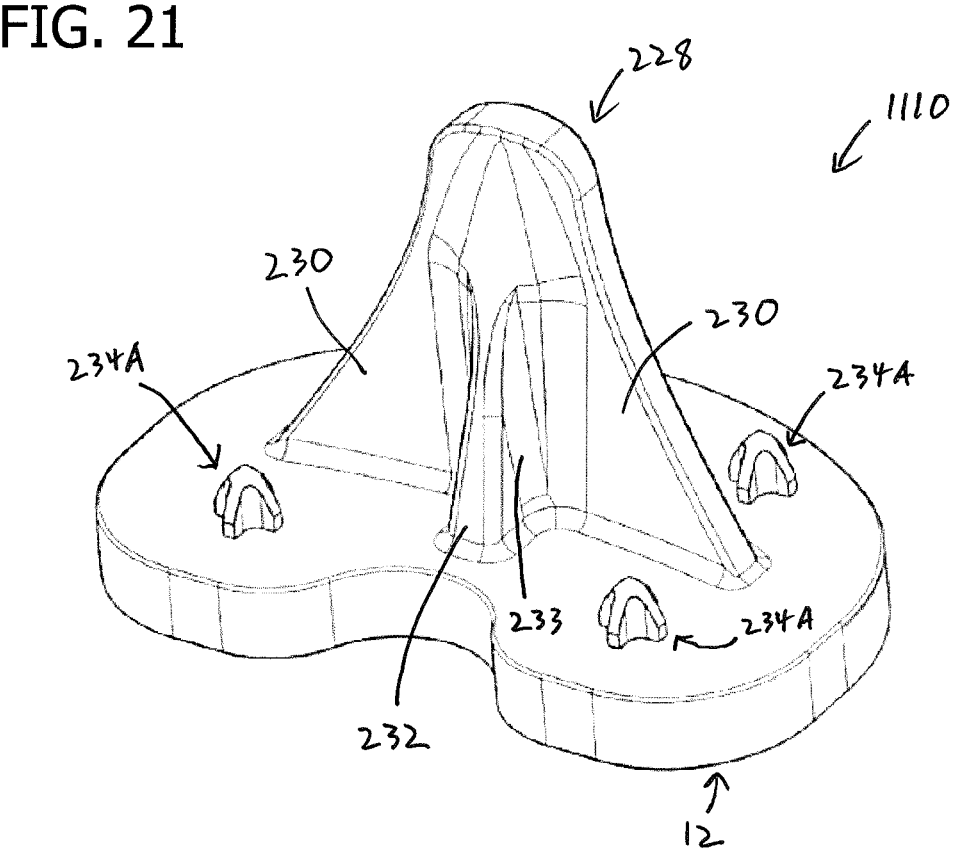
FIG. 21 is a bottom perspective of a tibial implant according to another embodiment of the present disclosure.
Figure 22:
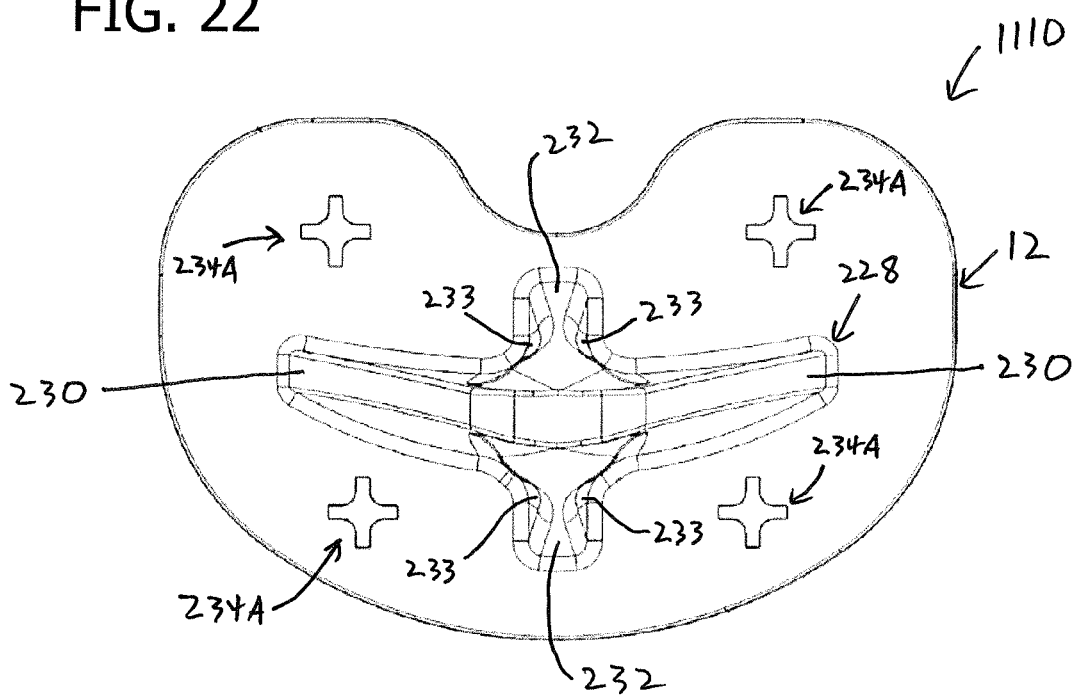
FIG. 22 is a bottom plan view of the tibial implant of FIG. 21.

Referring to FIGS. 21 and 22, a tibial keel for a tibial implant 1110 according to another embodiment of the present disclosure is generally indicated at reference numeral 228. In this embodiment, the tibial keel 228 with coronal fins 230 and sagittal fins 232. In this embodiment, the edges of the fins and the nose of the tibial keel 228 is generally blunt (e.g., generally planar). In addition, the sagittal fins 232 of the tibial keel 228 include concave sides 233. Other configurations of the tibial keel are within the scope of the present disclosure. For example, in one embodiment a tibial implant includes a tibial keel (not shown) at an angle to the vertical, such as slanted forward (instead of curved forward). The slanted angle of the tibial keel makes it easier to implant the tibial implant on the proximal end PE of the tibia T. The slanted tibial keel allows the tibial implant to start at a more forward or anterior position and then move rearward or posteriorly due to the slanted keel as the implant is driven into the proximal end PE of the tibia T. Being able to start the implantation of the tibia implant at a more anterior position, compared to straight keels, provides more clearance between the implant and other parts of the patient's body (such as the femur) and/or other surgical tools, making it easier to insert the implant into the tibia T.

Figure 23:
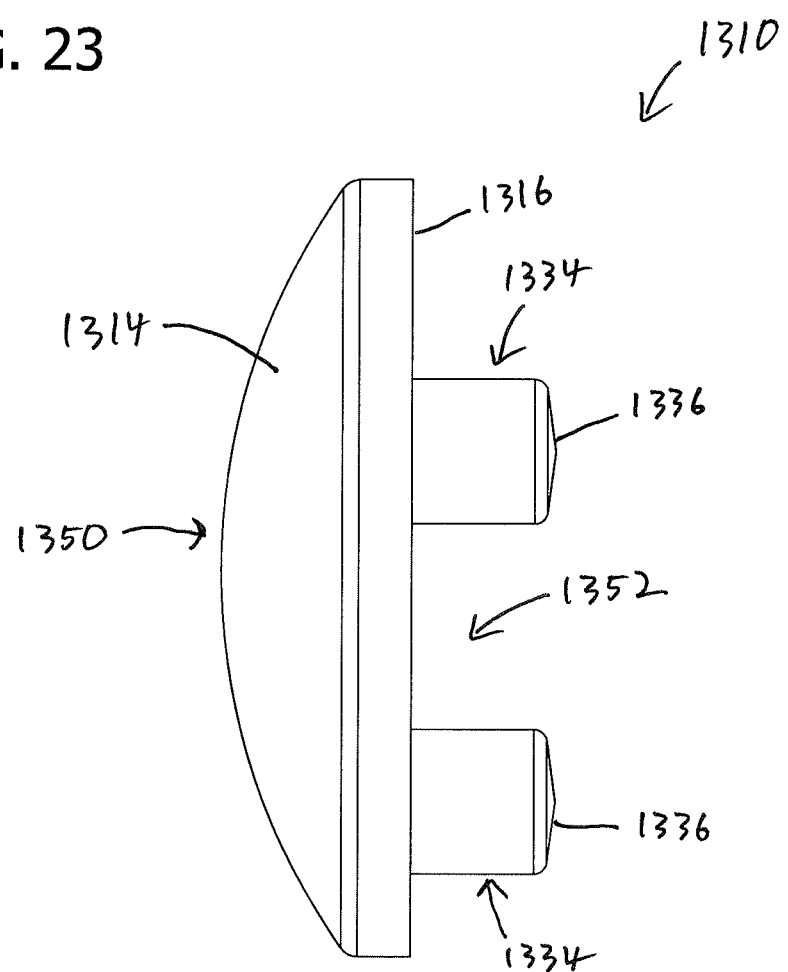
FIG. 23 is a side elevation of a patella implant according to one embodiment of the present disclosure.

It is understood that the elements, features and methods of and relating to the tibial implants 10, 110, 210, 310, 410, 510, 610, 710, 810, 910, 1010, 1110 described herein can be applied to other bone implants, including but not limited to femoral implants and patella implants. For example, the porous regions of the tibial implant and be incorporated in other bone implants such as patella implant. An example of such a patella implant is generally indicated by reference numeral 1310 in FIGS. 23-25. The patella implant 1310 is sized and shaped to be implanted on the backside of the patella. The patella implant 1310 includes a proximal or articulating surface 1314 and an opposite distal surface 1316. The distal surface 1316 is configured to engage the backside of the patella. The articulating surface 1314 has a partial dome shape. The patella implant 1310 includes a porous region, as discussed above. In particular, the distal surface 1316 is porous (e.g., is a porous region). In the illustrated embodiment, a portion of the distal surface 1316 is porous, although in other embodiments the entire distal surface 1316 may be porous. The portion of the distal surface 1316 that is porous is generally centrally located on the distal surface and spaced apart the peripheral edge of the distal surface. The porous region has a generally circular shape disposed within the larger circular shape of the distal surface 1316. As shown in the illustrated embodiment, the porous region comprises generally hexagonal struts coupled together to form a lattice, although any suitable porous structure is within the scope of the present disclosure. As mentioned above the porosity of the distal surface 1316 allows the patella implant 1310 be inserted into or implanted on the patella without the cement conventionally used in knee arthroplasties, reducing procedural times, cement related complications and surgeon stress.

The patella implant 1310 includes a cap 1350 and a base or anchor 1352 coupled together. The cap 1350 defines (e.g., includes) the articulating surface 1314 and a portion of the distal surface 1316. In the illustrated embodiment, the portion of the distal surface 1316 defined by the cap 1350 is not porous. The cap 1350 can be made out of a polymeric material or any other suitable material. The base 1352 defines a portion of the distal surface 1316. In the illustrated embodiment, the portion of the distal surface 1316 defined by the base 1352 is porous. The base 1352 also includes at least one (e.g., a plurality of) anchoring projections 1334, similar to the anchoring projections discussed above. In the illustrated embodiment, the patella implant 1310 includes three anchoring projections 1334, although more or fewer anchoring projections are within the scope of the present disclosure. Each anchoring projection 1334 extends generally distally from the distal surface 1316. In this embodiment, each anchoring projection 1334 is cylindrical (e.g., has a cylinder shape) with a shallow conical distal tip 1336. The anchoring projection 1334 is also solid (FIG. 24), although in other embodiment the anchoring projection can be hollow. The base 1352 may be made out of a metal or any other suitable material.

Figure 24:
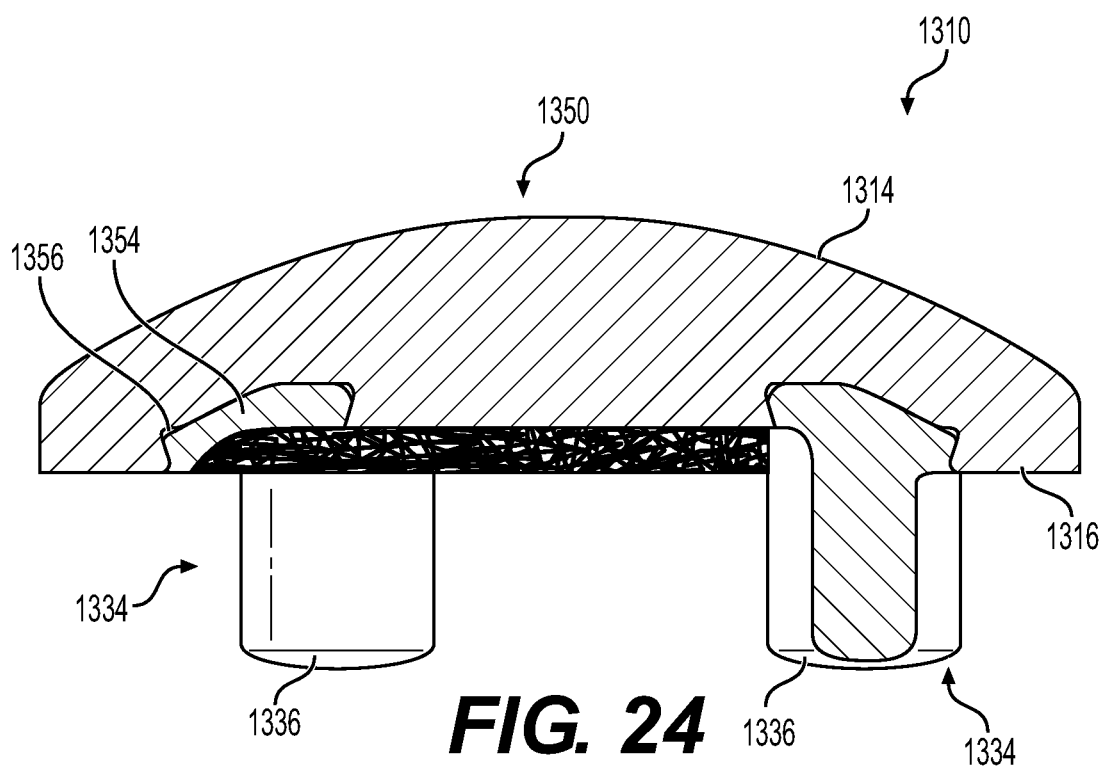
FIG. 24 is a cross-section of the patella implant.

The cap 1350 and base 1352 are configured to be coupled together to form the patella implant 1310. In the illustrated embodiment, the cap 1350 and the base 1352 are configured to form a snap-fit connection. The base 1352 includes a support ring 1354 with opposite inner and outer circumferential edge margins or surfaces. As shown in FIG. 24, the inner and outer edge margins of the support ring 1354 are tapered away from one another as the edge margins extend generally upward. As a result, the proximal end of the support ring 1354 is wider than the distal end of the support ring (e.g., a generally dovetail cross-sectional shape). The cap 1350 includes a generally circumferential channel 1356 or recess sized and shaped to receive the support ring 1354. The support ring 1354 and the channel 1356 have corresponding sizes and shapes. The cap 1350 includes opposite inner and outer circumferential surfaces defining the sides of the channel 1356. The inner and outer surfaces of the cap 1350 correspond to the taper of the inner and outer edge margins of the support ring 1354. As shown in FIG. 24, the inner and outer surfaces of the cap 1350 also tapper away from one another as the surfaces extend generally upward. As a result, the channel 1356 has a mouth that is narrower than its base (e.g., a generally dovetail cross-sectional shape). To assemble the patella implant 1310, the support ring 1354 of the base 1352 is inserted into the channel 1356 of the cap 1350. The cap 1350 is resiliently deformable and may deform to enlarge the mouth of the channel 1356 to allow the support ring 1354 to pass therethrough before returning or snapping back toward its initial or at rest state, thereby securing the cap and base 1352 together. The cap 1350 engages the support ring 1354 to secure the base 1352 to the cap. The tapered inner and outer surfaces of the cap 1350 and support ring 1354 engage each other, respectively, to secure the cap and base 1352 together. The support ring 1352 also provides rigidity for the patella implant 1310 and a mounting platform for the porous structure (e.g., hexagonal struts).

The base 1352 may be constructed using the manufacturing techniques and processes discussed herein. For example, the base 1352 can be constructed using hybrid manufacturing, as mentioned above. In a hybrid manufacturing process, the support ring 1354 and anchoring projections 1334 can first be created by conventional manufacturing methods, such as cold forming (e.g., stamping, cutting, deforming) a metal blank or by forging. The partially formed base 1352 is then placed in an additive manufacturing machine which builds the porous regions thereon. The cap 1350 is then attached to the base 1352 to complete the construction of the patella implant 1310. The polymeric cap 1350 may be formed by conventional methods such as compression molding.

Referring to FIGS. 26-35, various different systems and methods for verifying the implantation of an implant relative to the bone of a patient are disclosed. The following descriptions describe the different systems and methods for verifying the position or placement of knee arthroplasty implants relative to the bone. For example, these systems and methods can be used to verify the position of a tibial implant 10, or any of the implants disclosed herein, relative to the proximal end PE of the tibia T of a patient. However, it is understood that these systems and methods for verifying the position of an implant can be used in other surgical applications besides knee arthroplasties.

Total knee arthroplasty relies on the proper placement of femoral and tibial implants. In conventional knee arthroplasty surgeries, the final placement of the implants depends on the surgical skill in both placing the implant on the bone and performing the saw cuts in the bone upon which the implant sits. There are a variety of different systems for creating the saw cuts in the bone. For example, the saw cuts for the implant can be driven by manual, non-computer assisted instruments, or with the aid of navigation instruments which provide computer assisted feedback on the saw cut positioning, or with a surgical robot which provides robotically-assisted guidance on saw cut positioning. Further details on surgical robots and robotically-assisted guidance on saw cut positioning may be found in U.S. patent application Ser. No. 16/737,054, filed Jan. 8, 2020, the entirety of which is incorporated herein by reference. While the implants generally follow the saw cuts, in conventional knee arthroplasties the final position of the implants is still dependent on surgical experience, skill, feel and eye. The follow systems and methods provide verification and confirmation on the position of the implant on the bone of the patient.

It is understood that the systems (e.g., surgical robots, tracking systems, etc.) and methods of performing knee arthroplasties disclosed in U.S. patent application Ser. No. 16/737,054 may be used to perform, to guide, to assist in and/or in conjunction with knee arthroplasties using the systems (e.g., implants, position verification system, etc.) and methods (e.g., implant implantation, position verification, etc.) described herein.

Figure 26:
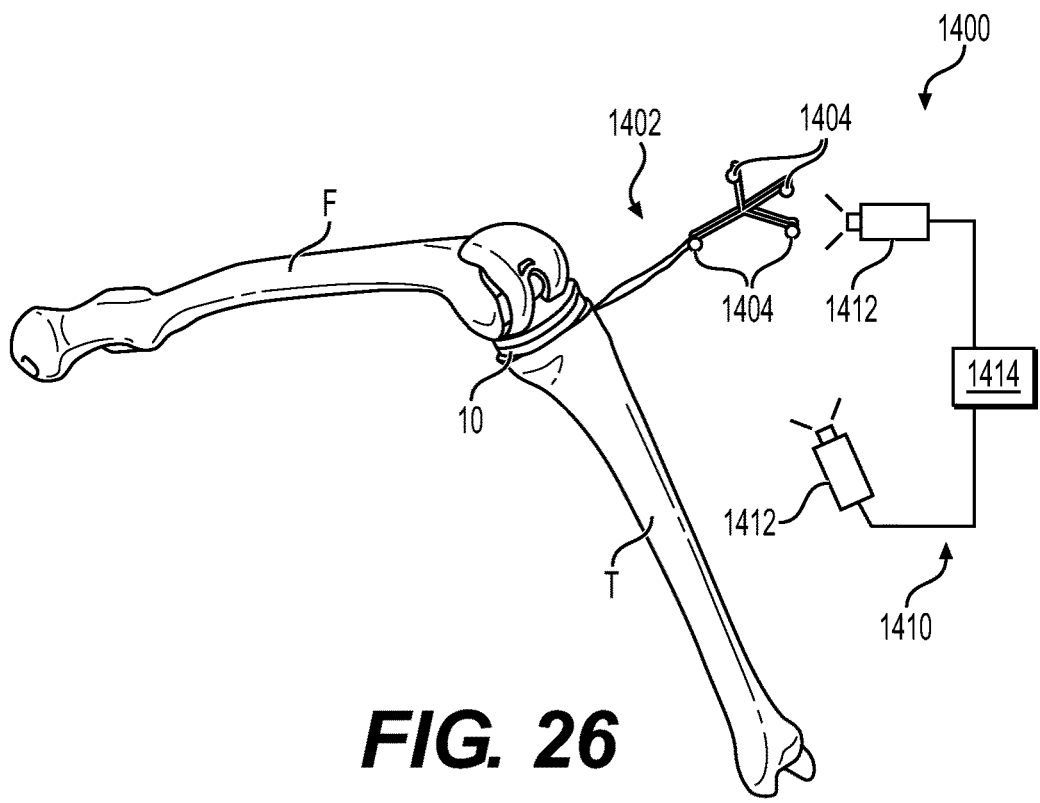
FIG. 26 is a schematic illustration of a position verification system with a position indicator engaging a positioning guide of a tibial implant in order to verify the position of the tibial implant relative to a proximal end of a tibia of a patient.

Referring to FIG. 26, a position verification system according to one embodiment of the present disclosure is generally indicated at reference numeral 1400. The position verification system 1400 is configured to verify or determine the position of the tibial implant 10 relative to the proximal end PE of the tibia T. The position verification system 1400 can be used during and/or after the implantation of the tibial implant 10 on the proximal end PE of the tibia T. The position verification system 1400 includes a position indicator 1402 and a tracker 1410 (e.g., a tracking system). The position indicator 1402 is configured to indicate the position of the tibial implant 10. The tracker 1410 is configured to track or locate, in real time, the position of the position indicator 1402 (in 3D space) in order to determine the position of the of the tibial implant 10. The position indicator 1402 is configured to be positioned relative to the tibial implant 10 to indicate the position of the tibial implant. The position indicator 1402 includes a plurality of (e.g., four) tracking markers or indicators 1404 that are tracked by the tracker 1410. The indicators 1404 are visual or optical markers that are recognized by the tracker 1410. In the illustrated embodiment, the indicators 1404 are spheres or balls, although any suitable optical marker is within the scope of the present disclosure. The position indicator 1402 has a fixed geometry and the tracker 1410 knows the geometry of the position indicator. Accordingly, by tracking the position of the indicators 1404 on the position indicator 1402, the tracker 1410 can determine or extrapolate the position of what the position indicator is touching or coupled to. In the embodiment illustrated in FIG. 26, the position indicator 1402 comprises a stylus. The stylus 1402 has a tip. In one embodiment, the tip of the stylus 1402 is a ball or sphere. As will be explained in more detail below, the surgeon may engage the tip of the stylus 1402 with different components (e.g., the tibial implant 10, arthroplasty tools, etc.) to determine the position of the tibial implant. The tracker 1410 knows the position of the tip of the stylus 1402 relative to the indicators 1404. The tracker 1410 can determine the position of the tip of the stylus 1402 using the indicators 1404 and the known geometry of the stylus, and thereby the position of what the tip of the stylus is touching or is engaged with. Other configurations of the position indicator 1402 are within the scope of the present disclosure, some of which are described herein. For example, the position indicator 1402 may be a dynamic reference array as described in U.S. patent application Ser. No. 16/737,054.

The tracker 1410 tracks or locates the position indicator 1402 to determine the position of the position indicator in the 3D space. The tracker 1410 may be a camera based tracker (e.g., camera tracking system) such as the one described in U.S. patent application Ser. No. 16/737,054. The tracker 1410 includes one or more cameras 1412 wired or wirelessly coupled (e.g., in communication with) a tracking computer 1414. The cameras 1412 are configured to capture images (e.g., pictures, video, etc.) of the position indicator 1402 and the tracking computer 1414 determines the position of the position indicator and the tibial implant 10 based on the indicators 1404 in the images from the cameras. The tracking computer 1414 may include a display (e.g., a video display) to output information to the surgeon, such as the position of the tibial implant 10 relative to the proximal end PE of the tibia T. The tracker 1410 may also determine the position of the bone (e.g., tibia T) in the 3D space, as described in U.S. patent application Ser. No. 16/737,054, although other ways of determining the position of the bone are within the scope of the present disclosure. In general, the tracker 1410 compares the position of the tibia T to the position of the tibial implant 10 to determine the position of the implant relative to the tibia. The tracker 1410 then outputs or displays this information to the surgeon. It is understood that the position verification system 1400 may be part of a larger surgical system (e.g., larger robotic surgical system).

The position verification system 1400 can be used in a variety of different ways to determine the position of the tibial implant 10 relative to the proximal end PE of the tibia T. In one method of operation as shown in FIG. 26, the position verification system 1400 is configured to mate or register with the one or more positioning guides 26 of the tibial implant 10 to determine the position of the tibial implant. In this embodiment, the position indicator 1402 (e.g., tip of the stylus) mates or registers with the one or more positioning guides 26 of the tibial implant 10. For example, the tip of the stylus 1402 is inserted into the recesses 26 of the tibial implant 10. The tracker 1410 then determines the position of the one or more positioning guides 26 (e.g., recesses) to determine the position of the tibial implant 10 relative to the proximal end PE of the tibia T. For example, in one exemplary method, the surgeon positions the tibial implant 10 relative to the proximal end PE of the tibia, such as by placing the tibial implant on the proximal end of the tibia. After, the surgeon positions the position indicator 1402 relative to the tibial implant 10. The tracker 1410 tracks the position indicator 1402 to determine the position of the tibial implant 10 (e.g., the position of the tibial implant in the 3D space). In this embodiment, the surgeon uses the stylus 1402 to register or engage (e.g., touch), with the tip, the various positioning guides 26 (e.g., the position indicator directly engages the implant). The tracker 1410 tracks the position of the position indicator 1402 as the position indicator is positioned relative to the tibial implant 10. In particular, the tracker 1410 tracks the stylus 1402 to determine the position of the positioning guides 26 and to extrapolate or determine the position of the tibial implant. In one embodiment, the surgeon tells the tracker 1410 when the stylus 1402 is registered with a positioning guide 26 via a user interface of the tracker so the tracker knows what positions of the position indicator correspond to positions of the tibial implant 10 (e.g., positioning guides). As with the position indicator 1402, in this embodiment, the tracker 1410 knows the geometry of the tibial implant 10 and can determine the position of the tibial implant based on the known geometry of the tibial implant and the positions of the positioning guides 26. In one embodiment, the tracker 1410 accesses the implant's geometry based on the position of the positioning guides 26. As mentioned above, the positions of the positioning guides 26 can be used to encode information unique to that style (e.g., type, size, etc.) of implant. After determining the positions of the positioning guides 26, the tracker 1410 can access the implant database and use the positioning guide information (e.g., distances between positioning guides) to locate the specific implant in the database and associated implant information, such as the name, type, size, geometry, etc. In other embodiments, the surgeon may provide this information manually, via the user interface, to the tracker or enter information allowing the tracker to access the correct implant entry in the implant database.

Figure 27:
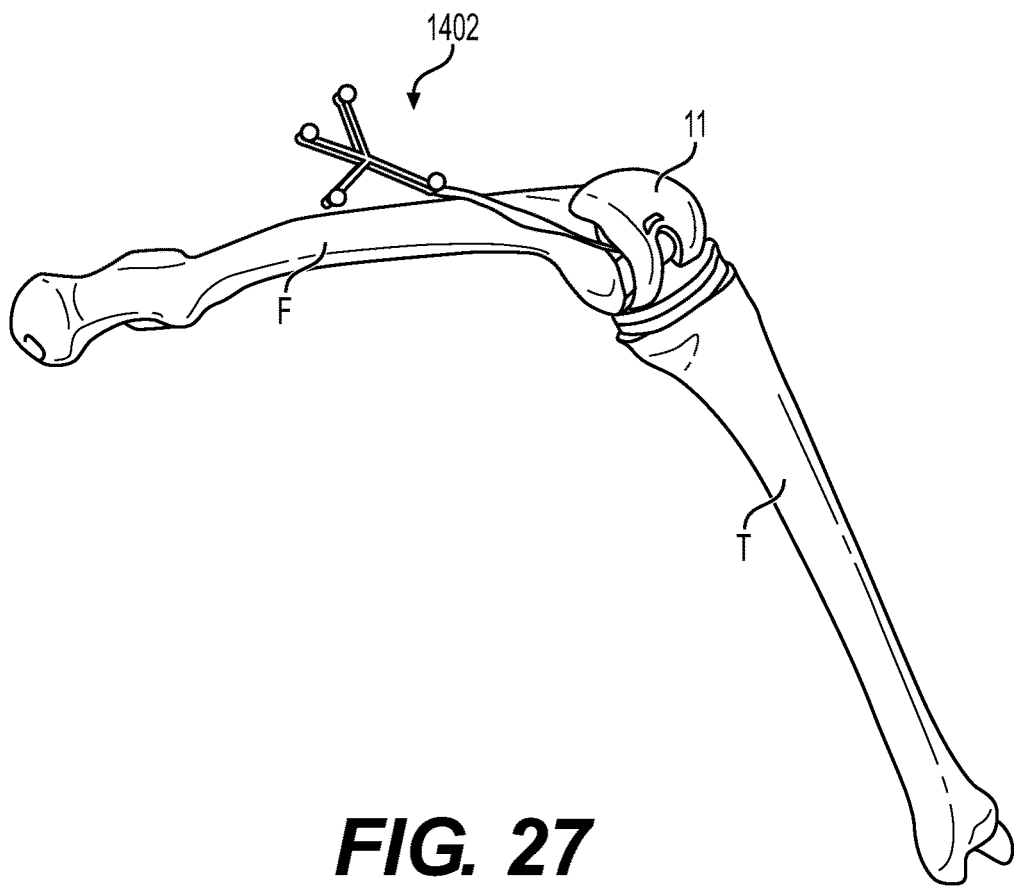
FIG. 27 is a perspective of the position indicator of FIG. 26 engaging a positioning guide of a femoral implant in order to verify the position of the femoral implant relative to a distal end of a femur of a patient.

Continuing with the method, at some point, the tracker 1410 determines or is informed of the position of the tibia T (e.g., the position of the tibia in the 3D space). This can be before, during or after the position of the tibial implant 10 is determined. The position of the tibial implant 10 in the 3D space is then compared relative to the position of the tibia T in the 3D space in order to verify whether or not the tibial implant is correctly positioned on the proximal end PE of the tibia. The tracker 1410 provides feedback to the surgeon regarding the position of the tibial implant 10 relative to the tibia T. The tracker 1410 may compare the positions of the tibia T and the tibial implant 10 or may display information to allow the surgeon to compare the positions of the tibia and tibial implant. The tracker 1410 or surgeon may compare the position of the tibial implant 10 relative to (e.g., on) the tibia T to a baseline or ideal position to determine if the tibial implant is correctly positioned. Ideal position is previously determined, such as by the surgeon, and is the theoretically perfect position of the tibial implant 10 on the tibia T (e.g., relative to the proximal end PE of the tibia). If the position of the tibial implant 10 relative to the tibia T aligns with the ideal position (or is within an appropriate margin of error), the tibial implant is correctly position and the surgeon can proceed with the rest of the surgery. If the position of the position of the tibial implant 10 relative to the tibia T does not align with the ideal position, the surgeon adjusts the position of the implant as needed before proceeding with the surgery. After the tibial implant 10 is repositioned, the surgeon can repeat the steps of above to determine the whether the new or adjusted position of the tibial implant is correct. This same process can be used to determine the position of other implants relative to a bone. For example, as shown in FIG. 27, the same process can be used to verify the position of a femoral implant 11 by registering the position indicator 1402 of the position verification system 1400 with the one or more positioning guides 26 of the femoral implant.

Figure 28:
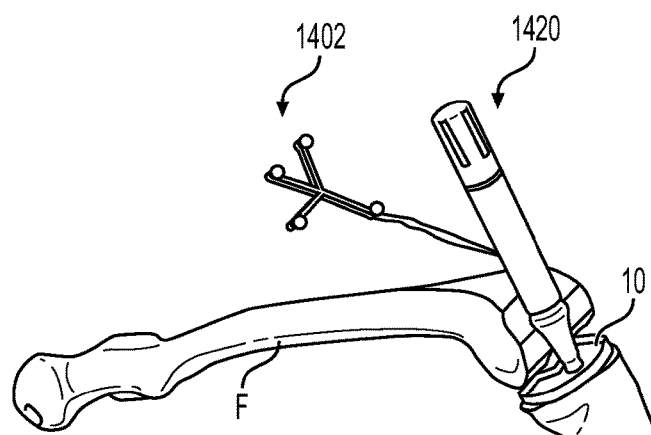
FIG. 28 is a perspective of the position indicator of FIG. 26 engaging a tibial installation tool attached to a tibial implant in order to verify the position of the tibial implant relative to the proximal end of the tibia.

Referring to FIG. 28, in another method of operation, the position verification system 1400 is configured to mate or register with the one or more positioning guides 26 on an arthroplasty tool 1420 (e.g., a tibial installation tool, a femoral installation tool) to determine the position of the tibial implant 10. The arthroplasty tool 1420 is configured to releasably attach to the tibial implant 10. When the arthroplasty tool 1420 and tibial implant 10 are coupled together, the arthroplasty tool is rigidly and immovably secured to the tibial implant. The arthroplasty tool 1420 can be any suitable tool, such as an implant (e.g., tibial implant, femoral implant) holder. The arthroplasty tool 1420 includes one or more positioning guides 26, as described above. In this embodiment, the position indicator 1402 (e.g., tip of the stylus) mates or registers with the one or more positioning guides 26 of the arthroplasty tool 1420 (e.g., the position indicator indirectly engages the implant via the tool). The tracker 1410 then determines the position of the one or more positioning guides 26 (e.g., recesses) to determine the position of the arthroplasty tool 1420 and then determine the position of the tibial implant 10. For example, in one exemplary method, the surgeon positions the tibial implant 10 relative to the proximal end PE of the tibia, such as by placing the tibial implant on the proximal end of the tibia. In one embodiment, the surgeon may place the tibial implant 10 using the arthroplasty tool 1420 and leave the tool attached to the implant. In another embodiment, the surgeon attaches the arthroplasty tool 1420 to the tibial implant 10 after the tibial implant is implanted on the tibia T. After, the surgeon positions the position indicator 1402 relative to the tibial implant 10. The tracker 1410 tracks the position indicator 1402 to determine the position of the tibial implant 10. In this embodiment, the surgeon uses the stylus 1402 to register or engage (e.g., touch), with the tip, the various positioning guides 26 of the arthroplasty tool 1420. The tracker 1410 tracks the position of the position indicator 1402 as the position indicator registers with the positioning guides 26 of the arthroplasty tool 1420. The tracker 1410 tracks the stylus 1402 to determine the position of the positioning guides 26 and to extrapolate or determine the position of the arthroplasty tool 1420 and of the tibial implant 10. As with the position indicator 1402, in this embodiment, the tracker 1410 knows the geometry of the tibial implant 10, the geometry of the arthroplasty tool 1420 and the relative orientation and position of the tibial implant and arthroplasty tool when the arthroplasty tool is attached to the tibial implant. The tracker 1410 uses this information to determine the position of the tibial implant based the positions of the positioning guides 26. As discussed above, the positioning guides 26 can be used to access the relevant information (e.g., geometry, orientation and location of a tibial implant attached to the tool) regarding the arthroplasty tool.

Figure 29:
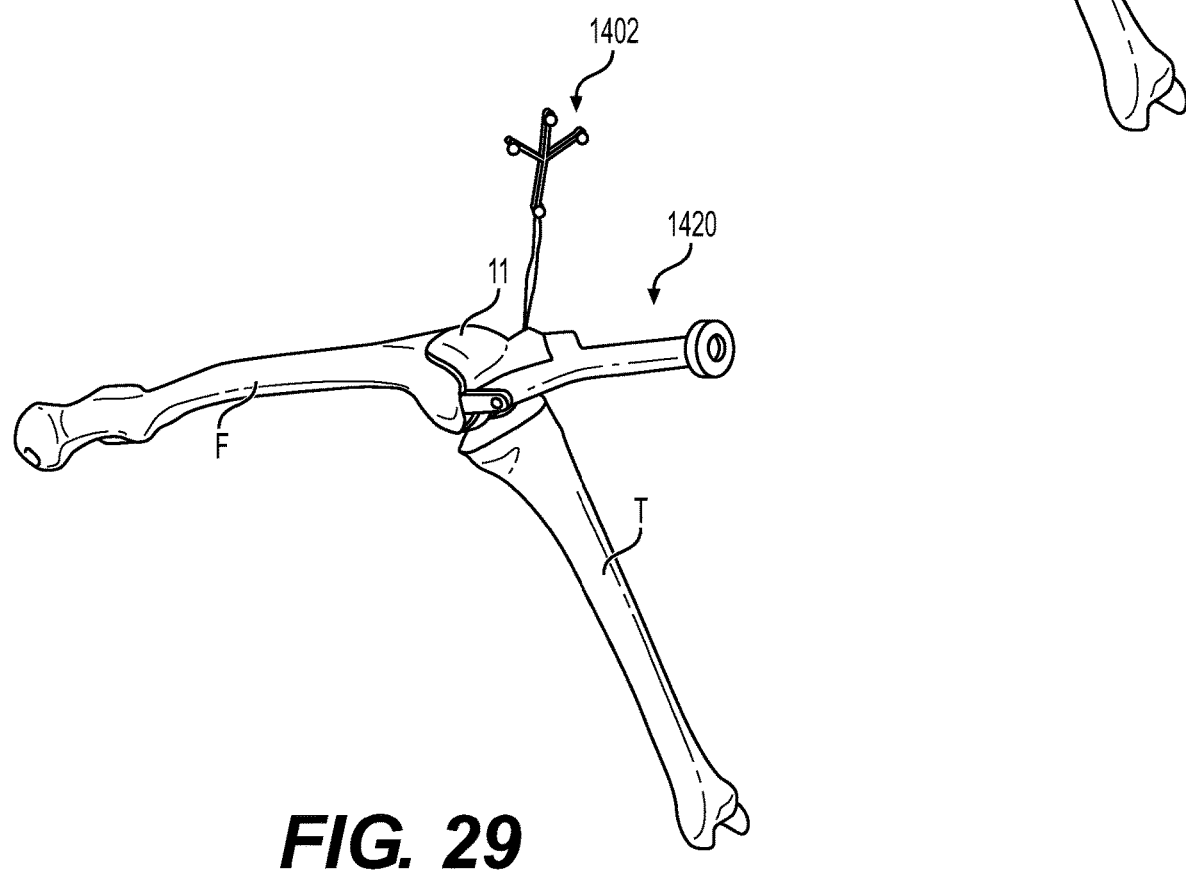
FIG. 29 is a perspective of the position indicator of FIG. 26 engaging a femoral installation tool attached to a femoral implant in order to verify the position of the femoral implant relative to the distal end of the femur.

After the tracker 1410 determines the position of the tibial implant 10, the process is generally the same as above. The tracker 1410 determines or is informed of the position of the tibia T. The position of the tibial implant 10 is then compared relative to the position of the tibia T in order to verify whether or not the tibial implant is correctly positioned on the proximal end PE of the tibia. If the position of the tibial implant 10 relative to the tibia T is correct, the surgeon can proceed with the rest of the surgery. If the position of the position of the tibial implant 10 relative to the tibia T is incorrect, the surgeon adjusts the position of the implant as needed before proceeding with the surgery. This same process can be used to determine the position of other implants relative to a bone. For example, as shown in FIG. 29, the same process can be used to verify the position of a femoral implant 11 by registering the position indicator 1402 of the position verification system 1400 with the one or more positioning guides 26 of an arthroplasty tool 1420 coupled to the femoral implant.

Figure 30:
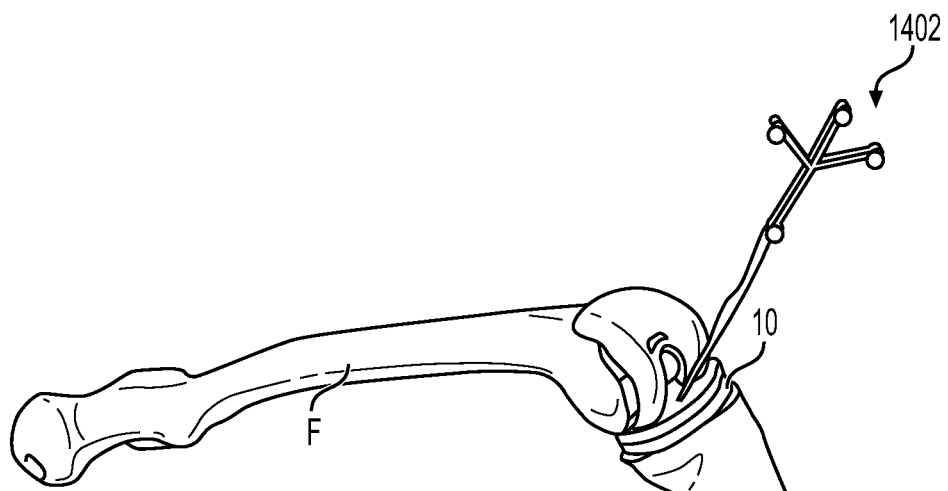
FIG. 30 is a perspective of the position indicator of FIG. 26 engaging a tibial implant in order to verify the position of the tibial implant relative to the proximal end of the tibia.
Figure 31:
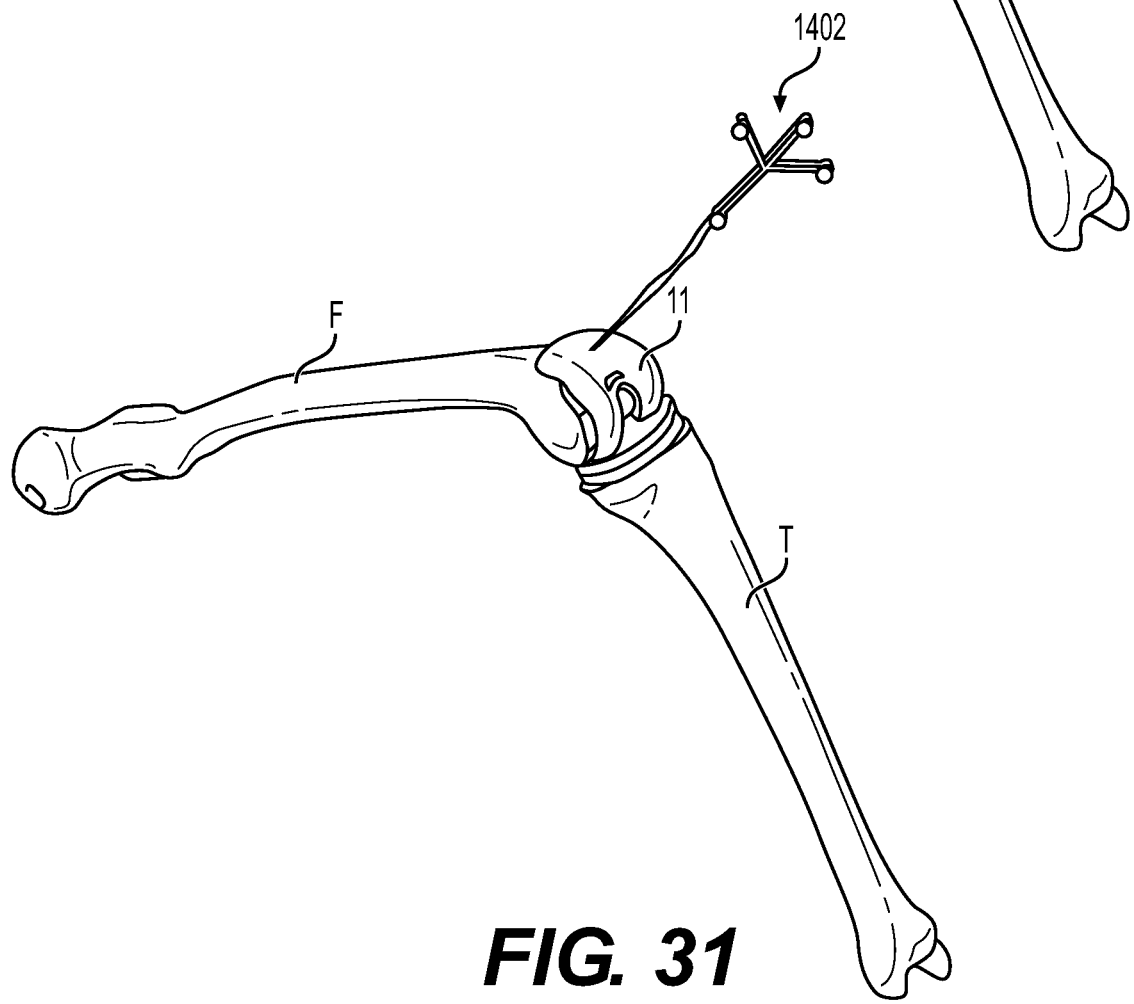
FIG. 31 is a perspective of the position indicator of FIG. 26 engaging a femoral implant in order to verify the position of the femoral implant relative to the distal end of the femur.

Referring to FIG. 30, in another method of operation, the position verification system 1400 is configured to engage the tibial implant 10 at a plurality of different locations on the tibial implant to determine the position of the tibial implant. In this embodiment, the surgeon brushes or moves the position indicator 1402 (e.g., the tip of the stylus) over all or a portion of the tibial implant 10. The tracker 1410 tracks the position indicator 1402 as the position indicator engages and moves over the tibial implant 10 to generate information (e.g., cloud points or cloud point data) corresponding to the size, shape and position of the tibial implant. For example, in one exemplary method, the surgeon positions the tibial implant 10 relative to the proximal end PE of the tibia, such as by placing the tibial implant on the proximal end of the tibia. After, the surgeon positions the position indicator 1402 relative to the tibial implant 10. The tracker 1410 tracks the position indicator 1402 to determine the position of the tibial implant 10. In this embodiment, the surgeon brushes or moves the tip of the stylus 1402 over the tibial implant 10 or a target region thereof. For example, the surgeon may move the stylus back and forth over the tibial implant 10. In this embodiment, the tip of the stylus 1402 is configured to not damage (e.g., scratch) the tibial implant 10 as the tip slides over the implant. The tracker 1410 tracks the position of the position indicator 1402 as the position indicator brushes the tibial implant. The tracker 1410 tracks the stylus 1402 to determine the position of the tibial implant 10. As the tacker 1410 track the stylus cloud point data is generated corresponding to the size, shape (e.g., contours), and position of the tibial implant 10. As with the position indicator 1402, in this embodiment, the tracker 1410 knows the geometry of the tibial implant 10 and uses this information to determine the position of the tibial implant based the cloud point data. Similar to the positioning guides 26 discussed above, in one embodiment, the cloud point data can be used to access the relevant information (e.g., geometry) regarding the tibial implant 10 from an implant database. The tracker 1410 can align the geometric information or data from the implant database for the tibial implant 10 with the cloud point data, using surface matching algorithms, to determine the position of the tibial implant 10.

After the tracker 1410 determines the position of the tibial implant 10, the process is generally the same as described in the embodiments above. The tracker 1410 determines or is informed of the position of the tibia T. The position of the tibial implant 10 is then compared relative to the position of the tibia T in order to verify whether or not the tibial implant is correctly positioned on the proximal end PE of the tibia. If the position of the tibial implant 10 relative to the tibia T is correct, the surgeon can proceed with the rest of the surgery. If the position of the position of the tibial implant 10 relative to the tibia T is incorrect, the surgeon adjusts the position of the implant as needed before proceeding with the surgery. This same process can be used to determine the position of other implants relative to a bone. For example, as shown in FIG. 30, the same process can be used to verify the position of a femoral implant 11 by brushing the position indicator 1402 of the position verification system 1400 over the femoral implant.

Figure 32:
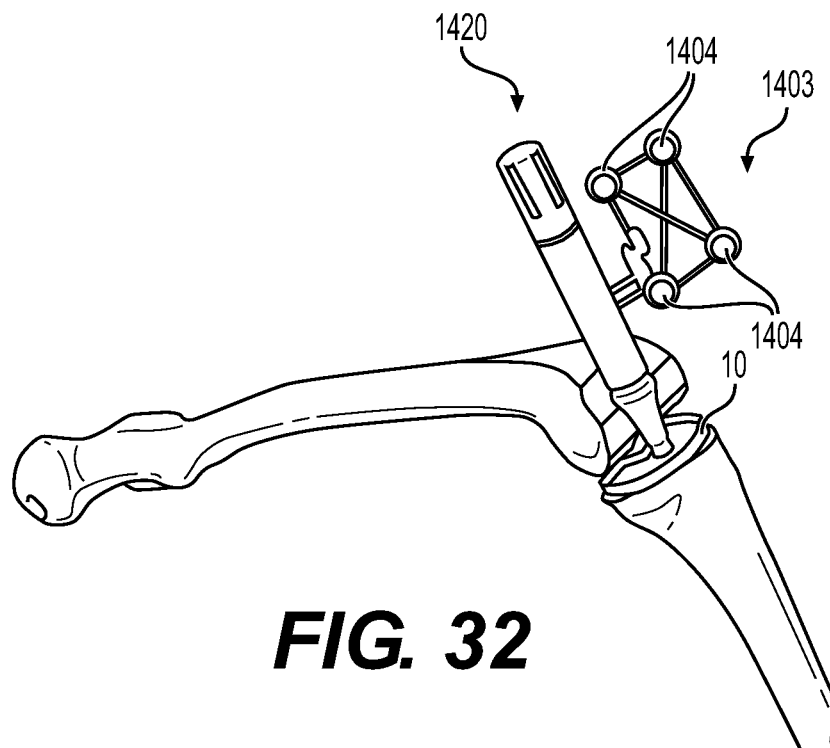
FIG. 32 is a perspective of a position indicator of a position verification system secured to a tibial installation tool attached to a tibial implant in order to verify the position of the tibial implant relative to the proximal end of the tibia.

Referring to FIG. 32, another embodiment of a position indicator of the positioning system 1400 is generally indicated a reference numeral 1403. In this embodiment, the position indicator 1403 is an array that is mounted (e.g., coupled) to an arthroplasty device, such as a tool, accessory or implant. The array 1403 includes a frame supporting the indicators 1404. The position indicator 1403 may be releasably coupled to the arthroplasty device or fixed to the arthroplasty device. When the position indicator 1403 is mounted on the arthroplasty device, the position indicator is rigidly and immovable secured to the arthroplasty device. The position indicator 1403 includes indicators 1404, as discussed above. In this embodiment, the position indicator 1403 is rigidly coupled to an arthroplasty tool 1420, such as the implant holder. As discussed above, the arthroplasty tool 1420 is configured to releasably attach to the tibial implant 10.

In an exemplary method of operation, the position verification system 1400 is configured to track the position indicator 1403 coupled to the arthroplasty tool 1420 to determine the position of the tibial implant 10. In this embodiment, the position verification system 1400 can provide feedback to the surgeon regarding the placement of the tibial implant 10 both during the implantation and after the implantation is completed. By being able to determine the position of the tibial implant 10 relative to the tibia T during implantation of the implant, the quality and quantity of available bone stock is enhanced. It can also eliminate the extra steps of checking the position of the implant after implantation. In one exemplary method, the position verification system 1400 is used during implantation to guide the tibial implant 10 into position on the tibia T. The surgeon attaches the arthroplasty tool 1420 with the position indicator 1403 to the tibial implant 10 (e.g., the surgeon positions the position indicator relative to the tibial implant). The surgeon then positions the tibial implant 10 relative to the proximal end PE of the tibia. The surgeon moves the tibial implant 10 into place on the proximal end PE of the tibia T (e.g., moves the tibial implant toward the tibia) using the arthroplasty tool 1420. The tracker 1410 tracks the position indicator 1403 to determine the position of the tibial implant 10. The tracker 1410 tracks the position of the position indicator 1403 as the position indicator moves with the arthroplasty tool 1420 and tibial implant 10 toward the tibia T. The tracker 1410 determines or extrapolates the position of the tibial implant 10 based on the position of the position indicator 1403. In this embodiment, the tracker 1410 knows the geometry of the tibial implant 10, the geometry of the arthroplasty tool 1420 (including the location of the position indicator 1403 relative to the arthroplasty tool) and the relative orientation and position of the tibial implant and arthroplasty tool when the arthroplasty tool is attached to the tibial implant. The tracker 1410 uses this information to determine the position of the tibial implant based the position of the position indicator 1403.

In one embodiment, the relevant information to determine the position of the tibial implant 10 (e.g., the geometry of the tibial implant, the geometry of the arthroplasty tool 1420 (including the location of the position indicator 1403 relative to the arthroplasty tool) and the relative orientation and position of the tibial implant and arthroplasty tool when the arthroplasty tool is attached to the tibial implant) can be stored in an implant database. In this embodiment, the surgeon may tell the tracker 1410 which tibial implant 10 and arthroplasty tool 1420 are being used via the user interface and access the appropriate information from the implant database. In another embodiment, the relevant information to determine the position of the tibial implant 10 is taught to the tracker 1410. In this embodiment, the tibial implant 10 is attached to the arthroplasty tool 1420 and then shown to the tracker 1410 which then determines (e.g., gathers) the necessary information. For example, the surgeon can calibrate the location of the tibial implant 10 relative to the arthroplasty tool 1420 using a variable region of the tibial implant. In this embodiment, the tacker 1410 may prompt to the surgeon to touch specific points on the tibial implant 10 and/or arthroplasty tool 1420 using the stylus 1402 to calibrate the tracker 1410 using surface matching algorithms.

After the tracker 1410 determines the position of the tibial implant 10, the process is generally the same as described in the embodiments above. The tracker 1410 determines or is informed of the position of the tibia T. The position of the tibial implant 10 is then compared relative to the position of the tibia T in order to verify whether or not the tibial implant is moving toward the correct position on the proximal end PE of the tibia. When using the position verification system 1400 during placement or implantation of the tibial implant 10 on the tibia T, the tracker 1410 or surgeon may compare the position of the tibial implant relative to the ideal position to verify that the tibial implant is moving toward (e.g., is inline with) the ideal position (as the tibial implant is implanted on the proximal end PE of the tibia T). If the tibial implant 10 is moving toward the ideal position, the surgeon can continue moving (e.g., inserting) the tibial implant 10 toward and into the tibia T, without making any adjustments. If the tibial implant is not moving toward the ideal position (e.g., is off track), the surgeon can make the necessary adjustments and corrections while moving the tibial implant 10 toward and into the tibia T. In this manner, the position verification system 1400 guides the tibial implant 10 toward the ideal position.

In another exemplary method, the arthroplasty tool 1420 is coupled or recoupled to the tibial implant 10 after the tibial implant is implanted on the tibia T to verify the position of the tibial implant relative to the tibia. In this embodiment, the surgeon attaches the arthroplasty tool 1420 with the position indicator 1403 to the tibial implant 10 implanted in the tibia T (e.g., the surgeon positions the position indicator relative to the tibial implant). The tracker 1410 tracks the position indicator 1403 to determine the position of the tibial implant 10. The tracker 1410 tracks or locates the position of the position indicator 1403 mounted on the arthroplasty tool 1420 that is coupled to the tibial implant 10. The tracker 1410 locates the position indicator 1403 to determine or extrapolate the position of the tibial implant 10. As explained above, the tracker 1410 knows the geometry of the tibial implant 10, the geometry of the arthroplasty tool 1420 (including the location of the position indicator 1403 relative to the arthroplasty tool) and the relative orientation and position of the tibial implant and arthroplasty tool when the arthroplasty tool is attached to the tibial implant. The tracker 1410 uses this information to determine the position of the tibial implant 10 based the position of the position indicator 1403.

Figure 33:
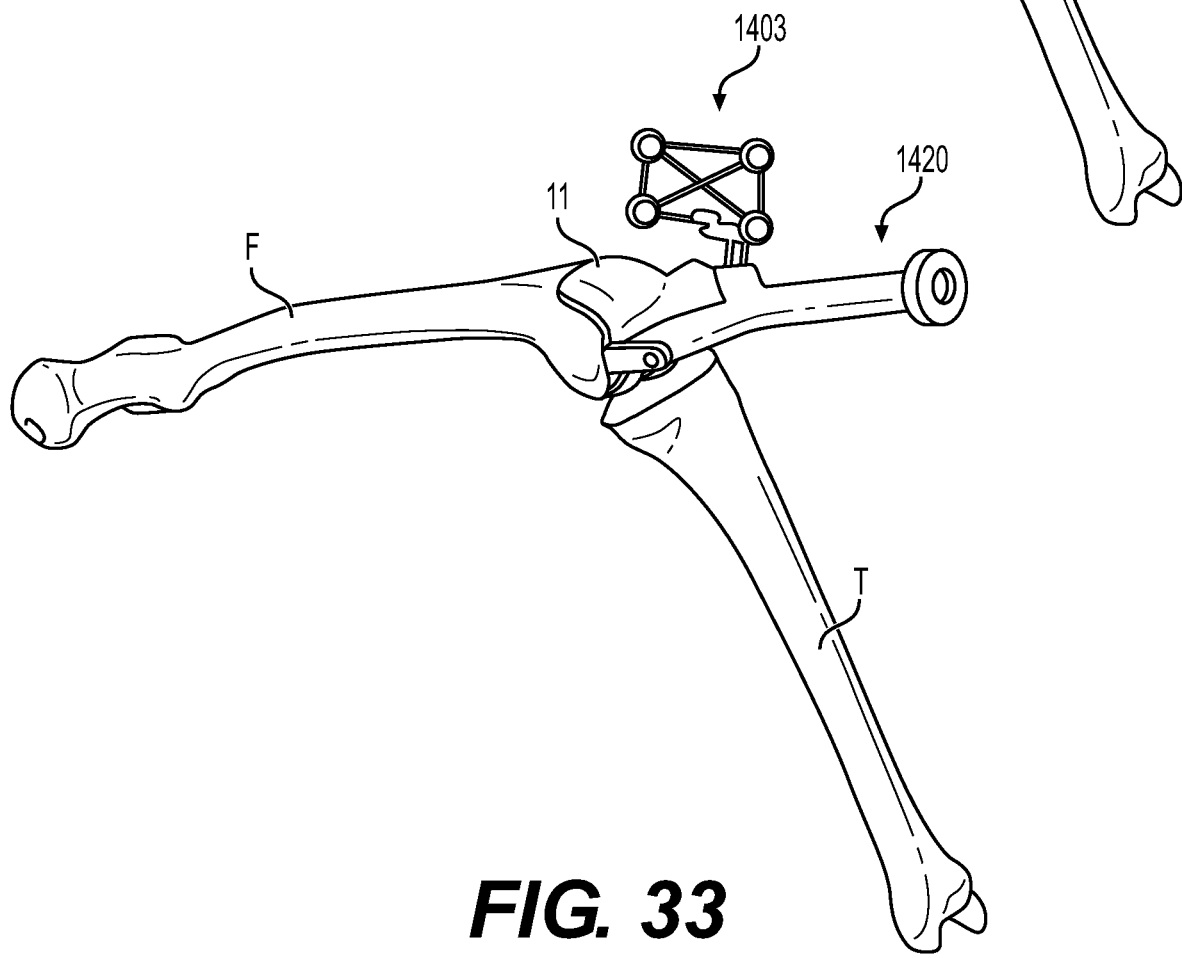
FIG. 33 is a perspective of the position indicator of FIG. 32 secured to a femoral installation tool attached to a femoral implant in order to verify the position of the femoral implant relative to the distal end of the femur.

After the tracker 1410 determines the position of the tibial implant 10, the process is generally the same as described in the embodiments above. The tracker 1410 determines or is informed of the position of the tibia T. The position of the tibial implant 10 is then compared relative to the position of the tibia T in order to verify whether or not the tibial implant is correctly positioned on the proximal end PE of the tibia. When using the position verification system 1400 to verify the position of the tibial implant 10 relative to the tibia T after the implant is implanted, the tracker 1410 or surgeon may compare the position of the tibial implant relative to the ideal position to verify or confirm that the tibial implant is in the correct position on the tibia. If the position of the tibial implant 10 relative to the tibia T aligns with the ideal position, the tibial implant is correctly position and the surgeon can proceed with the rest of the surgery. If the position of the position of the tibial implant 10 relative to the tibia T does not align with the ideal position, the surgeon adjusts the position of the implant as needed before proceeding with the surgery. After the position of the tibial implant 10 is verified, the arthroplasty tool 1420 can be removed or detached from the implant. These same processes can be used to determine the position of other implants relative to a bone. For example, as shown in FIG. 33, the same process can be used to verify the position of a femoral implant 11 by tracking the position indicator 1403 of the position verification system 1400 mounted on an arthroplasty tool 1420 coupled to the femoral implant.

Figure 34:
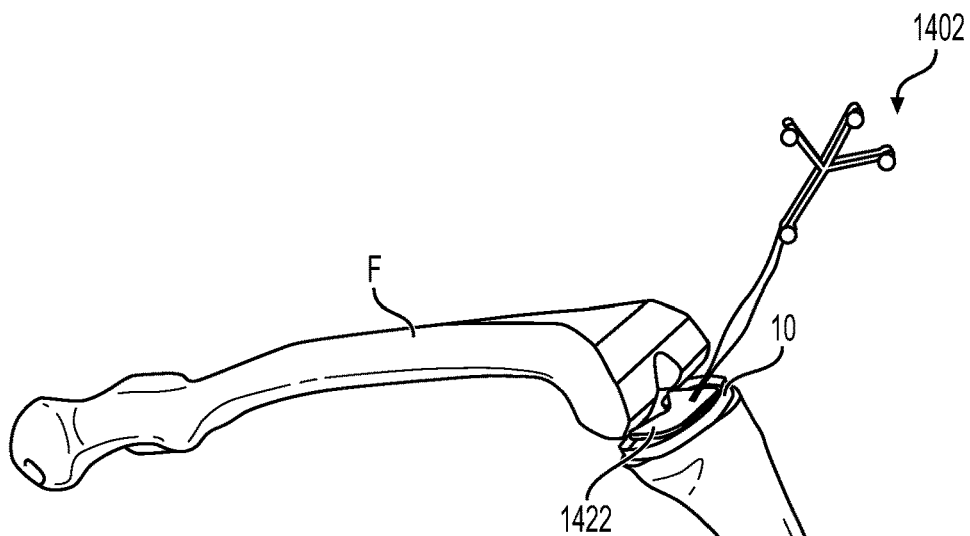
FIG. 34 is a perspective of the position indicator of FIG. 26 secured to a tibial cover attached to a tibial implant in order to verify the position of the tibial implant relative to the proximal end of the tibia.
Figure 35:
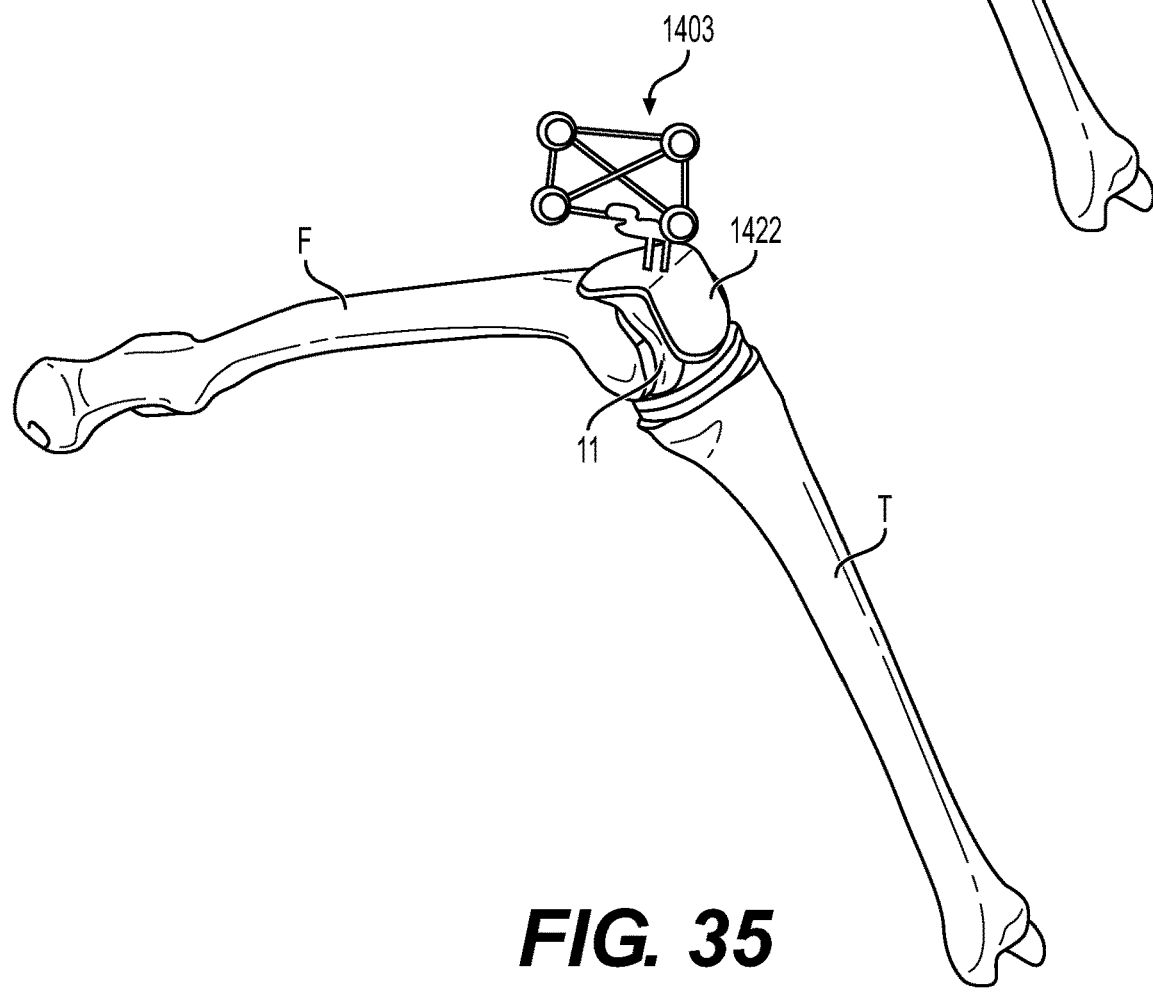
FIG. 35 is a perspective of the position indicator of FIG. 32 secured to a femoral cover attached to a femoral implant in order to verify the position of the femoral implant relative to the distal end of the femur.
Figure 36:
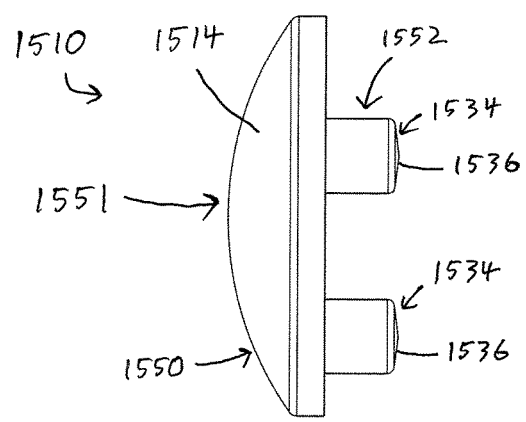
FIG. 36 is a side elevation of a patella implant according to another embodiment of the present disclosure
Figure 37:
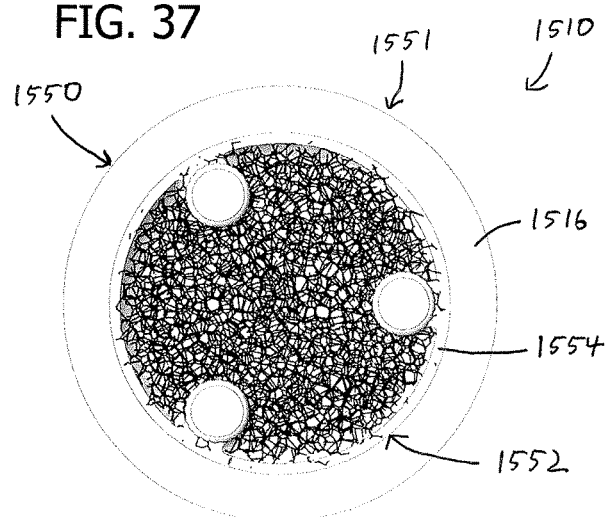
FIG. 37 is a bottom plan view thereof.
Figure 38:
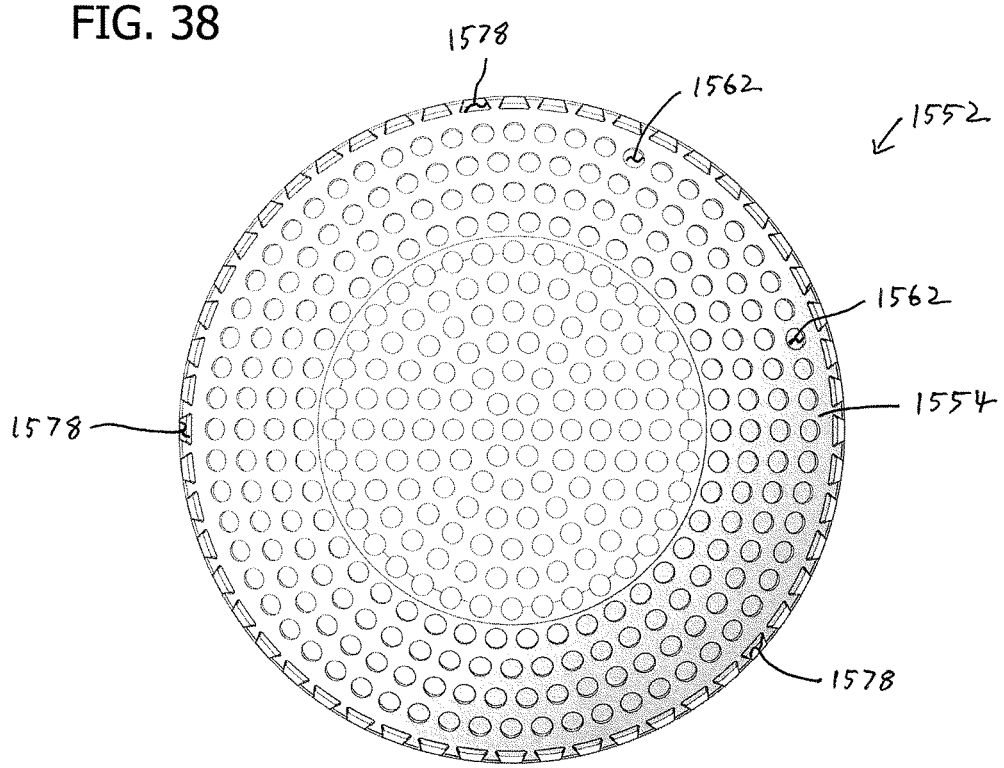
FIG. 38 is a top plan view of a base of the patella implant of FIG. 36.
Figure 39:
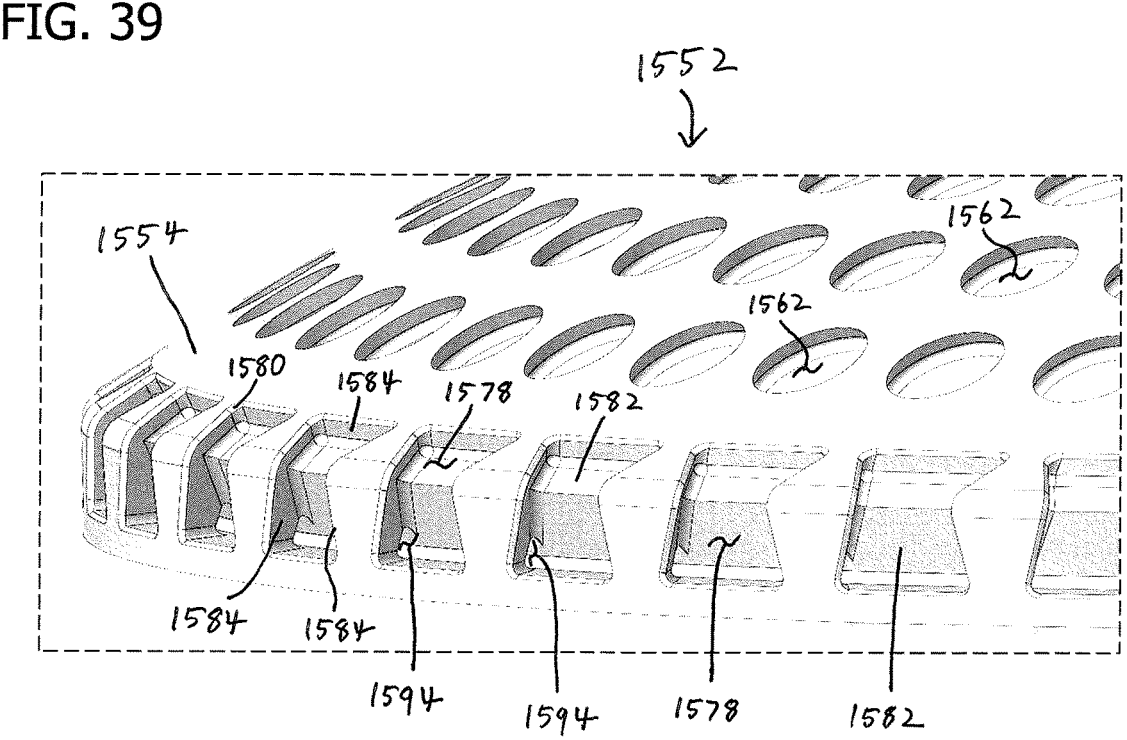
FIG. 39 is an enlarged, fragmentary side perspective of the base of the patella implant of FIG. 36.
Figure 40:
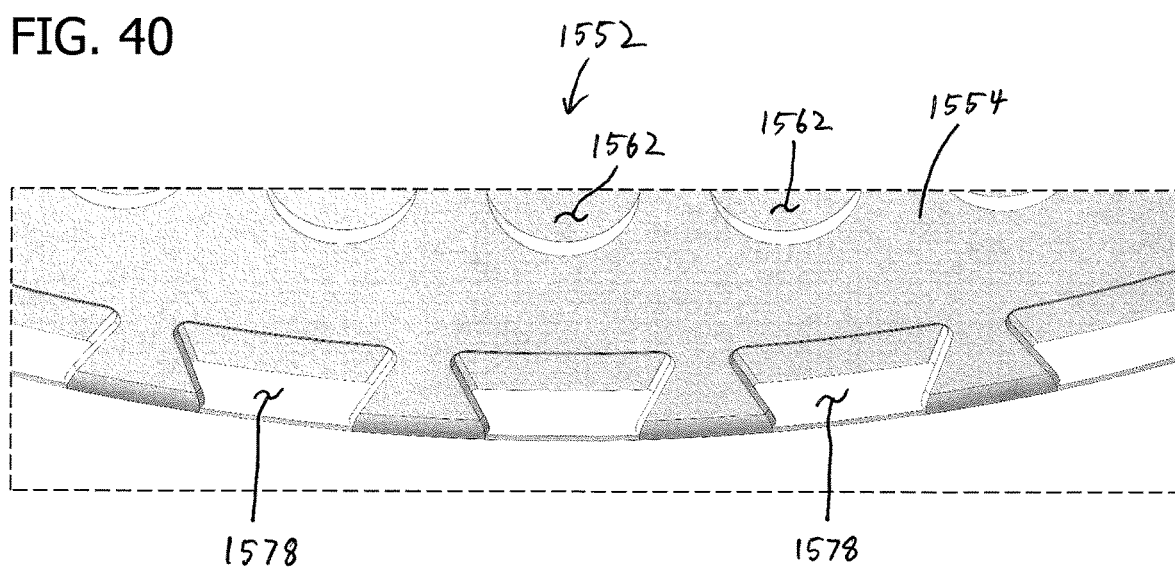
FIG. 40 is an enlarged, fragmentary top perspective of the base of the patella implant of FIG. 36.
Figure 41:
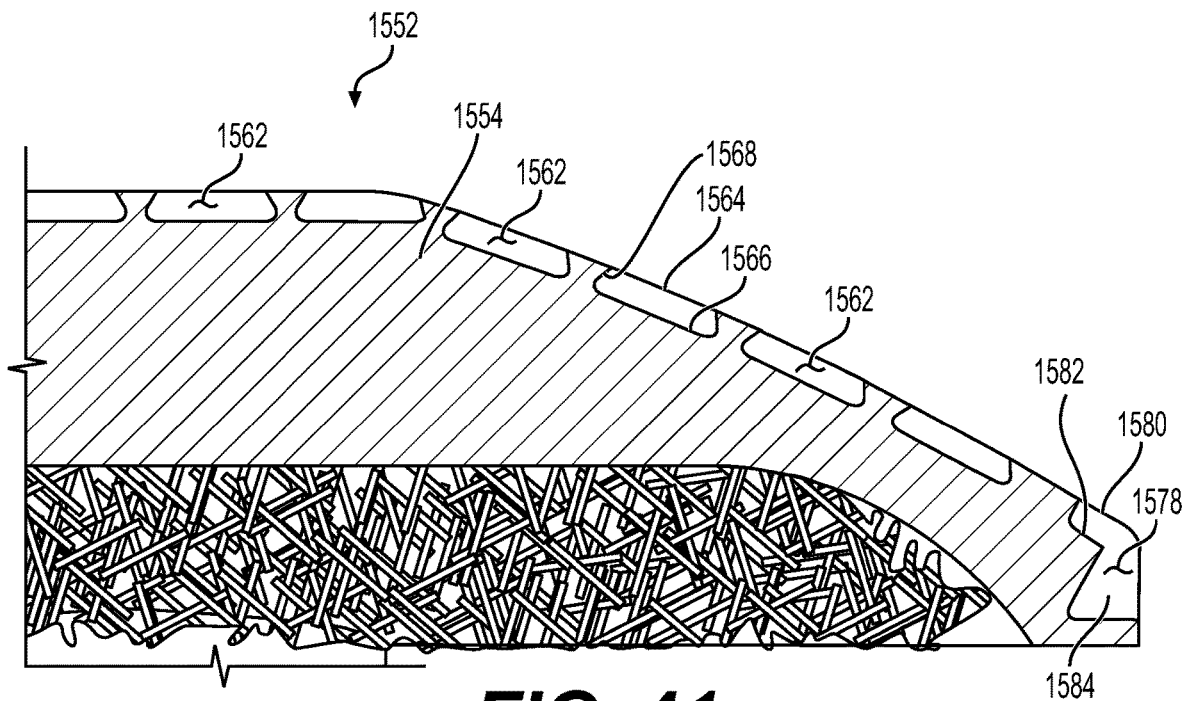
FIG. 41 is an enlarged, fragmentary cross-section of the base of the patella implant of FIG. 36.

Referring to FIG. 34, in one embodiment, the position verification system 1400 includes an implant cover 1422. The implant cover 1422 is configured to releasably couple to the implant. The implant cover 1422 is sized and shaped to couple to the type of implant the cover corresponds to. For example, an implant cover 1422 for a tibial implant 10 (FIG. 34) may be similar to an insert and be sized and shaped to be secured in the insert receiving space 22 of the implant. In another embodiment, the implant cover 1422 is for a femoral implant 11 (FIG. 35) and is sized and shaped to be secure over the implant. When the implant cover 1422 is coupled to the implant, the implant cover is rigidly and immovable secured to the implant. Preferably, the implant cover 1422 generally fits over the articulation surface of the implant. Generally, the tracker 1410 uses the position of the implant cover 1422 to determine the position of the implant. In this embodiment, the position indicator 1402, 1403 is rigidly coupled to the implant cover 1422. FIG. 34 shows one type of position indicator 1402, the stylus, coupled to the implant cover 1422 for a tibial implant 10 and FIG. 35 shows another type of position indicator 1403, the array, coupled to the implant cover for a femoral implant 11. Other types of position indicators may be coupled to the implant covers. In one embodiment, the implant cover 1422 may be coupled to the implant after the implant is placed on the bone to verify the position of the implant. In another embodiment, the implant cover 1422 may be coupled to the implant while the implant is being implanted on the bone to guide the implantation.

Still referring to FIG. 34, in an exemplary method of operation, the position verification system 1400 is configured to track the position indicator 1402 coupled to the implant cover 1422 to determine the position of the tibial implant 10. In this embodiment, the position verification system 1400 can provide feedback to the surgeon regarding the placement of the tibial implant 10 both during the implantation and after the implantation is completed. In one exemplary method, the position verification system 1400 is used during implantation to guide the tibial implant 10 into position on the tibia T. The surgeon attaches the implant cover 1422 with the position indicator 1402 to the tibial implant 10 (e.g., the surgeon positions the position indicator relative to the tibial implant). The surgeon also attaches the arthroplasty tool 1420 to the tibial implant 10. In one embodiment, the implant cover 1422 is disposed between the tibial implant 10 and the arthroplasty tool 1420 and moves with the arthroplasty tool. The surgeon then positions the tibial implant 10 relative to the proximal end PE of the tibia. The surgeon moves the tibial implant 10 into place on the proximal end PE of the tibia T (e.g., moves the tibial implant toward the tibia) using the arthroplasty tool 1420. The tracker 1410 tracks the position indicator 1402 to determine the position of the tibial implant 10. The tracker 1410 tracks the position of the position indicator 1402 as the position indicator moves with the implant cover 1422, the arthroplasty tool 1420 and the tibial implant 10 toward the tibia T. The tracker 1410 tracks the position indicator 1402 to determine the position of the implant cover 1422 and to determine or extrapolate the position of the tibial implant 10 coupled thereto. In this embodiment, the tracker 1410 knows the geometry of the tibial implant 10, the geometry of the implant cover 1422 (including the location of the position indicator 1402 relative to the implant cover) and the relative orientation and position of the tibial implant and implant cover when the implant cover is attached to the tibial implant. The tracker 1410 uses this information to determine the position of the tibial implant 10 based the position of the position indicator 1402. This relevant information to determine the position of the tibial implant 10 known by the tracker 1410 may be stored in an implant database and/or taught to the tracker, as explained above.

After the tracker 1410 determines the position of the tibial implant 10, the process is generally the same as described in the embodiments above. The tracker 1410 determines or is informed of the position of the tibia T. The position of the tibial implant 10 is then compared relative to the position of the tibia T in order to verify whether or not the tibial implant is moving toward the correct position on the proximal end PE of the tibia. When using the position verification system 1400 during placement or implantation of the tibial implant 10 on the tibia T, the tracker 1410 or surgeon may compare the position of the tibial implant relative to the ideal position to verify that the tibial implant is moving toward (e.g., is inline with) the ideal position (as the tibial implant is implanted on the proximal end PE of the tibia T). If the tibial implant 10 is moving toward the ideal position, the surgeon can continue moving (e.g., inserting) the tibial implant 10 toward and into the tibia T, without making any adjustments. If the tibial implant is not moving toward the ideal position, the surgeon can make the necessary adjustments and corrections while moving the tibial implant 10 toward and into the tibia T. In this manner, the position verification system 1400 guides the tibial implant 10 toward the ideal position.

In another exemplary method, the implant cover 1422 is coupled to the tibial implant 10 after the tibial implant is implanted on the tibia T to verify the position of the tibial implant relative to the tibia. In this embodiment, the surgeon attaches the implant cover 1422 with the position indicator 1402 to the tibial implant 10 implanted in the tibia T (e.g., the surgeon positions the position indicator relative to the tibial implant). The tracker 1410 tracks the position indicator 1402 to determine the position of the tibial implant 10. The tracker 1410 tracks or locates the position of the position indicator 1402 mounted on the implant cover 1422 that is coupled to the tibial implant 10. The tracker 1410 locates the position indicator 1402 to determine or extrapolate the position of the tibial implant 10. As explained above, the tracker 1410 knows the geometry of the tibial implant 10, the geometry of the implant cover 1422 (including the location of the position indicator 1402 relative to the implant cover) and the relative orientation and position of the tibial implant and implant cover when the implant cover is attached to the tibial implant. The tracker 1410 uses this information to determine the position of the tibial implant 10 based the position of the position indicator 1402.

After the tracker 1410 determines the position of the tibial implant 10, the process is generally the same as described in the embodiments above. The tracker 1410 determines or is informed of the position of the tibia T. The position of the tibial implant 10 is then compared relative to the position of the tibia T in order to verify whether or not the tibial implant is correctly positioned on the proximal end PE of the tibia. When using the position verification system 1400 to verify the position of the tibial implant 10 relative to the tibia T after the implant is implanted, the tracker 1410 or surgeon may compare the position of the tibial implant relative to the ideal position to verify or confirm that the tibial implant is in the correct position on the tibia. If the position of the tibial implant 10 relative to the tibia T aligns with the ideal position, the tibial implant is correctly position and the surgeon can proceed with the rest of the surgery. If the position of the position of the tibial implant 10 relative to the tibia T does not align with the ideal position, the surgeon adjusts the position of the implant as needed before proceeding with the surgery. After the position of the tibial implant 10 is verified, the implant cover 1422 can be removed or detached from the implant. These same processes can be used to determine the position of other implants relative to a bone. For example, as shown in FIG. 35, the same process can be used to verify the position of a femoral implant 11 by tracking the position indicator 1403 of the position verification system 1400 mounted on an implant cover 1422 coupled to the femoral implant.

The order of execution or performance of the operations in embodiments of the aspects of the present disclosure described herein are not essential, unless specifically stated or indicated otherwise. That is, the operations may be performed in any order and/or simultaneously, and the embodiments of the aspects of the disclosure may include additional or fewer operations than those disclosed herein. For example, it is contemplated that executing or performing a particular operation before, contemporaneously with, or after another operation is within the scope of the present disclosure.

The tracking systems and methods described herein can also be used to determine the position of other elements and objects besides implants. In one embodiment, the tracking systems and methods described herein are used to determine the position of the bone the implant is attached to. For example, in one embodiment similar to the embodiments shown in FIGS. 30 and 31, the surgeon may brush or move the position indicator 1402 (e.g., the tip of the stylus) over all or a portion of the tibia T or proximal end PE thereof to determine the position of the tibia.

Referring to FIGS. 36-46, a patella implant according to another embodiment of the present disclosure is generally indicated at reference numeral 1510. The patella implant 1510 is sized and shaped to be implanted on the backside of a patella of a patient. The patella implant 1510 includes a proximal or articulating surface 1514 (e.g., proximal end) and an opposite distal surface 1516 (e.g., distal end). The distal surface 1516 is configured to engage the backside of the patella. The articulating surface 1514 has a partial dome shape. The patella implant 1510 includes a porous region, as discussed above. In particular, the distal surface 1516 is porous (e.g., is a porous region). In the illustrated embodiment, a portion of the distal surface 1516 is porous, although in other embodiments the entire distal surface 1516 may be porous. The portion of the distal surface 1516 that is porous is generally centrally located on the distal surface and spaced apart the peripheral edge of the distal surface. The porous region has a generally circular shape disposed within the larger circular shape of the distal surface 1516. As shown in the illustrated embodiment, the porous region comprises generally hexagonal struts coupled together to form a lattice, although any suitable porous structure is within the scope of the present disclosure. As mentioned above the porosity of the distal surface 1516 allows the patella implant 1510 be inserted into or implanted on the patella without the cement conventionally used in knee arthroplasties, reducing procedural times, cement related complications and surgeon stress.

The patella implant 1510 includes a cap 1550 and a base or anchor 1552 coupled or secured together. The cap 1550 is mounted on the base 1552. The cap 1550 defines (e.g., includes) the articulating surface 1514. The cap 1550 also defines a portion of the distal surface 1516. In the illustrated embodiment, the portion of the distal surface 1516 defined by the cap 1550 is not porous. The cap 1550 includes a shroud or cover 1551. The shroud 1551 includes the articulating surface 1514. The shroud 1551 has a partial dome shape and defines an interior or cavity sized and shaped to receive a portion of the base 1552, as described in more detail below. The shroud 1551 surrounds (e.g., covers) the proximal end portion of the base 1552. The cap 1550 can be made out of a polymeric material or any other suitable material.

Figure 48:
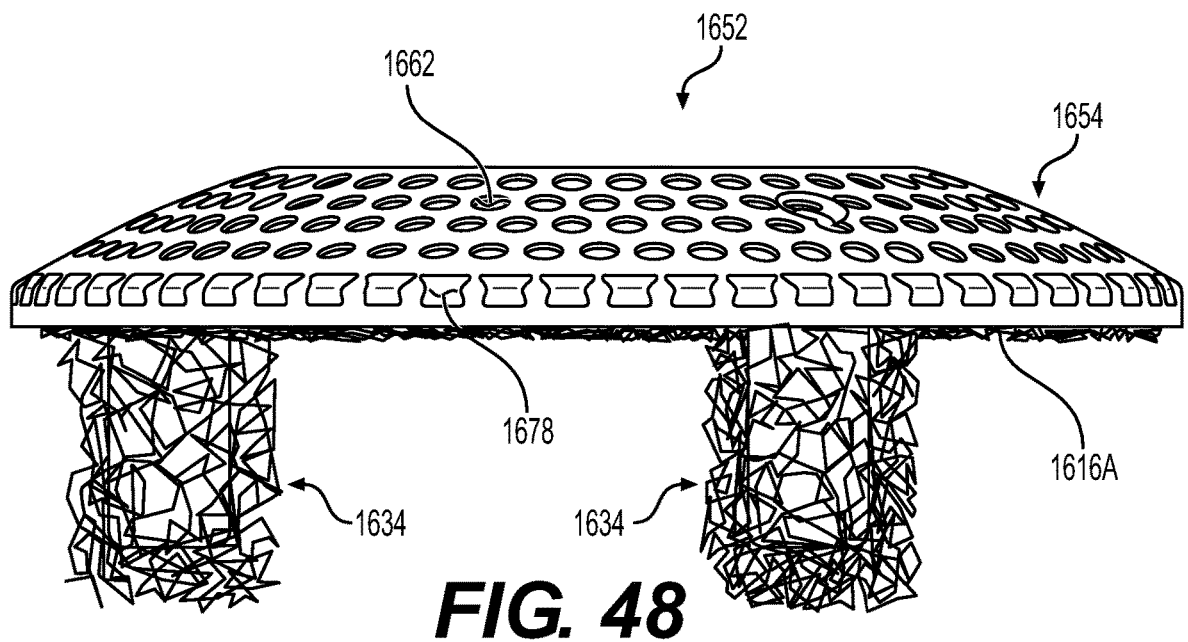
FIG. 48 is a side elevation of the base of FIG. 47.
Figure 49:
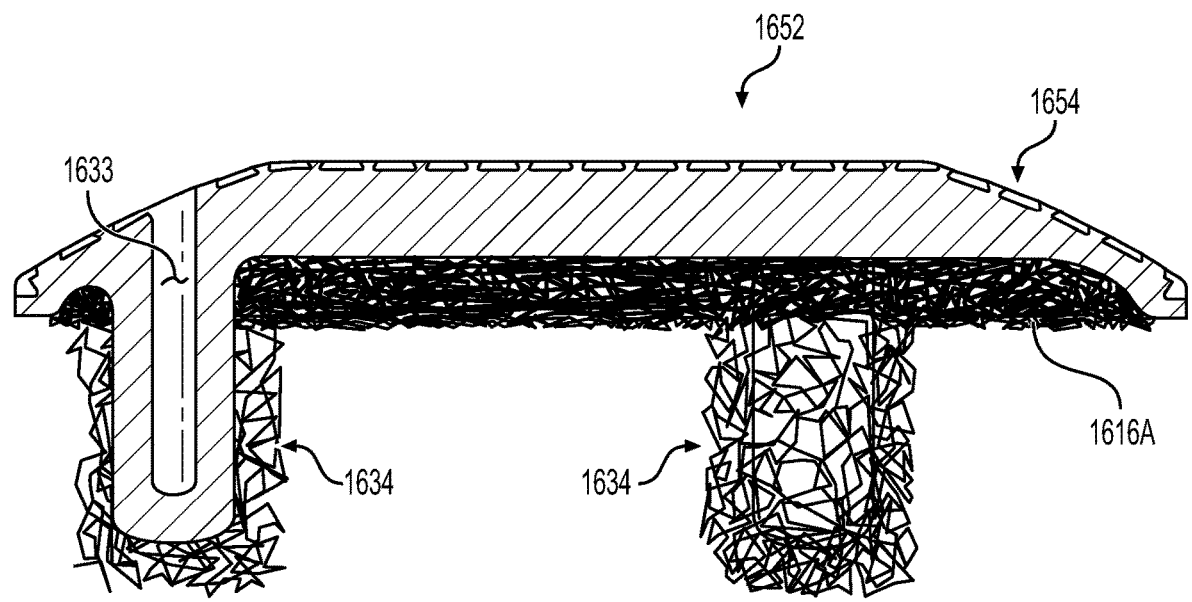
FIG. 49 is a cross-section of the base of FIG. 47.

The base 1552 is configured to be attached to the backside of the patella of the patient. The base 1552 includes at least one (e.g., a plurality of) anchoring projections 1534, similar to the anchoring projections discussed above. The anchoring projections 1534 are configured to be inserted into the backside of the patella. In the illustrated embodiment, the patella implant 1510 includes three anchoring projections 1534, although more or fewer anchoring projections are within the scope of the present disclosure. Each anchoring projection 1534 extends generally distally from the distal surface 1516. Specifically, the anchoring projections 1534 extend from the cap support 1554, which is described in more detail below. In this embodiment, each anchoring projection 1534 is cylindrical (e.g., has a cylinder shape) with a shallow conical distal tip 1536. The anchoring projection 1534 is also solid, although in other embodiment the anchoring projection can be hollow. In addition, the base 1552 defines a portion of the distal surface 1516. In the illustrated embodiment, the portion of the distal surface 1516 defined by the base 1552 is porous (see FIG. 48). This permits the ingrowth of bone into the base 1552 to further secure the base to the patella after the base is attached to the patella. Accordingly, the distal surface 1516 faces and engages the patella when the patella implant 1510 is attached to the patella. Thus, the porous region of the base 1552 is configured to face the backside of the patella. The base 1552 may be made out of a metal or any other suitable material.

The cap 1550 and the base 1552 are coupled (e.g., configured to be coupled) together to form the patella implant 1510. The base 1552 includes a base support 1554 mounted to the cap 1550 (e.g., configured to attach to the cap). Specifically, the base support 1554 is mounted to the shroud 1551 of the cap 1550. The base support 1554 is disposed in the interior of the shroud 1551, which is sized and shaped to receive the base support. To secure the cap 1550 and the base 1552 together, the cap and base includes a plurality of interconnection or interdigitation members. The interconnection members of the cap 1550 and the base 1552 mate and interlock with one another to secure the cap and the base to each other. The plurality of interconnection members of the cap 1550 and the base 1552 increase the resistance of the cap and the base from dissociation from one another and minimize the occurrence and intensity of micro-motion, over conventional patella implants. The cap support 1554 also provides rigidity for the patella implant 1510 and a mounting platform for the porous structure (e.g., hexagonal struts) and the anchoring projections 1534.

Figure 42:
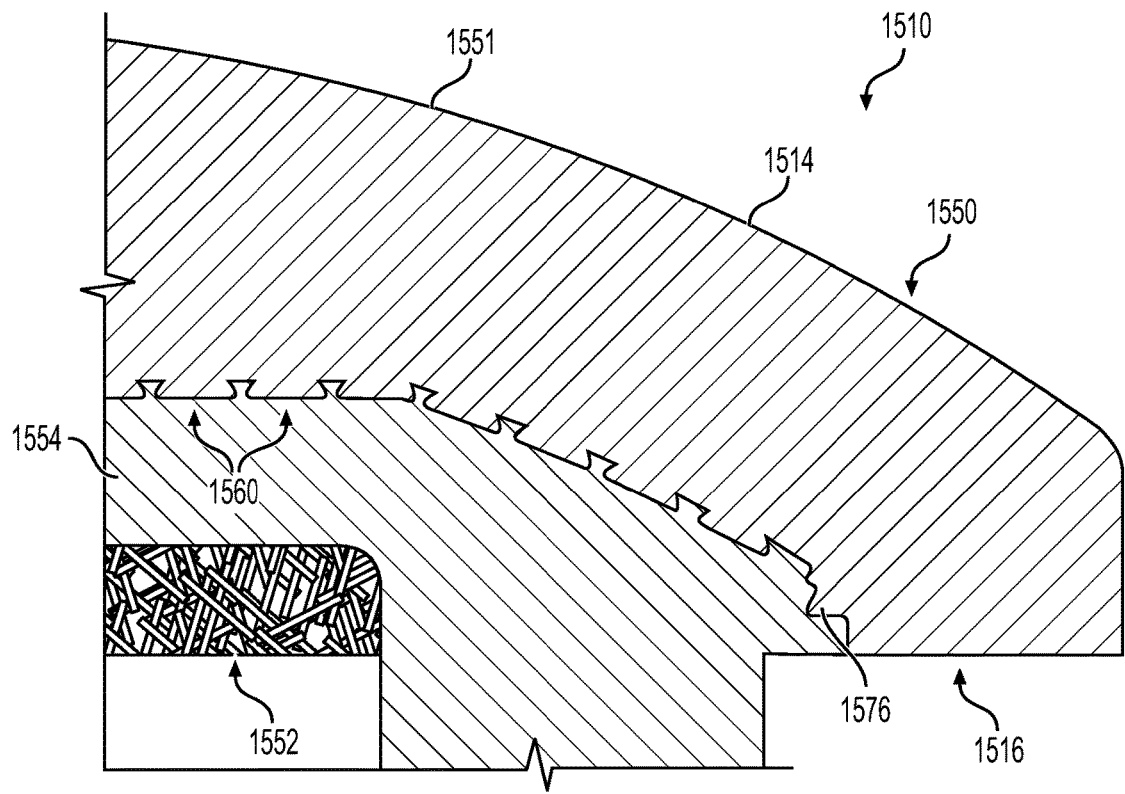
FIG. 42 is an enlarged, fragmentary cross-section of the patella implant of FIG. 36, showing a cap of the patella implant connected to the base.
Figure 43:
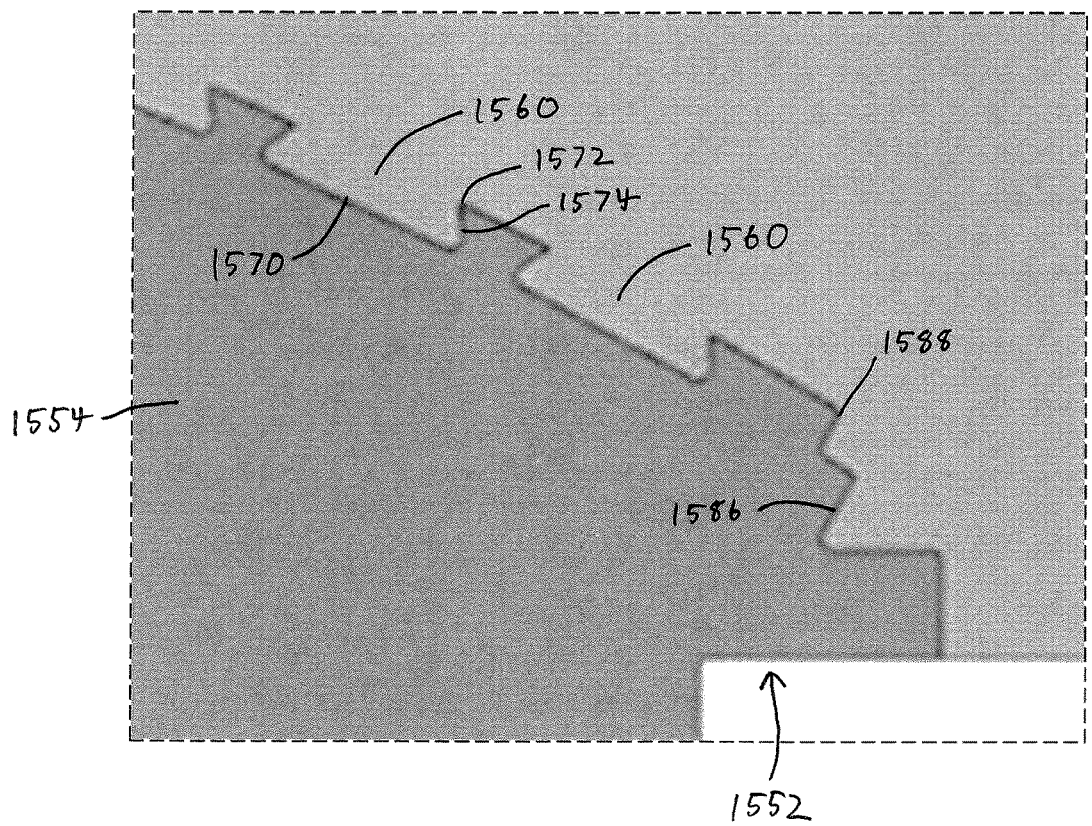
FIG. 43 is an enlarged view of FIG. 42.
Figure 44:
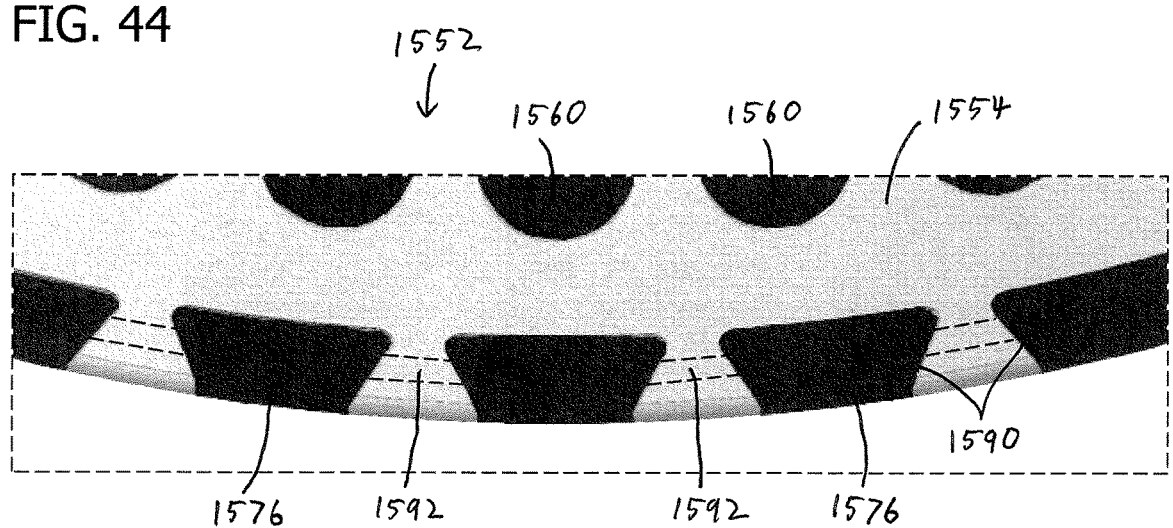
FIG. 44 is an enlarged, fragmentary top perspective of the patella implant of FIG. 36, with portions of the cap hidden from view to more clearly show the interconnection of connection members of the cap with the base

Referring to FIGS. 38-46, the interconnection members of the cap 1550 include a plurality of first connection members 1560 (e.g., first projections). Likewise, the interconnection members of the base 1552 include a plurality of first connection recesses 1562. Each first connection member 1560 of the cap 1550 is disposed (e.g., is configured to be disposed) in a corresponding one of the first connection recesses 1562 of the base 1552 to mount and secure the cap to the base (e.g., the first connection recesses receive or are configured to receive the first connection members). The first connection members 1560 are spaced apart and extend into the interior of the shroud 1551 from an interior surface thereof. The cap support 1554 includes (e.g., defines) the first connection recesses 1562. The first connection recesses 1562 extend generally inward from an exterior surface of the cap support 1554. The exterior surface of the cap support 1554 and the interior surface of the shroud 1551 correspond to and engage one another (FIG. 42). In the illustrated embodiment, the exterior and interior surfaces have generally partial dome shapes.

Each first connection member 1560 of the cap 1550 interlocks (e.g., is configured to interlock) with a corresponding one of the first connection recesses 1562 of the base 1552. Specifically, the size and shapes of the first connection member 1560 and the first connection recesses 1562 correspond to each other. The first connection recesses 1562 are each undercut (in one or more directions) so as to prevent withdrawal of the first connection members 1560 disposed therein. In the illustrated embodiment, each first connection recesses 1562 includes a recess mouth 1564 and a recess base or floor 1566 opposite the recess mouth. The recess mouth 1564 (e.g., an area and/or a diameter thereof) is smaller or narrower than the recess base 1564 (e.g., an area and/or a diameter thereof). Each first connection recess 1562 is at least partially defined by at least one cap support tapered surface 1568 (e.g., first cap support tapered surface). In the illustrated embodiment, the first connection recess 1562 includes one cap support tapered surface 1568, although other configurations are within the scope of the present disclosure. The cap support tapered surface 1568 tapers outward as the cap support tapered surface extends inward. In the illustrated embodiment, the cap support tapered surface 1568 extends inward from the recess mouth 1566 (e.g., exterior surface of the cap support 1554). Correspondingly, in the illustrated embodiment, each first connection member 1560 includes a free or connection end 1570 opposite an attached end 1572. The attached end 1572 is attached to the shroud 1551 (e.g., the interior surface thereof). The attached end 1572 (e.g., a cross-sectional area and/or a diameter thereof) is smaller or narrower than the connection end 1570 (e.g., a cross-sectional area and/or diameter thereof). The attached end 1572 of each first connection member 1560 corresponds to the size and shape of the recess mouth 1564 of the corresponding first recess member 1562. Likewise, the connection end 1570 of each first connection member 1560 corresponds to the size and shape of the recess base 1566 of the corresponding first recess member 1562. Each first connection member 1560 includes at least one connection member tapered surface 1574 (e.g., first connection member tapered surface). In the illustrated embodiment, the first connection member 1560 includes one connection member tapered surface 1574, although other configurations are within the scope of the present disclosure. The connection member tapered surface 1574 is disposed between the connection end 1570 and the attached end 1572. The connection member tapered surface 1574 tapers outward as the connection member tapered surface extends away from the shroud 1551 (e.g., the interior surface of the shroud). In the illustrated embodiment, the connection member tapered surface 1574 extends from the shroud 1551 (e.g., the interior surface thereof). The connection member tapered surface 1574 and the cap support tapered surface 1568 engage (e.g., are configured to engage) each other to connect the cap 1550 and the base 1552 together and to inhibit the withdrawal of the respective first connection members 1560 from the respective first connection recesses 1562. In the illustrated embodiment, the first connection member 1560 and the first connection recess 1562 have generally truncated conical shapes.

Still referring to FIGS. 38-44, the interconnection members of the cap 1550 further include a plurality of second connection members 1576 (e.g., second projections). Likewise, the interconnection members of the base 1552 include a plurality of second connection recesses 1578. Each second connection member 1576 of the cap 1550 is disposed (e.g., configured to be disposed) in a corresponding one of the second connection recesses 1578 of the base 1552 to mount and secure the cap to the base (e.g., the second connection recess receive or are configured to receive the second connection members). The second connection members 1576 are spaced apart and extend into (e.g., extend radially into) the interior of the shroud 1551 from the interior surface thereof. The second connection members 1576 are disposed along a peripheral edge (e.g., an interior peripheral edge) of the cap 1550 (e.g., shroud 1551). The second connection members 1576 are spaced apart circumferentially along the peripheral edge of the shroud 1551. Accordingly, the second connection members 1576 are generally disposed outward (e.g., radially outward) of the first connection members 1560 (e.g., the first connection members are disposed generally inward of the second connection members). The cap support 1554 includes the second connection recesses 1578. The second connection recesses 1578 are disposed along a peripheral edge (e.g., an outer peripheral edge) of the cap support 1554. The second connection recesses 1578 are spaced apart circumferentially along the peripheral edge of the cap support 1554. Accordingly, the second connection recesses 1578 are generally disposed outward (e.g., radially outward) of the first connection recesses 1562 (e.g., the first connection recesses are disposed generally inward of the second connection recesses).

Each second connection member 1576 of the cap 1550 interlocks (e.g., is configured to interlock) with a corresponding one of the second connection recesses 1578 of the base 1552. Specifically, the size and shapes of the second connection members 1576 and the second connection recesses 1578 correspond to each other. As with the first connection recesses 1562, the second connection recesses 1578 are each undercut (in one or more directions) so as to prevent withdrawal of the second connection members 1576 disposed therein. As is apparent, the second connection members 1576 have a different shape than the first connection member 1560. Likewise, the second connection recesses 1578 have a different shape than the first connection recesses 1562.

In the illustrated embodiment, each second connection recesses 1578 includes a recess mouth 1580 and a recess base or floor 1582 opposite the recess mouth. In the illustrated embodiment, the recess mouth 1580 has a generally hour-glass shape. The hour-glass shape of the recess mouth 1580 is generally bent at a corner of the cap support 1554. Likewise, the recess base 1582 has a generally hour-glass shape that is also bent. The recess mouth 1580 (e.g., an area thereof) is smaller or narrower than the recess base 1582 (e.g., an area thereof). Each second connection recess 1578 is at least partially defined by a plurality of cap support tapered surfaces 1584 (e.g., second cap support tapered surfaces). Each cap support tapered surface 1568 tapers outward as the cap support tapered surface extends inward. The cap support tapered surfaces 1568 taper outward in multiple different outward directions. In the illustrated embodiment, each cap support tapered surfaces 1584 extends inward (e.g., generally radially inward) from the recess mouth 1580 (e.g., exterior surface of the cap support 1554). Each cap support tapered surface 1584 defines a side of the second connection recess 1578. Correspondingly, in the illustrated embodiment, each second connection member 1576 includes a free or connection end 1586 opposite an attached end 1588. The attached end 1588 is attached to the shroud 1551 (e.g., the interior surface thereof). The attached end 1588 (e.g., a cross-sectional area thereof) is smaller or narrower than the connection end 1586 (e.g., a cross-sectional area thereof). The attached end 1588 of each second connection member 1576 corresponds to the size and shape of the recess mouth 1580 of the corresponding second recess member 1578. Likewise, the connection end 1586 of each second connection member 1576 corresponds to the size and shape of the recess base 1582 of the corresponding second recess member 1578. Each second connection member 1576 includes a plurality of connection member tapered surfaces 1590 (e.g., second connection member taper surfaces). Each connection member tapered surface 1590 is disposed between the connection end 1586 and the attached end 1588. Each connection member tapered surface 1590 tapers outward as the connection member tapered surface extends into the cap support 1554 (e.g., the exterior surface of the cap support). In the illustrated embodiment, each connection member tapered surface 1590 extends from the exterior surface of the cap support 1554. Each connection member tapered surface 1590 engages a corresponding cap support tapered surface 1584 to connect the cap 1550 and the base 1552 together and to inhibit the withdrawal of the respective second connection members 1576 from the respective second connection recesses 1578.

Figure 45:
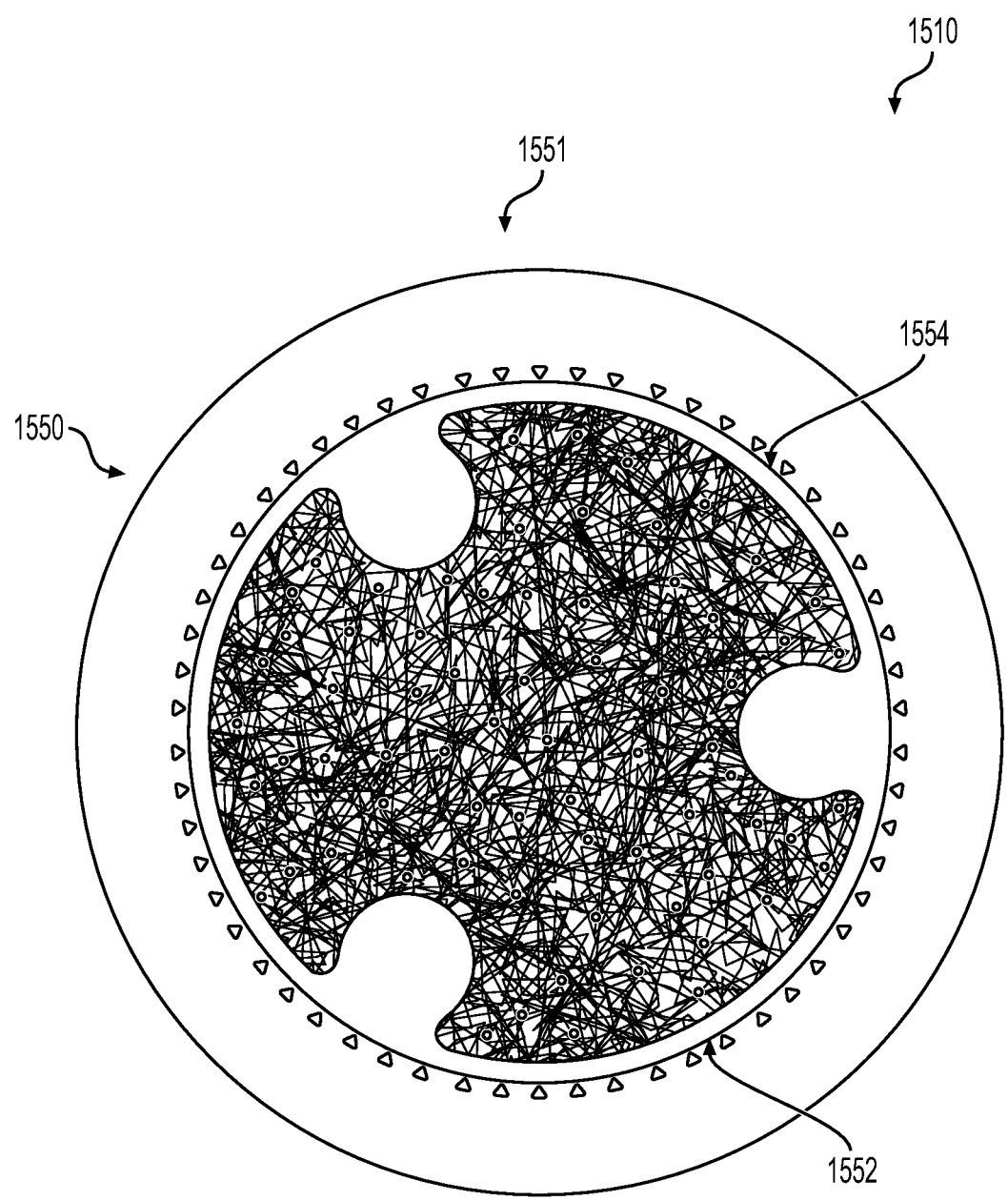
FIG. 45 is cross-section of the patella implant of FIG. 36.
Figure 46:
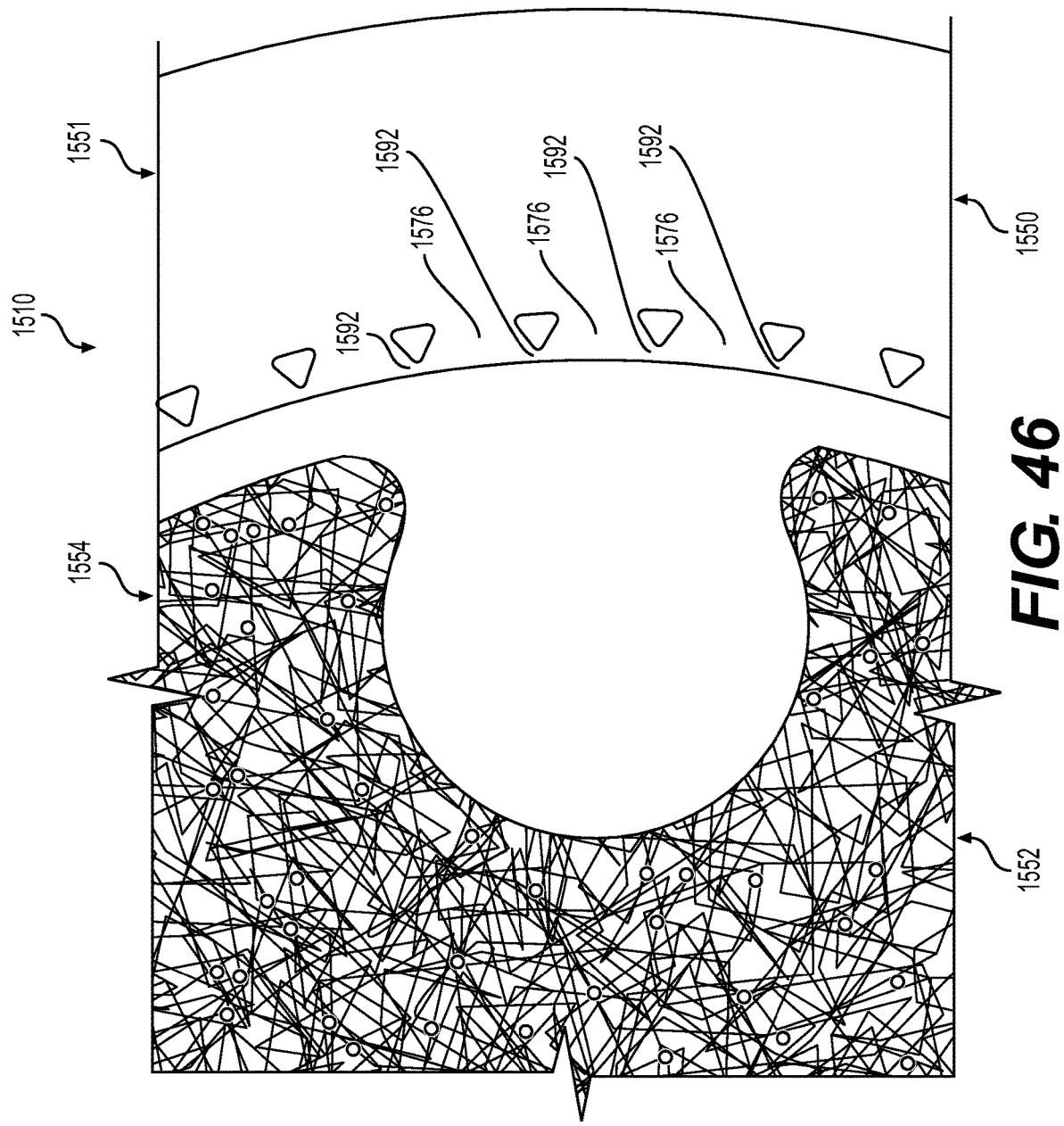
FIG. 46 is an enlarged view of FIG. 45.
Figure 47:
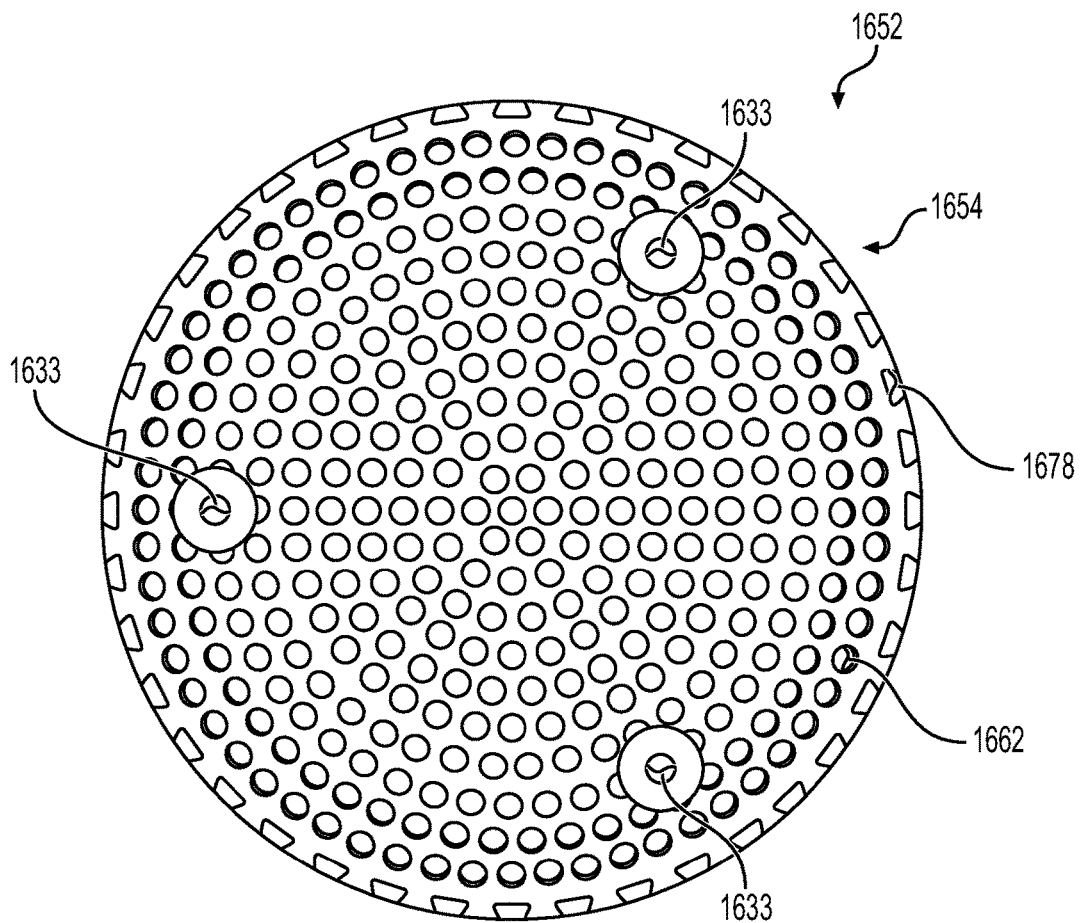
FIG. 47 is a top plan view of a base for a patella implant according to another embodiment of the present disclosure.

Referring to FIGS. 39 and 44-46, the interconnection members of the cap 1550 further includes a plurality of interconnecting struts 1592. Each interconnecting strut 1592 extends between and interconnects two adjacent second connection members 1576. Likewise, the interconnection members of the base 1552 further include a plurality of interconnecting voids 1594. Each interconnecting void 1594 extends between and interconnects two adjacent second connection recesses 1578. Each interconnecting strut 1592 of the cap 1550 is disposed (e.g., configured to be disposed) in a corresponding one of the interconnecting voids 1594 of the base 1552 to further mount and secure the cap to the base (e.g., the interconnecting voids receive or are configured to receive the interconnecting struts). Accordingly and as illustrated in FIG. 45, the interconnecting struts 1592 and the second connection members 1576 combine to form a continuous loop at encircles a portion of the base 1552 (e.g., the cap support 1554). The continuous loop formed by the interconnecting struts 1592 and the second connection members 1576 is constrained from moving relative to the base 1552 by the cap support 1554. Thus, like the first connection members 1560 and the second connection members 1576 alone, the continuous loop formed by interconnecting struts 1592 and the second connection members secure and interlock the cap 1550 and the base 1552 together and inhibit movement of the cap relative to the base.

Other configurations of the interconnecting members of the cap 1550 and the base 1552 and other ways of attaching the cap and the base together are within the scope of the present disclosure.

The patella implant 1510 can be constructed using the manufacturing techniques and processes discussed herein. The base 1552 can be constructed using hybrid manufacturing. In a hybrid manufacturing process, the cap support 1554 and the anchoring projections 1534 can first be created or formed by conventional manufacturing methods, such as cold forming (e.g., stamping, cutting, deforming) a metal blank or by forging. The partially formed base 1552 is then placed in an additive manufacturing machine which builds the porous regions thereon (e.g., on the cap support 1554). In other embodiment, the base 1552 may be formed entirely by an additive manufacturing process. After the base 1552 is formed, the cap 1550 is then attached to (e.g., formed on) the base to complete the construction of the patella implant 1510. The polymeric cap 1550 may be formed by conventional methods such as compression molding.

For example, in one method of forming the patella implant 1510 involves forming the base 1552 (and associated elements such as the interconnection members, anchoring projections 1534, etc.) and then molding (e.g., compression molding) a material (e.g., a polymeric material) onto the base (e.g., cap support 1554) to form the cap 1550 with the articulating surface 1514. The molding includes substantially (if not completely) filling the first connecting recesses 1562 with the material, to form the first connecting members 1560. Likewise, the molding includes substantially (if not completely) filling the second connecting recesses 1578 with the material, to form the second connecting members 1576. Furthermore, the molding includes substantially (if not completely) filling the interconnecting voids 1594 with the material, to form the interconnecting struts 1592.

Figure 50:
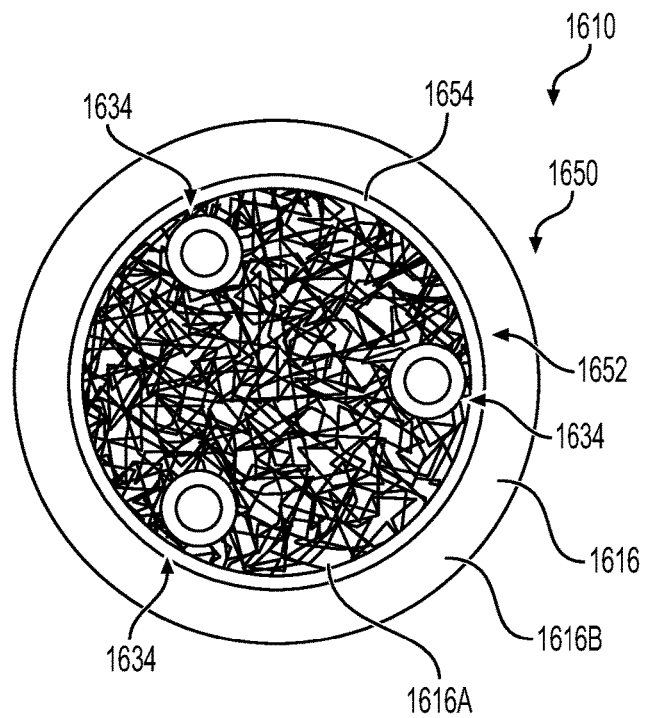
FIG. 50 is a bottom plan of a patella implant according to another embodiment of the present disclosure, the patella implant including the base of FIG. 47.

Referring to FIGS. 47-50, another embodiment of a patella implant according to the present disclosure is generally indicated at 1610 (FIG. 50). In this embodiment, the configuration of the base 1652 of the patella implant 1610 is different from the configuration of the base 1552 of the patella implant 1510 of FIGS. 36-46 (with the configuration of the cap 1650 being generally the same as the cap 1550 of FIGS. 36-46). In this embodiment, the porous region of the base 1652 is distally proud of the cap support 1654. In other words, the portion 1616A of the distal surface 1616 defined by the porous region is distally proud of the portion 1616B of the distal surface defined by the cap 1650. This ensures maximal contact of the porous region with the bone to facilitate ingrowth of the bone into the porous region. In addition, in this embodiment, the anchoring projections 1634 each includes a porous region. In the illustrated embodiment, the porous region generally extends over the entire exterior surface of the anchoring projections 1634, although other configurations are within the scope of the present disclosure. For example, the porous region may only extend over a portion of the anchoring projection (e.g., only along the sides). In the illustrated embodiment, the porous regions of the anchoring projections 1634 are continuous with the porous region of the base 1652 that defines the portion 1616A of the distal surface 1616. The porous regions of the anchoring projections 1634 and the base may have similar constructions and porosities, as illustrated, or different constructions and porosities.

In addition, in this embodiment, the anchoring projections 1634 are hollow (e.g., have a hollow core). The base 1652 defines an elongate cavity 1633 for each anchoring projection 1634. Each elongate cavity 1633 extends from the exterior surface of the cap support 1654, through the cap support and into the anchoring projection 1634. The distal end of the elongate cavity 1633 is adjacent the distal end 1636 of the anchoring projection 1634. In the illustrated embodiment, the distal end of the elongate cavity 1633 is closed. In other embodiments, the elongate cavity 1633 may extend through the anchoring projection 1634 (e.g., have an open distal end). The elongate cavity 1633 reduces the amount of material needed to construct the base 1652, thereby reducing manufacturing costs over solid anchoring projections. In addition, the elongate cavity 1633 forms another interconnecting member of the base 1652 for further securing the cap 1650 to the base 1652. In this embodiment, the cap 1650 may include elongate members or shafts (not shown), with each elongate member disposed (e.g., configured to be disposed) in a correspond one of the elongate cavities 1633. The elongate member of the cap 1650 may be formed by (e.g., during the) molding, as described herein.

Figure 51:
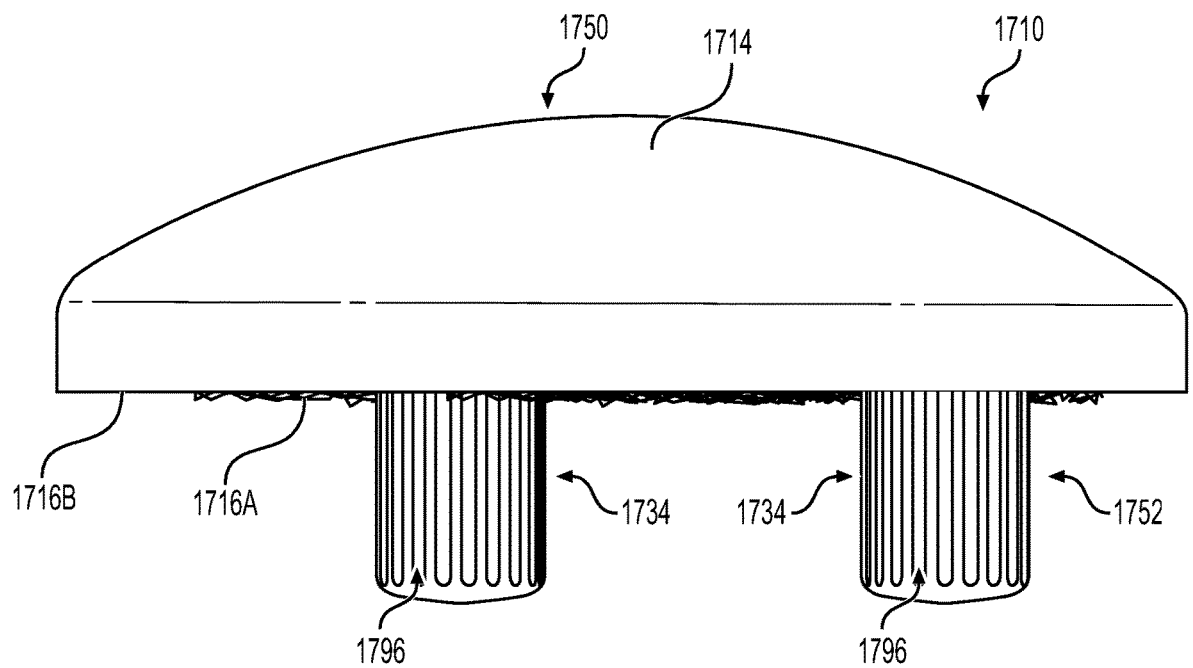
FIG. 51 is a side elevation of a patella implant according to another embodiment of the present disclosure.
Figure 52:
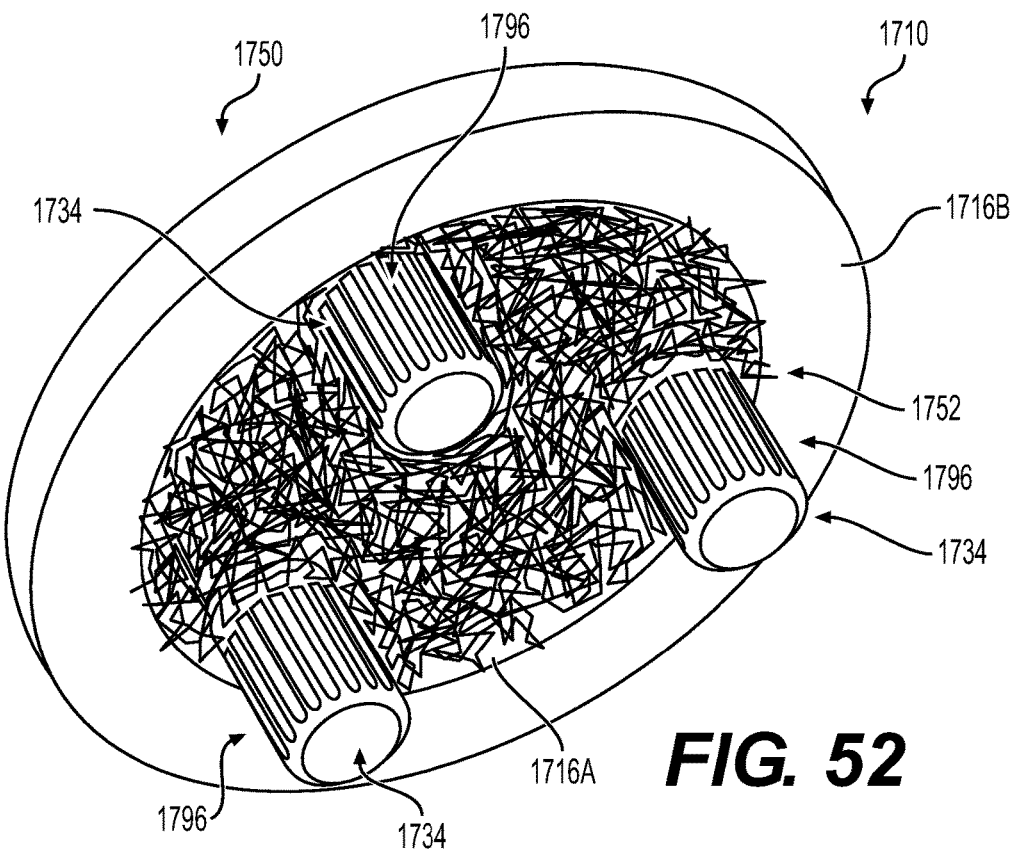
FIG. 52 is a bottom perspective of the patella implant of FIG. 51.

Referring to FIGS. 51 and 52, another embodiment a patella implant according to the present disclosure is generally indicated at 1710. In this embodiment, the base 1752 of the patella implant 1710 is generally the same as the base 1552 of FIGS. 36-46, except that the porous region of the base 1752 is distally proud of the cap support 1754, like the base 1652 of FIGS. 47-50. In addition, each anchoring projection 1734 includes bone connection structures 1796 (besides porous regions) on the exterior of the projection to facilitate the connection of the bone to the anchoring projections. The bone connection structure 1796 generally increase the surface area of the anchoring projections 1734 to increase the amount of contact between the bone and the anchoring projection, thereby increase the strength of the connection between the bone and the anchoring projection. In the illustrated embodiment, the bone connection structures 1796 comprise ridges, separated by grooves, extending along the outer surface of each anchoring projections 1734. The grooves defining the ridges enhance the press-fit with the bone by providing reliefs for the bone to compress into. The ridges and grooves generally run axially along the anchoring projections 1734. The size (e.g., width) of the grooves and/or ridges can be constant along the length of the anchoring projections 1734, as shown, or can vary along the length of the anchoring projections. Other dimensions (e.g., depth, diameter, etc.) of the ridges and/or grooves can vary or be constant as well. In the illustrated embodiment, the ridges and grooves are large enough to be visible to the human eye, although in other embodiments the ridges and/or grooves may be significantly smaller such that they cannot be observed by the human eye (e.g., are microscopic). Other configurations of the bone connection structures are within the scope of the present disclosure. For example, the bone connection structures can comprise spherical dimples, similar to golf balls. In still another example, the bone connection structure may comprise a rough exterior surface of the anchoring projections 1734.

Figure 53:
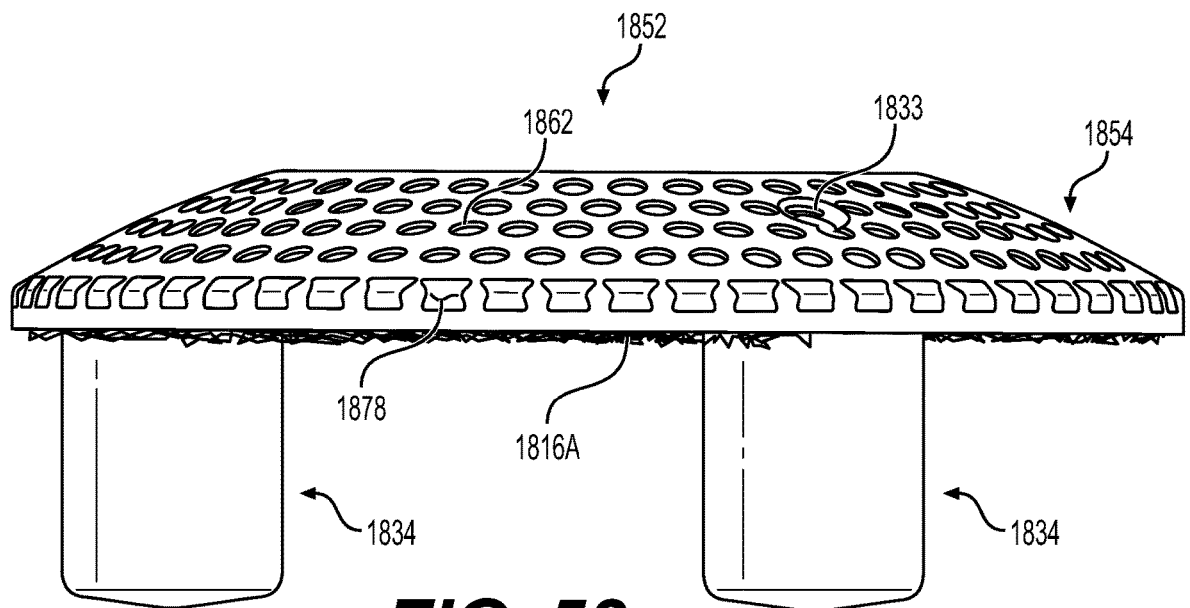
FIG. 53 is a side elevation of a base for a patella implant according to another embodiment of the present disclosure.
Figure 54:
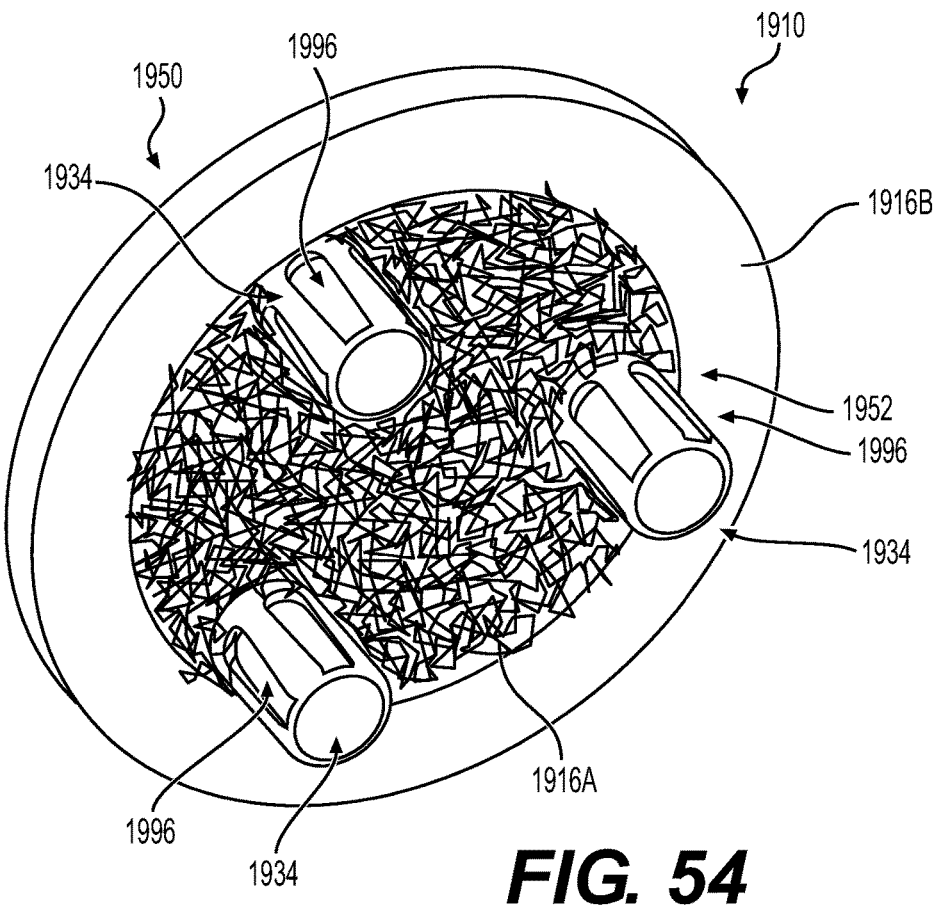
FIG. 54 is a bottom perspective of a patella implant according to another embodiment of the present disclosure.
Figure 55:
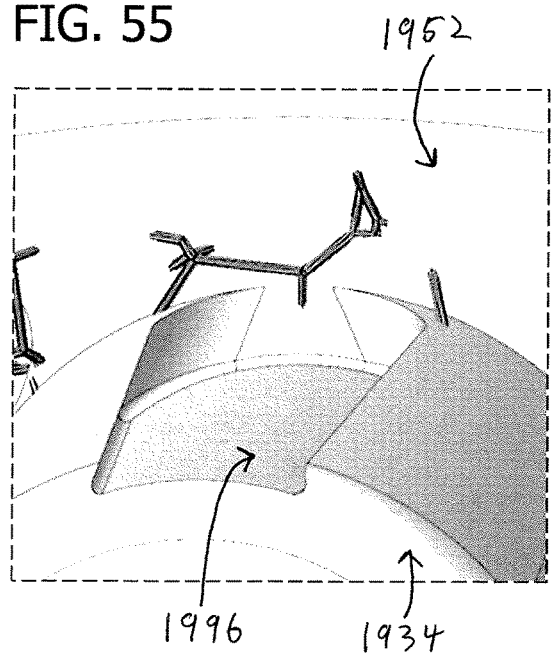
FIG. 55 is an enlarged, fragmentary perspective of an anchoring projection of the patella implant of FIG. 54.
Figure 56:
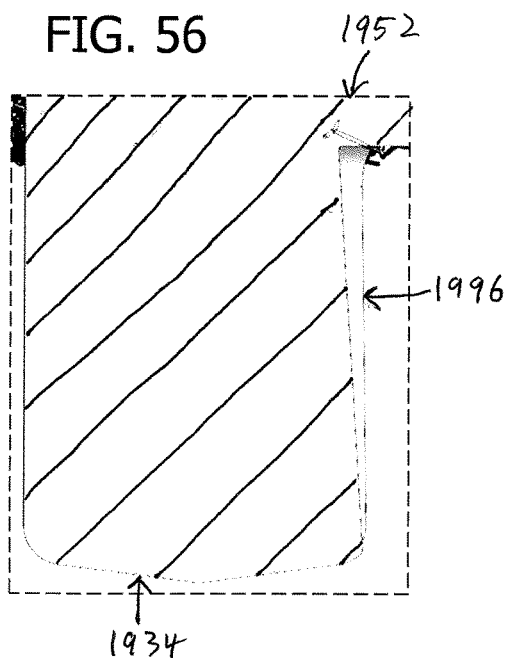
FIG. 56 is an enlarged, fragmentary cross-section of the anchoring projection of the patella implant of FIG. 54.
Figure 57:
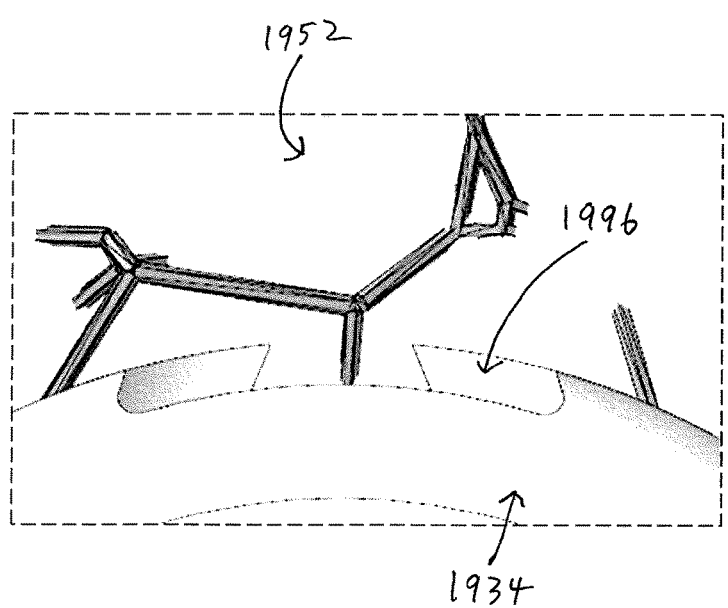
FIG. 57 is an enlarged, fragmentary bottom view of the anchoring projection of the patella implant of FIG. 54.

Referring to FIG. 53, another embodiment of a base for a patella implant according to the present disclosure is generally indicated at 1852. In this embodiment, the base 1852 is generally the same as the base 1652 of FIGS. 47-50, except that the anchoring projections 1834 do not have porous regions like the anchoring projections 1634 of FIGS. 47-50. As is apparent, a cap, as described herein, may be connected to the base 1852 to form a patella implant (not shown).

Referring to FIGS. 54-57, another embodiment of a patella implant according to the present disclosure is generally indicated at 1910. In this embodiment, the base 1952 of the patella implant 1910 is generally the same as the base 1752 of FIGS. 51 and 52, except for the configuration of the bone connection structure. In this embodiment, the bone connection structure 1996 includes dovetail grooves (e.g., a plurality of dovetail grooves). In one embodiment, each dovetail groove may taper (in one or more directions) along the anchoring projection 1934. In the illustrated embodiment, each dovetail groove tapers (e.g., narrows) in depth as the dovetail groove extends along the anchoring projection 1934, away from the porous region of the base 1952. In addition, in the illustrated embodiment, each dovetail groove tapers (e.g., narrows) in width as the dovetail groove extends along the anchoring projection 1934, away from the porous region of the base 1952. In another embodiment, each dovetail groove may remain a constant size along the length of the anchoring projection 1934. In yet another embodiment, each dovetail groove may taper (e.g., widen) in depth and/or width as the dovetail groove extends along the anchoring projection 1934, away from the porous region of the base 1952. In yet another embodiment, each dovetail groove may have one or more dimensions (e.g., depth, width, etc.) that remain constant and one or more dimensions (e.g., depth, width, etc.) that taper (e.g., narrows or widens) as the dovetail groove extends along the anchoring projection 1934, away from the porous region of the base 1952. For example, the depth of the dovetail groove can remain constant while the width tapers, or vice versa. In the illustrated embodiment, the bottom or base of the dovetail groove is rounded or curved. In another embodiment, the bottom of the dovetail groove may be generally flat or planar.

As is apparent, the implants 10, 110, 210, 310, 410, 510, 610, 710, 810, 910, 1010, 1110, 1310, 1510, 1610, 1710, 1910 disclosed herein are generally analogous to one another and, thus, for ease of comprehension, where similar or analogous parts are used between the various different implants (or elements thereof, such as bases 1552, 1652, 1752, 1852, and 1952), reference numerals having the same last two digits are employed. For example, tibial keel 28 is analogous to tibial keel 228 and, thus, these two tibial keels have the same last two digits of "28." In another example, base 1852 is analogous to base 1652 and, thus, these two bases have the same last two digits of "52." Thus, unless clearly stated or indicated otherwise, the above descriptions regarding the implants and elements thereof apply equally to all the analogous implants and the elements thereof. For example, at least some of the description related to anchoring projection 34 may also apply to anchoring projection 134 and/or vice versa. In another example, at least some of the description related to base 1552 may also apply to base 1852 and/or vice versa.

It is apparent and understood that the elements, features, and/or teachings set forth in each embodiment disclosed herein are not limited to the specific embodiment(s) the elements, features, and/or teachings are described in. Accordingly, it is apparent and understood that the elements, features, and/or teachings described in one embodiment may be applied to one or more of the other embodiments disclosed herein. For example, it is understood that any of the tibial keels disclosed herein may have sharp edges present on tibial keel 128. In another example, the methods and features of one position verification method may be used with another position verification method.

Modifications and variations of the disclosed embodiments are possible without departing from the scope of the disclosure defined in the appended claims.

When introducing elements of the present disclosure or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the disclosure, it is intended that all matter contained in the above description and shown in the accompanying drawings shall be interpreted as illustrative and not in a limiting sense.

What is claimed is:

1. A patella implant for knee arthroplasty comprising:
a cap including an articulating surface, the cap having a plurality of first connection members; and a base configured to be attached to the backside of a patella of a patient, the base including a cap support mounted to the cap, the cap support including a plurality of first connection recesses, wherein each first connection member of the cap is disposed in a corresponding one of the first connection recesses of the cap support to mount the cap to the base, wherein each first connection member of the cap interlocks with the corresponding one of the first connection recesses of the cap support, wherein each first connection recess has a recess mouth opposite a recess base, the recess mouth being smaller than the recess base, wherein the cap includes a plurality of second connection members and the cap support of the base includes a plurality of second connection recesses, wherein each second connection member of the cap is disposed in a corresponding one of the second connection recesses of the cap support to mount the cap to the base, wherein the second connection members have a different shape than the first connection members and the second connection recesses have a different shape than the first connection recesses, wherein the second connection members are disposed along a peripheral edge of the cap and the first connection members are disposed inward of the second connection members.

2. The patella implant of claim 1, wherein each first connection member has a connection end opposite an attached end, each attached end being smaller than the corresponding connection end, and wherein each connection end corresponds to the size and shape of the recess base and each attached end corresponds to the size and shape of the recess mouth.

3. The patella implant of claim 2, wherein the first connection member includes at least one connection member tapered surface disposed between the connection end and the attached end.

4. The patella implant of claim 3, wherein each first connection recess is at least partially defined by at least one cap support tapered surface of the cap support, and wherein each connection member tapered surface engages a corresponding cap support tapered surface to inhibit the withdrawal of the respective first connection member from the respective first connection recess.

5. The patella implant of claim 1, wherein the second connection recesses are disposed along a peripheral edge of the base and the first connection recesses are disposed inward of the second connection recesses.

6. The patella implant of claim 1, wherein the cap support includes a plurality of interconnecting voids, each interconnecting void extending between and interconnecting two adjacent second connection recesses, and wherein the cap includes a plurality of interconnecting struts, each interconnecting strut extending between and interconnecting two adjacent second connection members, each interconnecting strut disposed in a corresponding one of the interconnecting voids.

7. The patella implant of claim 1, wherein the base further includes at least one anchoring projection configured to be inserted into the backside of the patella.

8. The patella implant of claim 7, wherein the at least one anchoring projection includes a porous region.

9. The patella implant of claim 1, wherein the base includes a porous region configured to face the backside of the patella when the base is attached to the patella to enable ingrowth of bone into the base after the base is attached to the patella.

10. The patella implant of claim 9, wherein the porous region is distally proud of the cap support.

* * * * *